(12) United States Patent
Nybo

(10) Patent No.: US 10,980,817 B2
(45) Date of Patent: Apr. 20, 2021

(54) GENETICALLY MODIFIED HOST ORGANISM FOR EXPRESSING AN ANTHRACYCLINONE ANALOGUE, METHOD ASSOCIATED THEREWITH, AND SYNTHETIC NUCLEIC ACIDS

(71) Applicant: Ferris State University, Big Rapids, MI (US)

(72) Inventor: Stephen Eric Nybo, Big Rapids, MI (US)

(*) Notice: Subject to any disclaimer, the term of this patent is extended or adjusted under 35 U.S.C. 154(b) by 41 days.

(21) Appl. No.: 16/015,821

(22) Filed: Jun. 22, 2018

(65) Prior Publication Data

US 2018/0369256 A1   Dec. 27, 2018

Related U.S. Application Data

(60) Provisional application No. 62/524,244, filed on Jun. 23, 2017.

(51) Int. Cl.

| | | |
|---|---|---|
| *A61K 31/5585* | (2006.01) | |
| *C12R 1/545* | (2006.01) | |
| *A61K 31/704* | (2006.01) | |
| *C12R 1/58* | (2006.01) | |
| *C12R 1/47* | (2006.01) | |
| *C12P 15/00* | (2006.01) | |
| *C12P 19/56* | (2006.01) | |
| *C12N 15/52* | (2006.01) | |
| *C12R 1/465* | (2006.01) | |

(52) U.S. Cl.
CPC ........ *A61K 31/5585* (2013.01); *A61K 31/704* (2013.01); *C12N 15/52* (2013.01); *C12P 15/00* (2013.01); *C12P 19/56* (2013.01); *C12R 1/47* (2013.01); *C12R 1/545* (2013.01); *C12R 1/58* (2013.01); *C12R 1/465* (2013.01)

(58) Field of Classification Search
None
See application file for complete search history.

(56) References Cited

PUBLICATIONS

Jaana Kantola Microbiology 2000) 146, 155-163. Elucidation of anthracyclinone biosynthesis by stepwise cloning of genes for anthracyclines from three different *Streptomyces* spp. (Year: 2000).*
Niemi et al (Biosynthetic Anthracycline Variants, (Topics in current chemistry 282, 101-140, 2008 (Year: 2008).*
Cloning and characterization of *Streptomyces galilaeus aclacinomycins* polyketide synthase (PKS) cluster Kaj Raty et al Gene 293, 115-122.2002 (Year: 2002).*

* cited by examiner

*Primary Examiner* — Kagnew H Gebreyesus
(74) *Attorney, Agent, or Firm* — Warner, Norcross + Judd, LLP

(57) ABSTRACT

Disclosed is a genetically modified host organism for expressing an anthracyclinone analogue. The genetically modified host organism comprises (i) synthetic nucleic acids; (ii) a biosynthetic pathway encoded by the synthetic nucleic acids, the (ii) biosynthetic pathway comprising a ketosynthase alpha, a ketosynthase beta/chain-length factor, an acyl carrier protein, a 3-oxoacyl-ACP synthase, a propionyl-CoA acyltransferase, a 9-ketoreductase, an aromatase/cyclase, and a second/third-ring cyclase; and (iii) a promoter positioned upstream of and operatively associated with the (ii) biosynthetic pathway. A method and corresponding synthetic nucleic acids are also disclosed.

17 Claims, No Drawings
Specification includes a Sequence Listing.

```

SEQUENCE LISTING

<160> NUMBER OF SEQ ID NOS: 40

<210> SEQ ID NO 1
<211> LENGTH: 1291
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gaaagaggag aaatactaga tgaccgcccg tcgcgtggtc atcaccggcc tgggcgtcat      60
cgccccgggt ggcatcggca ccaaggcctt ctgggagcgg atcgtctccg gcgtctccgc     120
cacccgcacc atcaccgcct cgacgcctc cgagttccgc tcccggatgg ccgccgagtg      180
cgacttcgac ggcgtccgct ccggcctgac cgtccgggac accgcccgcc tggaccgggc     240
cacccagttc gccgtggtgg ccgcccgcga ggccctggcc gactccggca tcgagatcga     300
cgagcgcaac gcccaccgga ccggcgtctc cctgggctcc gccgtcggct gcacccagaa     360
gctggaggaa gagtacgtgg cccgctccga cggtggccag cggtggctcg tggaccacgc     420
cgccggcacc ccgtacctgt acgactactt cgtcccgtcc tcgatggccg ccgaggtcgc     480
ctgggaggcc ggcgccgagg gccggccgc cctggtctcc gccggctgca cctcgggcct     540
ggactccctg ggccacgccc tggacctgat ccgcgagggc gccgtggaca tcatgatcgc     600
cggcggctcc gacgcccca tcgccccat caccgtggcc tgcttcgacg ccatcaaggc     660
cacctcgccg cgcaacgaca ccccggagca cgcctcccgg ccgttcgacc gcacccggtc     720
cggcttcgtc ctgggcgagg gcgccgccgt cctggtcctg gaggagcggg agtccgccct     780
gcgccgcggt gcccaaatct acgccgagat cgccggctac gccggccgcg ccaacgccca     840
ccacatgacc ggcctgcggc ccgacggcct ggagatgtcc gccgccatca ccggcgccct     900
ggacgacgcc cgcatcgacc gggaggccgt gggctacgtc aacgcccacg gcaccgcgac     960
ccgccagaac gacatccacg agaccgccgc catcaagcac tccctgggcg agcacgcccg    1020
ccgggtcccg gtctcctcca tcaaggccgt catcggccac tccctgggcg ccgtgggctc    1080
catcgaggcc gtcgcctccg ccctggtcat ccgccacggc gtcgtcccgc ccaccgccgg    1140
cctgcacgag ccggacccgc agctggacct ggactacgtc ccctgatcg cccgggacca    1200 ggccaccgac accgtcctga ccgtgggctc cggcttcggc ggcttccagt ccgcgatggt    1260
cctgacctcg gccgagggcg gccggtcctg a                                    1291
```

<210> SEQ ID NO 2
<211> LENGTH: 1243
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
gaaagaggag aaatactaga tgtccgccgc caccgtggtc accggcatcg gcgtcctggc    60
cccgaacggc atcggcgccg aggagttctg ggccgccacc ctgcgggccg agtccggcat   120
cggccggatc acccacttcg agcccgcctc ctaccccctcc cggctggccg gcgaggtcac   180
cggcttctcc gcccgcgagc acctgccctc ccggctggtc ccgcagaccg accgaccac    240
ccagttcgcc ctgaccggct ccgagtgggc cctgcgggac tccggcctgt ccgccgacac   300
cctgccggcc ggtgagcgcg cgtcgtcac cgcctccgcc tccggcggct tcgagttcgg    360
ccagcgggag ctgggccacc tgtggggcaa ggacccgcgc cacgtctccg cctacatgtc   420
cttcgcctgg ttctacgccg tcaactccgg ccagatcagc atccgccacg acctgcgggg   480
cccgaccggc gtcctggtca ccgaccaggc cggcggcctg gacgccgtgg cccaggcccg   540
ccggcgcatc cgcaagggca ccccggtcat gctgtccggc ggcatggacg cctccctgtg   600
cccgtacggc ctggtcgccc agatcagcgc cggcatgctg tccgagtccg acgacccac    660
ccgcgcctac cggccgttcg accccgccgc cgacggccac gtcccgggcg agggcggcgc   720
catcctgacc ctggaggacg cgaccgcgc ccgcccccgg ggtgcccggt ccacggcga    780
gatcagcggc tacgccgcca ccttcgaccc gcgcccgggc tccggccggc ccgccaacct   840
ggaccgcgcc atccgcggtg ccctggccga cgccggcctg tccccgcgcg acatcgcctt   900
cgtcctggcc gacggcgccg gcgagcccga gccggaccgc gccgaggccc gtgccctgac   960
cgacgtcttc ggcccgcgcg cgtccccgt caccgtcccg aagtccatga ccggccggct  1020
gtacgccggc gccgccccgc tggacctggt caccgccctg ttcgccctgc gggacggcgt  1080
cgtcccgccc accgtccacg tggacgagcc ggaccccgcc tacgacatcg acctggtcac  1140
cggctccgcc cgccccgtcc ggggcgacgc cgccctggtc ctggcccgcg ccggggcgg   1200
cttcaactcc gcgatggtcg tccgtcgccc gccggccgcc tga                   1243
```

<210> SEQ ID NO 3
<211> LENGTH: 295
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gaaagaggag aaatactaga tgtccgcctt caccgtcgag gagctgttcc agatcatgcg    60
cgagtgcgcc ggcgaggaag aggccgtgga cctggccgac gccgccgagc aggagttcgc   120
cctgctgggc tacgactccc tggccctgat ggaggccatc tcccgcgtcg agcggggcct   180
gggcatcgcc ctgccggagg agaccgtggg cgaggtcctg accccggccg ccttcgtgga   240
cgtggtcaac gccgagctgg cccgtccgc cccggtcgtc gaggccgccg gttga         295
```

<210> SEQ ID NO 4
<211> LENGTH: 1129
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
gaaagaggag aaatactaga tgaccgagga gcacctggac ccggccggcg gcgccccgct    60
```

-continued

```
ggcccaggcc ccggcccagg acatccgcat cgccggctgc gccgtctggc tgccgccccg    120
ggcccccgtc gcccaggccg tcgccgccgg tctgtgcgac gaggccctgg ccaccgccac    180
cgcgatggtc tccgtcgccg tcgcccagga cgagccggcc cccgagatgg ccgcccgtgc    240
cgcccgcacc gccctggccc gcggcggctc cgacgacgtc tccctgatcc tgcacgcctc    300
cttcttctac cagggccacg acctgtgggc ccccgcctcc tacgtccagc gcgtggccgt    360
gggcaaccac tgcccggcca tcgaggtggg ccaggtctcc aacggtggca tggccgccct    420
gggcctggcc gtggaccacc tgtccgccgg ccgcccggcc ggcgccgccg tcgccgcgt    480 cctggtcacc accggcgacg ccttccgtcc gccgggcttc gaccgctggc ggtccgaccc    540
cggcaccttc tacggcgacg gcggcaccgc cctggtcctg tcctcccagg aaggcttcgc    600
ccgcatccgg ggcctggcca ccgtctccgc ccccgagctg gagggcatgc accgcggcga    660 cgacccccttc ggctccgccc cgttctccca ccggccggtg gtggacctgg aggcctgcaa    720
gaaggacttc ctggcctccc gccgggtcac ccaggtcatc gccgcctccg ccgccgccca    780
ggacgccgcc ctgggccagg ccctggccgc cgccggtgcc gagctggccg acatcgaccg    840
cttcgtcctg ccgcacatgg ccgcaagcg gctgcgcgcc ggcttcctga accgcctggg    900
catcggcgag gaccgcacca cctgggagtg gtcccggggc gtcggccacc tgggcgccgg    960
cgaccagatc gccggcttcg accacctggt gggctccggc tccctgggcc ccggcgacct   1020
ggtcctgtgg atgtccgtgg cgccggctt cacctactcc tgcgccgtcg tcgagatgct   1080
ggagcgcccc ggctgggccg ccaccgccgg caccgccggc gccgcctga              1129
```

<210> SEQ ID NO 5
<211> LENGTH: 1063
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gaaagaggag aaatactaga tgaccggcac cgccggcgcc ctgccgtgg ccctgctgct     60 gcccggccag ggctcccagc accgtcgcat ggccgccggt ctgtacggcc acgagcccgt    120
cttcaccgag gcgatggacg agttcttcga cgccgccggt cccgagggcg acccgctgcg    180
cgacgactgg ctggccgagc ggcccgtcac cgacatcgac cacgtcaccc gctcccagcc    240
cctgctgttc gccgtggacc acgccctggg ccggctggtc ctgggccgcg cgtccggcc    300 ggccgcactg ctgggccact ccatcggcga gctggccgcc gcaaccctgg ccggcgtctt    360 cgcccccgcgc gacgccgccg gcctggtcct ggaccggatc cgccggctgt ccgccgcccc    420
gcccggcggc atgctggccg tcgccgcctc caccgccgag gtcgccccct acctgcgcgg    480
cgacgtcgtc gtcggcgccg tcaacgcccc gcgtcagacc gtcctggccg gcccggacgg    540 cccccctggac gaggtggacc gcgccctgcg ggaggccggc ttcgtctgcc gccgggtccc    600
ctccctgtcc gccttccact ccccgtcct ggagccggcc tgccgcggcg ccgccccgct    660
gttcgccgcc gcatgcaagc acccgccgc cgtcccggtc cactccgcct acaccgccgc    720
cccgctgacc gagtccgaca tcgacgaccc ggccttctgg gccgccagc cggtcgcccc    780 cgtcctgttc tggccggccc tggagggcct gctggccacc ggcgaccacc tgctggtcga    840
ggtcggcccc ggcagggcc tgtcccagct ggtccgccgg caccggccg tccgccgggg    900 cggctccgcc gtcgtctccc tgctgccgc ccgccccggt ccgccggagg ccgaccgggc    960
```

```
cgccgtcgcc gccgcaaccg agcagatcac cgccgccggc cgccaggccg ccccggcctc    1020
cgccgaccac ggccgcccct cccggcaggc cgccgccggt tga                     1063

<210> SEQ ID NO 6
<211> LENGTH: 805
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaaagaggag aaatactaga tgtccgaggc cgccgaccgg gtggccctgg tcaccggcgg     60
cacctcgggc atcggcctgg ccgtcgtccg gaagctggcc caggacggca cccgcgtctt    120
cctgtgcgcc cgggacgagt ccgccatcac cggcaccgtc aaggagctcc aggcctccgg    180
cctggaagtg gacggcgccc cctgcgacgt ccgctccacc gccgacgtgg accggctggt    240
ccagaccgcc cgcaaccggt tcggcccat cgacatcgtc gtcaacaacg ccggccgcgg    300
cggcggcggc gtcaccgccg agatcaccga cgacctgtgg ctggacgtcg tggacaccaa    360
cctgtccggc gccttccggg tcacccgggc cgtcctgacc ggcggcgcca tgcaggagca    420
cggctggggc cggatcatct ccatcgcctc caccggcggc aagcagggcg tcgccctggg    480
cgccccgtac tccgcctcca agtccggcct gatcggcttc accaaggccg tggccctgga    540
gctggccaag accggcatca ccgtcaacgc cgtctgcccc ggctacgtgg agaccccgat    600
ggcccagggc gtccgccagc ggtacgccgc cttctgggc atcaccgagg acgacgtcct    660
ggagaagttc caggccaaga tcccctggg ccgctactcc atgccggagg aagtcgccgg    720
catggtccac tacctggcct ccgactccgc cgactccatc accgcccagg ccatcaacgt    780
ctgcggcggc ctgggctcct actga                                         805

<210> SEQ ID NO 7
<211> LENGTH: 967
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaaagaggag aaatactaga tgtccgagct gcccctccag cagaccgagc acgagatcca     60
cacctcgggc cgccccggacg ccgtcttcgc cgtcctggcc gacgcccgtg cctggccggc    120
cgtcttcccg ccctccgtcc acgtggagca ggtggagcac accggctcct ccgagcgcat    180
ccggatctgg gccaccgcca acggctccct gcgcacctgg acctcgcgcc gcgagctgga    240
cgagcgggcc cgccggatcc gcttccggca ggaagtctcc gcccacccgg tggccgcgat    300
gggcggcgag tggatcgtgg aggaagccgg cgacggcggc acccgcgtcc ggctgaccca    360
cgacttccgg gccgtggacg acgaccccga gaccatcggc tggatccacc gggccgtgga    420
ccggaactcc gaggccgagc tggcctccct gcgcaccgcc ctggagcggc ccgacggcac    480
cgcccccacc accttcgagg acaccgtggt ggtccgcggt cgcgccgagg acgtctacga    540
cttcctgcac cggtccgacc tgtggaagaa cgcctgtcc cacgtggccc ggatcgccgt    600
caaggaagag gagcccggcc tccagcacat ggagatggac accctgaccg ccgacggctc    660
cgtccacacc accgcctccg tccgggtctg cttcccgag cgtcgcgtca tcgtctacaa    720
```

```
gcagctgcgg accccgcccc tgctggccct gcacctgggc cgctggtccg tccggcccgc    780
cgacgacggc gacggcatcg ccgtcacctc ggcccacacc gtctccgtcg cccgctccgc    840
catcccgggc gtcctgggcg ccggcgcctc cgagaccgac gccgtggact tcgtccgtcg    900
cgccctgggc cgcaactccc tgctgaccct ggaggccgcc cggcagtacg ccgagtcctc    960
cgcctga                                                              967
```

<210> SEQ ID NO 8
<211> LENGTH: 799
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
gaaagaggag aaatactaga tgcgcatcat cgacatctcc tccgccgtgg acgcctccgg     60
ctgggagccc gacgaggtgc ggcacgaggt ccactcccg cgggagggcg ccgtccacat    120
gtccgaggag atgcgccggc acttcggcgt ggccttcgac cccgacgagc tgccggaggg    180
cgagttcctg tccctggacc ggctgaccct gacctgcac accggcaccc acatcgacgc    240
cccctcccac tacggctccc gggcccacta cggcgacggt cgcccgcgca acatcgacga    300 gctgccctg gactggttct acggcccgg cctgctgctg gacctgaccg gctgcgacgg    360
cccacccgcc ggcgccggcg acctggagaa ggagctggcc cgcatcggcc gggtcccgga    420
gcccggcacc atcgtcctgc tgcgcaccgg cgcctccgag cgggccggca ccgagcagta    480
cttcaccgac ttcaccggcc tggacggccc ggccgtcaac ctgctgctgg accacggcgt    540
ccgggtcatc ggcaccgacg ccttctcccc tggacgcccc ttcggcgccg tcatccgccg    600
ctaccgcgag accggcgacc ggtccgtcct gtggcccgcc cacgtcaccg gccgccaccg    660
ggagtactgc cagatcgagc ggctgggcaa cctggccgcc ctgcccggct gcgacggctt    720
ccaggtggcc tgcttccccg tcaagatcac cggcggcggc gccggctgga ccgggccgt    780 cgccttcgtg gacgagtga                                                799
```

<210> SEQ ID NO 9
<211> LENGTH: 409
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gaaagaggag aaatactaga tgccccagcc ggagcccaac gacgccggct ccggctccgt     60
caccttcgtc aaccgcttca ccctgtccgg ctccgccgag acttcgagg ccgccttcgc    120 cgagaccgcc gagttcctgt gccgccggcc cggcttccgc tggcacgccc tgctggtccc    180
cgccgacacc ggccccggct ccgccgacgc ccgcccgcag tacgtcaaca tcgccgtctg    240
ggacgacgag gcctccttcc gggccgccgt cgcccacccc gagttccccg cccacgccgc    300
cgcactgcgg gccctgtcca cctcggagcc gaccctgtac cgccaccggc agatccgcgt    360 cgccccgac gtcccggccg tctccggccc gggtggccgc accacctga                409
```

<210> SEQ ID NO 10
<211> LENGTH: 880
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 10
gaaagaggag aaatactaga tgcaggactc ctcctacaag gagcaggtca cccaggcctt     60
cgaccagtcc tcctccacct acgaccgcct gggcgtcgag ttcttcaccc cgatgggccg    120
cccgctggtc gagatcagcg agcccgtcac cggcgagcgg gtcctggaca tcggctgcgg    180
ccggggcgcc tgcctgttcc cggccgccga aaggtcggc ccccagggcc gcgtccacgg     240
catcgacatc gcccccggca tgatcgagga agcccgcaag gaagccgccg agcgcggcct    300
gcggaacatc gccctggacg tcatggacgc cgagaccccg gagctgccgg cccgctcctt    360
cgacctggtc atgggctcct actccgtcat cttcctgccc gacgccgtgg gcgccctggc    420
ccggtacgcc ggcatcctgg accacggcgg ccggatcgcc ttcacctcgc ccgtcttccg    480
cgccggcacc ttcccttcc tgccgcccga gttcaccccg ctgatcccgc aggccctgct    540
ggagcacctg ccggagcagt ggcgcccgga ggccctggtc cgccggttca actcctggct    600
ggagcgggcc gaggacctgc tgcggaccct ggagcgctgc ggctacacct cggtcgccgt    660
caccgacgag cccgtgcgga tgaccgccct gtcctccgag gcctgggtgg actggtccca    720
cacccagggc atgcggctgc tgtggcagaa cctgccccag gcccagcgga ccgagctgcg    780
cgcccggctg tcgagggcc tggacaagct gtccgacgcc accggcgccc tggccatcga    840
cgtcccggtc gcttcgtca ccgcccgggt cgcccactga                           880

<210> SEQ ID NO 11
<211> LENGTH: 457
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaaagaggag aaatactaga tgtccaccca gatcgacctg gtccgtcgca tggtcgaggc     60
ctacaacacc ggcaagaccg acgacgtcgc cgagttcatc cacctggagt acctgaaccc    120
cggcgccctg gagcacaacc ccgagctgcg gggccccgag gccttcgccg ccgccgtcac    180
ctggctgaag tacgccttct ccgaggaagc ccacctggag gagatcgagt acgaggagaa    240
cggcccctgg gtccgggcca agctggccct gtacggccgg cacgtgggca acctggtggg    300
catgcccgcc accggccgcc ggttctccgg cgagcagatc cacctgatcc ggatcgtgga    360
cggcaagatc cgggaccacc gggactggcc ggactacctg gcacctacc gccagctggg    420 cgagccgtgg cccaccccgg agggctggcg gccgtga                             457

<210> SEQ ID NO 12
<211> LENGTH: 775
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gaaagaggag aaatactaga tggagaacac ccagcggtcc gtcatcgtca ccggcggcgg     60
ctccggcatc ggccgggccg tcgccgtgc cttcgccgcc gcggcgacc gggtcctggt     120 cgtcggccgc accgccggcc cgctggccga gaccgtggac ggccacaagg acgcccacac    180
```

-continued

```
cctggccgtg gacatcaccg acccggccgc accggaggcc gtggtccgcg aggtccgcga    240
gcggctgggc ggcgtcgtgg acgtcctggt caacaacgcc gccaccgccg ccttcggcca    300
cctgggcgag ctgcaccgca ccgccgtcga ggcccaggtg gccaccaacc tggtggcccc    360
cgtcctgctg acccaggccc tgctgggccc cctggagacc gcctccggcc tggtcgtcaa    420
catcggctcc gccggcgccc tgggtcgccg cgcctggccg ggcaacgccg tctacggcgc    480
cgccaaggcc ggcctggacc tgctgacccg ctcctgggcc gtcgagctgg gcccgcgcgg    540
catccgggtc gtcggcgtcg ccccggcgt catcggcacc ggcgccggcg tccgcgccgg    600
catgtcccag gaagcctacg acggcttcct ggaggcgatg ggccagcggg tcccgctggg    660
ccgcgtcggt cgcccggagg acgtcgcctg gtgggtcgtc cgcctggccg accccgaggc    720
cgcctacgcc tccggcgccg tcctggccgt ggacggcggc ctgtccgtca cctga         775
```

<210> SEQ ID NO 13
<211> LENGTH: 1489
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 13

```
gaaagaggag aaatactaga tggccctgac caagccggac gtcgatgtcc tggtcgtcgg     60
cggcggcctg ggcggcctgt ccaccgcccT gttcctggcc cgccggggcg cccgcgtcct    120
gctggtcgag cgccacgcct ccacctccgt cctgccgaag gccgccggcc agaacccgcg    180
gacgatggag ctgttccgct cggcggcgt cgccgacgag atcctggcca ccgacgacat    240
ccgcggcgcc cagggcgact tcaccatcaa ggtcgtcgag cgcgtcggcg gccgggtcct    300
gcactccttc gccgagtcct tcgaggagct ggtcggcgcc accgagcagt gcaccccgat    360
gccctgggcc ctggccccgc aggaccgcgt cgagccggtc ctggtcgccc acgccgccaa    420
gcacggcgcc gagatccgct tcgccaccga gctgacctcc ttccaggccg gcgacgacgg    480
cgtcaccgcc cggctgcggg acctgggcac cggcgccgag tccaccgtct ccgcccgcta    540
cctggtcgcc gccgacggcc cgcggtccgc catccgcgag tccctgggca tcacccggca    600
cggccacggc accctggccc acttcatggg cgtcatcttc gaggccgacc tgaccgccgt    660
cgtcccgccc ggctccaccg gctggtacta cctgcaacac ccggacttca ccggcacctt    720
cggccccacc gaccggccga accgccacac cttctacgtc gccaccaccc cggagcgcgg    780
cgagcggccg gaggactaca ccccgcagcg ctgcaccgag ctgatccgcc tggccgtcga    840
tgccccgggc ctggtcccgg acatcctgga catccaggcc tgggacatgg ccgcctacat    900
cgccgaccgg tggcgcgagg gccggtcct gctggtcggc gacgccgcca aggtcacccc    960
gcccaccggc ggcatgggcg caacaccgc catcggcgac ggcttcgacg tcgcctggaa   1020
gctggccgcc gtcctgcgcg cgaggcgg cgagcgcctg ctggactcct acggcgccga   1080
gcggtccctg gtctcccggc tggtcgtcga tgagtccctg gccatctacg cccagcgcat   1140
ggccccacac ctgctgggct ccgtcccgga ggagcgcggc accgcccagg tcgtcctggg   1200
cttccgctac cggtccaccg ccgtcgccgc cgaggacgac gaccccgagc cgaccgagga   1260
cccgggcgcg ccgtccggcc gccgggcTT ccgggcccg cacgtctgga tcgagcagga   1320
cggcacccgc cggtccaccg tcgagctgtt cggcgactgc tgggtcctgc tggccgcccc   1380
ggagggcggc gcctggccgg ccgcccgcc cgccccgccc gcatctgggg cctccgcctc   1440
```

```
cacctccatc tcctccgccg ccatgtcccc gccgccccca gccaactga            1489
```

<210> SEQ ID NO 14
<211> LENGTH: 424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
gaaagaggag aaatactaga tggtgtccgc cttcaacacc ggccgcaccg acgacgtcga     60
cgagtacatc cacccggact acctgaaccc ggccaccctg gagcacggca tccacaccgg    120
ccccaaggcc ttcgcccagc tggtcggctg ggtccgggcc accttctccg aggaagcccg    180
cctggaggaa gtccggatcg aggagcgggg ccctgggtc aaggcctacc tggtcctgta    240
cggccgccac gtgggccggc tggtcggcat gcctccgacc gaccgccggt tctccggcga    300
gcaggtccac ctgatgcgga tcgtcgacgg caagatccgc gaccacccgg gactggcccga   360
cttccagggc accctgcgcc agctgggcga cccgtggccc gacgacgagg gctggcggcc    420
ctga                                                                 424
```

<210> SEQ ID NO 15
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
gaattcgcgg ccgcttctag agggtaccag cccgacccga gcacgcgccg gcacgcctgg     60
tcgatgtcgg accggagttc gaggtacgcg gcttgcaggt ccaggaaggg gacgtccatg    120
cgagtgtccg ttcgagtggc ggcttgcgcc cgatgctagt cgcggttgat cggcgatcgc    180
aggtgcacgc ggtcgatctt gacggctggc gagaggtgcg gggaggatct gaccgacgcg    240
gtccacacgt ggcaccgcga tgctgttgtg ggcacaatcg tgccggttgg taggatccta    300
ctagtagcgg ccgctgcag                                                 319
```

<210> SEQ ID NO 16
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
gaattcgcgg ccgcttctag aggctgctcc ttcggtcgga cgtgcgtcta cgggcacctt     60
accgcagccg tcggctgtgc gacacggacg gatcgggcga actggccgat gctgggagaa    120
gcgcgctgct gtacggcgcg caccgggtgc ggagcccctc ggcgagcggt gtgaaacttc    180
tgtgaatggc ctgttcggtt gctttttta tacggctgcc agataaggct tgcagcatct    240
gggcggctac cgctatgatc ggggcgttcc tgcaattctt agtgcgagta tctgaaaggg    300
gatacgctac tagtagcggc cgctgcag                                       328
```

<210> SEQ ID NO 17
<211> LENGTH: 462

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

| gaattcgcgg ccgcttctag agcccgccgc gggcgctgga ggctcgggcg ggccccgggc | 60 |
| cggaggcggc cgcgaccacg acgcccgcgg gacgtgacga gcggcacgac tcgacgactc | 120 |
| cgggctcctt tgacgctgtc cgtcgcgccg ggtagcgtag gacaccgtgc ccgcgccgtc | 180 |
| gggccctcgc gcgtgcactc ggtcgaccgc tccctgccgg agtgggtgcg ggtgcacggg | 240 |
| gtggctcccc acctcctctc ggatcggtcc tcgcggactg ccgccgtgcg gaggaccggg | 300 |
| gcgacacgcc cgggcgcggg ggtcggtgcg ggactccaga cctccggggt agtcgtgcga | 360 |
| cgggcgacga tccgggccga gccggccgtc ctgggtgacg ggtgccggtc agaccagaga | 420 |
| acaccgacag acggagacgt atactagtag cggccgctgc ag | 462 |

<210> SEQ ID NO 18
<211> LENGTH: 548
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

| gaattcgcgg ccgcttctag agtccgcgcc gccggcccga cggtgcccgg ccccgtaccc | 60 |
| ccccgggtg gtgcggggcc gggcaccggc cttttggcgc tgcggagttg acggaagttg | 120 |
| gccgaaccgg atgcgctcgg cgcccggggg ctgaaagatg ctcacagccc ctttccacgg | 180 |
| cggtccggga ggggaggccg ggcaaccggt tttcggggc ggagtgtccg gtatgcggac | 240 |
| ggccgcgccc gatagatgtg taacgagtcc gtttcgcaac catctatctc ggatcggttt | 300 |
| gtccggattt tggaagatgt gagtgtcagg tgtgatcgaa ccgagaccaa aagggtgtgg | 360 |
| tcgggccgaa caccatggct aatagttgag cgcgtagagc tcgggtcaat gggtcacgcg | 420 |
| ctgtggggag cgccgactca cgagcacact ggggcactcg atcttcgccg tcaggggtgt | 480 |
| cggcggatcg tcctgtgccc tctcttgcag tgaacaagtg gactcattac tagtagcggc | 540 |
| cgctgcag | 548 |

<210> SEQ ID NO 19
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| atgaattcgc ggccgcttct agagtgttca cattcgaacg gtctctgctt tgacaacatg | 60 |
| ctgtgcggtg ttgtaaagtc gtggccagga gaatacgaca gcgtgcagga ctggggagt | 120 |
| gcgcattact agtagcggcc gctgcagta | 149 |

<210> SEQ ID NO 20
<211> LENGTH: 1333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

| | |
|---|---|
| gaattcgcgg ccgcttctag agaaagagga gaaatactag atgaccgccc gtcgcgtggt | 60 |
| catcaccggc ctgggcgtca tcgccccggg tggcatcggc accaaggcct tctgggagcg | 120 |
| gatcgtctcc ggcgtctccg ccacccgcac catcaccgcc ttcgacgcct ccgagttccg | 180 |
| ctcccggatg gccgccgagt gcgacttcga cggcgtccgc tccggcctga ccgtccggga | 240 |
| caccgcccgc ctggaccggg ccacccagtt cgccgtggtg gccgcccgcg aggccctggc | 300 |
| cgactccggc atcgagatcg acgagcgcaa cgcccaccgg accggcgtct ccctgggctc | 360 |
| cgccgtcggc tgcacccaga agctggagga agagtacgtg gcccgctccg acggtggcca | 420 |
| gcggtggctc gtggaccacg ccgccggcac cccgtacctg tacgactact tcgtcccgtc | 480 |
| ctcgatggcc gccgaggtcg cctgggaggc cggcgccgag ggcccggccg ccctggtctc | 540 |
| cgccggctgc acctcgggcc tggactccct gggccacgcc ctggacctga tccgcgaggg | 600 |
| cgccgtggac atcatgatcg ccggcggctc cgacgccccc atcgccccca tcaccgtggc | 660 |
| ctgcttcgac gccatcaagg ccacctcgcc gcgcaacgac accccggagc acgcctcccg | 720 |
| gccgttcgac cgcacccggt ccggcttcgt cctgggcgag ggcgccgccg tcctggtcct | 780 |
| ggaggagcgg gagtccgccc tgcgccgcgg tgcccaaatc tacgccgaga tcgccggcta | 840 |
| cgccggccgc gccaacgccc accacatgac cggcctgcgg cccgacgccc tggagatgtc | 900 |
| cgccgccatc accggcgccc tggacgacgc ccgcatcgac cgggaggccg tgggctacgt | 960 |
| caacgcccac ggcaccgcga cccgccagaa cgacatccac gagaccgccg ccatcaagca | 1020 |
| ctccctgggc gagcacgccc gccgggtccc ggtctcctcc atcaaggccg tcatcggcca | 1080 |
| ctccctgggc gccgtgggct ccatcgaggc cgtcgcctcc gccctggtca tccgccacgg | 1140 |
| cgtcgtcccg cccaccgccg gcctgcacga gccggacccg cagctggacc tggactacgt | 1200 |
| cccccctgatc gcccgggacc aggccaccga caccgtcctg accgtgggct ccggcttcgg | 1260 |
| cggcttccag tccgcgatgg tcctgacctc ggccgagggc ggccggtcct gatactagta | 1320 |
| gcggccgctg cag | 1333 |

<210> SEQ ID NO 21
<211> LENGTH: 1285
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21

| | |
|---|---|
| gaattcgcgg ccgcttctag agaaagagga gaaatactag atgtccgccg ccaccgtggt | 60 |
| caccggcatc ggcgtcctgg ccccgaacgg catcggcgcc gaggagttct gggccgccac | 120 |
| cctgcgggcc gagtccggca tcggccggat caccccacttc gagcccgcct cctacccctc | 180 |
| ccggctggcc ggcgaggtca ccggcttctc cgcccgcgag cacctgccct ccggctggt | 240 |
| cccgcagacc gaccggacca cccagttcgc cctgaccggc tccgagtggg ccctgcggga | 300 |
| ctccggcctg tccgccgaca ccctgccggc cggtgagcgc ggcgtcgtca ccgcctccgc | 360 |
| ctccggcggc ttcgagttcg gccagcggga gctgggccac ctgtggggca aggacccgcg | 420 |
| ccacgtctcc gcctacatgt ccttcgcctg gttctacgcc gtcaactccg gccagatcag | 480 |
| catccgccac gacctgcggg gcccgaccgg cgtcctggtc accgaccagg ccggcggcct | 540 |

| | |
|---|---|
| ggacgccgtg gcccaggccc gccggcgcat ccgcaagggc accccggtca tgctgtccgg | 600 |
| cggcatggac gcctccctgt gcccgtacgg cctggtcgcc cagatcagcg ccggcatgct | 660 |
| gtccgagtcc gacgacccca cccgcgccta ccggccgttc gaccccgccg ccgacggcca | 720 |
| cgtcccgggc gagggcggcg ccatcctgac cctggaggac ggcgaccgcg cccgcgcccg | 780 |
| cggtgcccgg tcccacggcg agatcagcgg ctacgccgcc accttcgacc cgcgcccggg | 840 |
| ctccggccgg cccgccaacc tggaccgcgc atccgcggt gccctggccg acgcggcct | 900 |
| gtccccgcgc gacatcgcct tcgtcctggc cgacggcgcc ggcgagcccg agccggaccg | 960 |
| cgccgaggcc cgtgccctga ccgacgtctt cggcccgcgc ggcgtccccg tcaccgtccc | 1020 |
| gaagtccatg accggccggc tgtacgccgg cgccgccccg ctggacctgg tcaccgccct | 1080 |
| gttcgccctg cgggacggcg tcgtcccgcc caccgtccac gtggacgagc cggaccccgc | 1140 |
| ctacgacatc gacctggtca ccggctccgc ccgcccgtc cggggcgacg ccgccctggt | 1200 |
| cctggccccgc ggccgggggcg gcttcaactc cgcgatggtc gtccgtcgcc cgccggccgc | 1260 |
| ctgatactag tagcggccgc tgcag | 1285 |

<210> SEQ ID NO 22
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

| | |
|---|---|
| gaattcgcgg ccgcttctag agaaagagga gaaatactag atgtccgcct tcaccgtcga | 60 |
| ggagctgttc cagatcatgc gcgagtgcgc cggcgaggaa gaggccgtgg acctggccga | 120 |
| cgccgccgag caggagttcg ccctgctggg ctacgactcc ctggccctga tggaggccat | 180 |
| ctcccgcgtc gagcggggcc tgggcatcgc cctgccggag gagaccgtgg gcgaggtcct | 240 |
| gaccccggcc gccttcgtgg acgtggtcaa cgccgagctg gcccggtccg ccccggtcgt | 300 |
| cgaggccgcc ggttgatact agtagcggcc gctgcag | 337 |

<210> SEQ ID NO 23
<211> LENGTH: 1171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

| | |
|---|---|
| gaattcgcgg ccgcttctag agaaagagga gaaatactag atgaccgagg agcacctgga | 60 |
| cccggccggc ggcgccccgc tggcccaggc cccggcccag gacatccgca tcgccggctg | 120 |
| cgccgtctgg ctgccgcccc gggcccccgt cgcccaggcc gtcgccgccg gtctgtgcga | 180 |
| cgaggccctg gccaccgcca ccgcgatggt ctccgtcgcc gtcgcccagg acgagccggc | 240 |
| ccccgagatg gccgcccgtg ccgcccgcac cgccctggcc cgcggcggct ccgacgacgt | 300 |
| ctccctgatc ctgcacgcct ccttcttcta ccagggccac gacctgtggg ccccgcctc | 360 |
| ctacgtccag cgcgtggccg tgggcaacca ctgcccggcc atcgaggtgg ccaggtctc | 420 |
| caacggtggc atggccgccc tgggcctggc cgtggaccac ctgtccgccg gcgccggc | 480 |
| cggcgccgcc ggtcgccgcg tcctggtcac caccggcgac gccttccgtc cgccgggctt | 540 |
| cgaccgctgg cggtccgacc ccggcacctt ctacggcgac ggcggcaccg ccctggtcct | 600 |

| | |
|---|---|
| gtcctcccag gaaggcttcg cccgcatccg gggcctggcc accgtctccg ccccgagct | 660 |
| ggagggcatg caccgcggcg acgaccctt cggctccgcc ccgttctccc accgccggt | 720 |
| ggtggacctg gaggcctgca agaaggactt cctggcctcc cgccgggtca cccaggtcat | 780 |
| cgccgcctcc gccgccgccc aggacgccgc cctgggccag gccctggccg ccgccggtgc | 840 |
| cgagctggcc gacatcgacc gcttcgtcct gccgcacatg ggccgcaagc ggctgcgcgc | 900 |
| cggcttcctg aaccgcctgg catcggcga ggaccgcacc acctgggagt ggtcccgggg | 960 |
| cgtcggccac ctgggcgccg cgaccagat cgccggcttc gaccacctgg tgggctccgg | 1020 |
| ctccctgggc cccggcgacc tggtcctgtg gatgtccgtg ggcgccggct tcacctactc | 1080 |
| ctgcgccgtc gtcgagatgc tggagcgccc cggctgggcc gccacgccg gcaccgccgg | 1140 |
| cgccgcctga tactagtagc ggccgctgca g | 1171 |

<210> SEQ ID NO 24
<211> LENGTH: 1105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

| | |
|---|---|
| gaattcgcgg ccgcttctag agaaagagga gaaatactag atgaccggca ccgccggcgc | 60 |
| cctgcccgtg gccctgctgc tgcccggcca gggctcccag caccgtcgca tggccgccgg | 120 |
| tctgtacggc cacgagcccg tcttcaccga ggcgatggac gagttcttcg acgccgccgg | 180 |
| tcccgagggc gacccgctgc gcgacgactg gctggccgag cggcccgtca ccgacatcga | 240 |
| ccacgtcacc cgctcccagc ccctgctgtt cgccgtggac cacgccctgg gccggctggt | 300 |
| cctgggccgc ggcgtccggc cggccgcact gctgggccac tccatcggcg agctggccgc | 360 |
| cgcaaccctg gccggcgtct cgccccgcg cgacgccgcc ggcctggtcc tggaccggat | 420 |
| ccgccggctg tccgccgccc cgcccggcgg catgctggcc gtcgccgcct ccaccgccga | 480 |
| ggtcgccccc tacctgcgcg cgacgtcgt cgtcggcgcg gtcaacgccc cgcgtcagac | 540 |
| cgtcctggcc ggcccggacg gccccctgga cgaggtggac cgcgccctgc gggaggccgg | 600 |
| cttcgtctgc cgccgggtcc cctccctgtc cgccttccac tccccgtcc tggagccggc | 660 |
| ctgccgcggc gccgccccgc tgttcgccgc cgcatgcaag cacccgcccg ccgtcccggt | 720 |
| ccactccgcc tacaccgccg ccccgctgac cgagtccgac atcgacgacc cggccttctg | 780 |
| ggcccgccag ccggtcgccc ccgtcctgtt ctggccggcc ctggagggcc tgctggccac | 840 |
| cggcgaccac ctgctggtcg aggtcggccc cggccagggc ctgtcccagc tggtccgccg | 900 |
| gcacccggcc gtccgccggg gcggctccgc cgtcgtctcc ctgctgcccg cccgccccgg | 960 |
| tccgccggag ccgaccggg ccgcgtcgc cgccgcaacc gagcagatca ccgccgccgg | 1020 |
| ccgccaggcc gccccggcct ccgccgacca cggccgcccc tcccggcagg ccgccgccgg | 1080 |
| ttgatactag tagcggccgc tgcag | 1105 |

<210> SEQ ID NO 25
<211> LENGTH: 847
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
gaattcgcgg ccgcttctag agaaagagga gaaatactag atgtccgagg ccgccgaccg      60
ggtggccctg gtcaccggcg gcacctcggg catcggcctg gccgtcgtcc ggaagctggc     120
ccaggacggc acccgcgtct tcctgtgcgc ccgggacgag tccgccatca ccggcaccgt     180
caaggagctc caggcctccg gcctggaagt ggacggcgcc cctgcgacg tccgctccac      240
cgccgacgtg gaccggctgg tccagaccgc ccgcaaccgg ttcggcccca tcgacatcgt     300
cgtcaacaac gccggccgcg gcggcggcgg cgtcaccgcc gagatcaccg acgacctgtg     360
gctggacgtc gtggacacca acctgtccgg cgccttccgg gtcacccggg ccgtcctgac     420
cggcggcgcc atgcaggagc acggctgggg ccggatcatc tccatcgcct ccaccggcgg     480
caagcagggc gtcgccctgg cgcccccgta ctccgcctcc aagtccggcc tgatcggctt     540
caccaaggcc gtggccctgg agctggccaa gaccggcatc accgtcaacg ccgtctgccc     600
cggctacgtg gagaccccga tggcccaggg cgtccgccag cggtacgccg ccttctgggg     660
catcaccgag gacgacgtcc tggagaagtt ccaggccaag atcccctgg gccgctactc      720
catgccggag gaagtcgccg gcatggtcca ctacctggcc tccgactccg ccgactccat     780
caccgcccag gccatcaacg tctgcggcgg cctgggctcc tactgatact agtagcggcc     840
gctgcag                                                               847
```

<210> SEQ ID NO 26
<211> LENGTH: 1009
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
gaattcgcgg ccgcttctag agaaagagga gaaatactag atgtccgagc tgcccctcca      60
gcagaccgag cacgagatcc acacctcggc cgccccggac gccgtcttcg ccgtcctggc     120
cgacgcccgt gcctggccgg ccgtcttccc gccctccgtc cacgtggagc aggtggagca     180
caccggctcc tccgagcgca tccggatctg gccaccgcg aacggctccc tgcgcacctg      240
gacctcgcgc cgcgagctgg acgagcgggc ccgccggatc cgcttccggc aggaagtctc     300
cgcccacccg gtggccgcga tgggcggcga gtggatcgtg gaggaagccg cgacggcgg      360
cacccgcgtc cggctgaccc acgacttccg ggccgtggac gacgacccg agaccatcgg      420
ctggatccac cgggccgtgg accggaactc cgaggccgag ctggcctccc tgcgcaccgc     480
cctggagcgg cccgacggca ccgcccccac caccttcgag gacaccgtgg tggtccgcgg     540
tcgcgccgag gacgtctacg acttcctgca ccggtccgac ctgtggaaga gcgcctgtc      600
ccacgtggcc cggatcgccg tcaaggaaga ggagcccggc ctccagcaca tggagatgga     660
cacccctgacc gccgacggct ccgtccacac caccgcctcc gtccgggtct gcttccccga    720
gcgtcgcgtc atcgtctaca gcagctgcg gaccccgccc ctgctggccc tgcacctggg     780
ccgctggtcc gtccggcccg ccgacgacg cgacggcatc gccgtcacct cggcccacac     840
cgtctccgtc gcccgctccg ccatcccggg cgtcctgggc gccggcgcct ccgagaccga     900
cgccgtggac ttcgtccgtc gcgccctggg ccgcaactcc ctgctgaccc tggaggccgc     960
ccggcagtac gccgagtcct ccgcctgata ctagtagcgg ccgctgcag              1009
```

<210> SEQ ID NO 27

<211> LENGTH: 841
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
gaattcgcgg ccgcttctag agaaagagga gaaatactag atgcgcatca tcgacatctc      60
ctccgccgtg gacgcctccg gctgggagcc cgacgaggtg cggcacgagg tccactcccc     120
gcgggagggc gccgtccaca tgtccgagga gatgcgccgg cacttcggcg tggccttcga     180
ccccgacgag ctgccggagg cgagttcct gtccctggac cggctgaccc tgacctcgca      240
caccggcacc cacatcgacg cccccctccca ctacggctcc cgggcccact acggcgacgg     300
tcgcccgcgc aacatcgacg agctgcccct ggactggttc tacggccccg gctgctgct      360
ggacctgacc ggctgcgacg gccccaccgc cggcgccggc gacctggaga aggagctggc     420
ccgcatcggc cgggtcccgg agcccggcac catcgtcctg ctgcgcaccg cgcctccga     480
gcgggccggc accgagcagt acttcaccga cttcaccggc ctggacggcc cggccgtcaa     540
cctgctgctg gaccacggcg tccgggtcat cggcaccgac gccttctccc tggacgcccc     600
cttcggcgcc gtcatccgcc gctaccgcga gaccggcgac cggtccgtcc tgtggcccgc     660
ccacgtcacc ggccgccacc gggagtactg ccagatcgag cggctgggca acctggccgc     720
cctgcccggc tgcgacggct tccaggtggc ctgcttcccc gtcaagatca ccggcggcgg     780
cgccggctgg acccgggccg tcgccttcgt ggacgagtga tactagtagc ggccgctgca     840
g                                                                      841
```

<210> SEQ ID NO 28
<211> LENGTH: 451
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
gaattcgcgg ccgcttctag agaaagagga gaaatactag atgccccagc cggagcccaa      60
cgacgccggc tccggctccg tcaccttcgt caaccgcttc accctgtccg gctccgccga     120
ggacttcgag gccgccttcg ccgagaccgc cgagttcctg tgccgccggc ccggcttccg     180
ctggcacgcc ctgctggtcc ccgccgacac cggcccggc tccgccgacg cccgcccgca      240
gtacgtcaac atcgccgtct gggacgacga ggcctccttc cgggccgccg tcgcccaccc     300
cgagttcccc gccacgccg ccgcactgcg ggccctgtcc acctcggagc cgaccctgta      360
ccgccaccgg cagatccgcg tcgccccga cgtcccggcc gtctccggcc cgggtggccg     420
caccacctga tactagtagc ggccgctgca g                                    451
```

<210> SEQ ID NO 29
<211> LENGTH: 922
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
gaattcgcgg ccgcttctag agaaagagga gaaatactag atgcaggact cctcctacaa      60
```

| | |
|---|---|
| ggagcaggtc acccaggcct tcgaccagtc ctcctccacc tacgaccgcc tgggcgtcga | 120 |
| gttcttcacc ccgatgggcc gcccgctggt cgagatcagc gagcccgtca ccggcgagcg | 180 |
| ggtcctggac atcggctgcg gccggggcgc ctgcctgttc ccggccgccg agaaggtcgg | 240 |
| cccccagggc gcgtccacg gcatcgacat cgccccggc atgatcgagg aagcccgcaa | 300 |
| ggaagccgcc gagcgcggcc tgcggaacat cgccctggac gtcatggacg ccgagacccc | 360 |
| ggagctgccg gcccgctcct tcgacctggt catgggctcc tactccgtca tcttcctgcc | 420 |
| cgacgccgtg ggcgccctgg cccggtacgc cggcatcctg gaccacggcg ccggatcgc | 480 |
| cttcacctcg cccgtcttcc gcgccggcac cttccccttc ctgccgcccg agttcacccc | 540 |
| gctgatcccg caggccctgc tggagcacct gccggagcag tggcgcccgg aggccctggt | 600 |
| ccgccggttc aactcctggc tggagcgggc cgaggacctg ctgcggaccc tggagcgctg | 660 |
| cggctacacc tcggtcgccg tcaccgacga gcccgtgcgg atgaccgccc tgtcctccga | 720 |
| ggcctgggtg gactggtccc acacccaggg catgcggctg ctgtggcaga acctgcccca | 780 |
| ggcccagcgg accgagctgc gcgcccggct ggtcgagggc ctggacaagc tgtccgacgc | 840 |
| caccggcgcc ctggccatcg acgtcccggt ccgcttcgtc accgcccggg tcgcccactg | 900 |
| atactagtag cggccgctgc ag | 922 |

<210> SEQ ID NO 30
<211> LENGTH: 499
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

| | |
|---|---|
| gaattcgcgg ccgcttctag agaaagagga gaaatactag atgtccaccc agatcgacct | 60 |
| ggtccgtcgc atggtcgagg cctacaacac cggcaagacc gacgacgtcg ccagttcat | 120 |
| ccacctggag tacctgaacc ccggcgccct ggagcacaac cccgagctgc ggggccccga | 180 |
| ggccttcgcc gccgccgtca cctggctgaa gtacgcctt ccgaggaag cccacctgga | 240 |
| ggagatcgag tacgaggaga cggcccctg ggtccggggc aagctggccc tgtacggccg | 300 |
| gcacgtgggc aacctggtgg gcatgcccgc caccggccgc cggttctccg gcgagcagat | 360 |
| ccacctgatc cggatcgtgg acggcaagat ccggaccac cggactggc cggactacct | 420 |
| gggcacctac cgccagctgg gcgagccgtg gcccaccccg gagggctggc ggccgtgata | 480 |
| ctagtagcgg ccgctgcag | 499 |

<210> SEQ ID NO 31
<211> LENGTH: 1531
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

| | |
|---|---|
| gaattcgcgg ccgcttctag agaaagagga gaaatactag atggccctga ccaagccgga | 60 |
| cgtcgatgtc ctggtcgtcg gcggcggcct gggcggcctg tccaccgccc tgttcctggc | 120 |
| ccgccggggc gccgcgtcc tgctggtcga gcgccacgcc tccacctccg tcctgccgaa | 180 |
| ggccgccggc cagaacccgc ggacgatgga gctgttccgc ttcggcggcg tcgccgacga | 240 |
| gatcctggcc accgacgaca tccgcggcgc ccagggcgac ttcaccatca aggtcgtcga | 300 |

```
gcgcgtcggc ggccgggtcc tgcactcctt cgccgagtcc ttcgaggagc tggtcggcgc    360
caccgagcag tgcaccccga tgccctgggc cctggccccg caggaccgcg tcgagccggt    420
cctggtcgcc cacgccgcca agcacggcgc cgagatccgc ttcgccaccg agctgacctc    480
cttccaggcc ggcgacgacg cgtcaccgc ccggctgcgg gacctgggca ccggcgccga    540
gtccaccgtc tccgcccgct acctggtcgc cgccgacggc ccgcggtccg ccatccgcga    600
gtccctgggc atcacccggc acggccacgg caccctggcc cacttcatgg gcgtcatctt    660
cgaggccgac ctgaccgccg tcgtcccgcc cggctccacc ggctggtact acctgcaaca    720
cccggacttc accggcacct tcggcccac cgaccggccg aaccgccaca ccttctacgt    780
cgccaccacc ccggagcgcg gcgagcggcc ggaggactac accccgcagc gctgcaccga    840
gctgatccgc ctggccgtcg atgccccggg cctggtcccg gacatcctgg acatccaggc    900
ctgggacatg gccgcctaca tcgccgaccg gtggcgcgag ggcccggtcc tgctggtcgg    960
cgacgccgcc aaggtcaccc cgcccaccgg cggcatgggc ggcaacaccg ccatcggcga   1020
cggcttcgac gtcgcctgga agctggccgc cgtcctgcgc ggcgaggccg cgagcgcct   1080 gctggactcc tacggcgccg agcggtccct ggtctcccgg ctggtcgtcg atgagtccct   1140
ggccatctac gcccagcgca tgccccaca cctgctgggc tccgtcccgg aggagcgcgg   1200
caccgcccag gtcgtcctgg gcttccgcta ccggtccacc gccgtcgccg ccgaggacga   1260
cgaccccgag ccgaccgagg acccgcggcg cccgtccggc cgcccgggct tccgggcccc   1320
gcacgtctgg atcgagcagg acggcacccg ccggtccacc gtcgagctgt tcggcgactg   1380
ctgggtcctg ctggccgccc cggagggcgg cgcctggccg ggccgcccgc ccgccccgcc   1440
ccgcatctgg gcctccgcct ccacctccat ctcctccgcc gccatgtccc cgccgccccc   1500
agccaactga tactagtagc ggccgctgca g                                    1531
```

<210> SEQ ID NO 32
<211> LENGTH: 466
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gaattcgcgg ccgcttctag agaaagagga gaaatactag atggtgtccg ccttcaacac     60
cggccgcacc gacgacgtcg acgagtacat ccacccggac tacctgaacc cggccacccct    120 ggagcacggc atccacaccg gccccaaggc cttcgcccag ctggtcggct gggtccgggc    180
caccttctcc gaggaagccc gcctggagga agtccggatc gaggagcggg gcccctgggt    240
caaggcctac ctggtcctgt acggccgcca cgtgggccg ctggtcggca tgcctccgac    300
cgaccgccgg ttctccggcg agcaggtcca cctgatgcgg atcgtcgacg caagatccg    360 cgaccaccgg gactggcccg acttccaggg caccctgcgc cagctgggcg acccgtggcc    420
cgacgacgag ggctggcggc cctgatacta gtagcggccg ctgcag                    466
```

<210> SEQ ID NO 33
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
gaattcgcgg ccgcttctag agggtaccag cccgacccga gcacgcgccg gcacgcctgg      60
tcgatgtcgg accggagttc gaggtacgcg gcttgcaggt ccaggaaggg gacgtccatg     120
cgagtgtccg ttcgagtggc ggcttgcgcc cgatgctagt cgcggttgat cggcgatcgc     180
aggtgcacgc ggtcgatctt gacggctggc gagaggtgcg gggaggatct gaccgacgcg     240
gtccacacgt ggcaccgcga tgctgttgtg ggcacaatcg tgccggttgg taggatccta     300
ctagtagcgg ccgctgcag                                                  319
```

<210> SEQ ID NO 34
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
gaattcgcgg ccgcttctag aggctgctcc ttcggtcgga cgtgcgtcta cgggcacctt      60
accgcagccg tcggctgtgc gacacggacg gatcgggcga actggccgat gctgggagaa     120
gcgcgctgct gtacggcgcg caccgggtgc ggagcccctc ggcgagcggt gtgaaacttc     180
tgtgaatggc ctgttcggtt gcttttttta tacggctgcc agataaggct tgcagcatct     240
gggcggctac cgctatgatc ggggcgttcc tgcaattctt agtgcgagta tctgaaaggg     300
gatacgctac tagtagcggc cgctgcag                                        328
```

<210> SEQ ID NO 35
<211> LENGTH: 462
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
gaattcgcgg ccgcttctag agcccgccgc gggcgctgga ggctcgggcg ggccccgggc      60
cggaggcggc cgcgaccacg acgcccgcgg gacgtgacga gcggcacgac tcgacgactc     120
cgggctcctt tgacgctgtc cgtcgcgccg ggtagcgtag gacaccgtgc ccgcgccgtc     180
gggccctcgc gcgtgcactc ggtcgaccgc tccctgccgg agtgggtgcg ggtgcacggg     240
gtggctcccc acctcctctc ggatcggtcc tcgcggactg ccgccgtgcg gaggaccggg     300
gcgacacgcc cgggcgcggg ggtcggtgcg ggactccaga cctccggggt agtcgtgcga     360
cgggcgacga tccggccga gccggccgtc ctgggtgacg ggtgccggtc agaccagaga     420
acaccgacag acggagacgt atactagtag cggccgctgc ag                       462
```

<210> SEQ ID NO 36
<211> LENGTH: 548
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
gaattcgcgg ccgcttctag agtccgcgcc gccggcccga cggtgcccgg ccccgtaccc      60
cccccgggtg gtgcggggcc gggcaccggc cttttggcgc tgcggagttg acggaagttg     120
```

-continued

```
gccgaaccgg atgcgctcgg cgcccggggg ctgaaagatg ctcacagccc ctttccacgg      180
cggtccggga gggaggccgg ggcaaccggt tttcggggc ggagtgtccg gtatgcggac       240
ggccgcgccc gatagatgtg taacgagtcc gtttcgcaac catctatctc ggatcggttt     300
gtccggattt tggaagatgt gagtgtcagg tgtgatcgaa ccgagaccaa aagggtgtgg     360
tcgggccgaa caccatggct aatagttgag cgcgtagagc tcgggtcaat gggtcacgcg     420
ctgtggggag cgccgactca cgagcacact ggggcactcg atcttcgccg tcagggtgt      480 cggcggatcg tcctgtgccc tctcttgcag tgaacaagtg gactcattac tagtagcggc     540
cgctgcag                                                              548
```

<210> SEQ ID NO 37
<211> LENGTH: 149
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
atgaattcgc ggccgcttct agagtgttca cattcgaacg gtctctgctt tgacaacatg       60
ctgtgcggtg ttgtaaagtc gtggccagga gaatacgaca gcgtgcagga ctggggagt       120 gcgcattact agtagcggcc gctgcagta                                        149
```

<210> SEQ ID NO 38
<211> LENGTH: 3363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
gaattcccgg cgggctgcag tggcgccgga cggggcttca gacgtttcgg gtgctgggtt      60
gttgtctctg gacagtgatc catgggaaac tactcagcac caccaatgtt cccaaaagaa    120
agcgcaggtc agcgcccatg agccaagatc taggcatgtc gcccttcatc gctcccgacg    180
tccctgagca cctgctggac actgttcgcg tcttcctgta cgcgcgtcag tctaagggcc    240
ggtccgacgg ctcagacgtg tcgaccgaag cacagctagc ggccggtcgt gcgttggtcg    300
cgtctcgcaa cgcccagggg ggtgcgcgct gggtcgtggc aggtgagttc gtggacgtcg    360
ggcgctccgg ctgggacccg aacgtgaccc gtgccgactt cgagcgcatg atgggcgaag    420
tccgcgccgg cgaaggtgac gttgtcgttg tgaatgagct ttcccggctc actcgcaagg    480
gcgcccatga cgcgctcgaa atcgacaacg aattgaagaa gcacggcgtg cgcttcatgt    540
cggttcttga gccgttcctt gacacgtcta cccctatcgg cgtcgccatt ttcgcgctga    600
tcgctgccct tgcgaaacag gacagtgacc tgaaggcgga gcgcctgaag ggtgcgaaag    660
acgagattgc cgcgctgggt ggcgttcact cgtcttccgc cccgttcgga atgcgcgccg    720
tgcgcaagaa ggtcgataat ctcgtgatct ccgttcttga gccggacgaa gacaacccgg    780
atcacgtcga gctagttgag cgcatggcga aaatgtcgtt cgaaggcgtg tccgacaacg    840
ccattgcaac gaccttcgag aaggaaaaga tcccgtcgcc cggaatggct gagagacgcg    900
ccacggaaaa gcgtcttgcg tccgtcaagg cacgtcgcct gaacggcgct gaaaagccga    960
tcatgtggcg cgctcaaacg gtccgatgga ttctcaacca tccgcaatc ggcggtttcg   1020 cattcgagcg tgtgaagcac ggtaaggcgc acatcaacgt catacggcgc gaccccggcg   1080
```

```
gcaagccgct aacgccccac acgggcattc tcagcggctc gaagtggctt gagcttcaag      1140
agaagcgttc cgggaagaat ctcagcgacc ggaagcctgg ggccgaagtc gaaccgacgc      1200
ttctgagcgg gtggcgtttc ctggggtgcc gaatctgcgg cggctcaatg ggtcagtccc      1260
agggtggccg taagcgcaac ggcgaccttg ccgaaggcaa ttacatgtgc gccaacccga      1320
aggggcacgg cggcttgtcg gtcaagcgca gcgaactgga cgagttcgtt gcttcgaagg      1380
tgtgggcacg gctccgcaca gccgacatgg aagatgaaca cgatcaggca tggattgccg      1440
ccgctgcgga gcgcttcgcc cttcagcacg acctagcggg ggtggccgat gagcggcgcg      1500
aacaacaggc gcacctagac aacgtgcggc gctccatcaa ggaccttcag gcggaccgta      1560
agcccggtct gtacgtcggg cgtgaagagc tggaaacgtg gcgctcaacg gtgctgcaat      1620
accggtccta cgaagcggag tgcacgaccc gactcgctga gcttgacgag aagatgaacg      1680
gcagcacccg cgttccgtct gagtggttca gcggcgaaga cccgacggcc aaggggggca      1740
tctgggcaag ctgggacgtg tacgagcgtc gggagttcct gagcttcttc cttgactccg      1800
tcatggtcga ccggggggcgc caccctgaga cgaagaaata catcccccctg aaggaccgtg    1860
tgacgctcaa gtgggcggag ctgctgaagg aggaagacga agcgagcgaa gccactgagc      1920
gggagcttgc ggcgctgtag cgcacagcgg gagggggtcga gccggcggac ggttcggccc     1980
cttttttggc cttgaaatcg ttagttaggc taacaagtag ttccttcgtc accacagcgg      2040
gcagggagca gtataggaac ttcgaagttc ccgccagcct cgcagagcag gattcccgtt      2100
gagcaccgcc aggtgcgaat aagggacagt gaagaaggaa cacccgctcg cgggtgggcc      2160
tacttcacct atcctgcccg gctgacgccg ttggatacac caaggaaagt ctacacgaac      2220
cctttggcaa aatcctgtat atcgtgcgaa aaaggatgga tataccgaaa aaatcgctat      2280
aatgaccccg aagcagggtt atgcagcgga aaatgcagct cacggtaact gatgccgtat      2340
ttgcagtacc agcgtacggc ccacagaatg atgtcacgct gaaaatgccg gcctttgaat      2400
gggttcatgt gcagctccat cagcaaaagg ggatgataag tttatcacca ccgactattt      2460
gcaacagtgc cgttgatcgt gctatgatcg actgatgtca tcagcggtgg agtgcaatgt      2520
catgattgaa caagatggat tgcacgcagg ttctccggcc gcttgggtgg agaggctatt      2580
cggctatgac tgggcacaac agacaatcgg ctgctctgat gccgccgtgt tccggctgtc      2640
agcgcagggg cgcccggttc ttttttgtcaa gaccgacctg tccggtgccc tgaatgaact      2700
ccaggacgag gcagcgcggc tatcgtggct ggccacgacg ggcgttcctt gcgcagctgt      2760
gctcgacgtt gtcactgaag cgggaaggga ctggctgcta ttgggcgaag tgccggggca      2820
ggatctcctg tcatctcacc ttgctcctgc cgagaaagta ccatcatgg ctgatgcaat      2880
gcggcggctg catacgcttg atccggctac ctgcccattc gaccaccaag cgaaacatcg      2940
catcgagcga gcacgtactc ggatggaagc cggtcttgtc gatcaggatg atctggacga      3000
agagcatcag ggctcgcgc cagccgaact gttcgccagg ctcaaggcgc gcatgcccga      3060
cggcgaggat ctcgtcgtga cccatggcga tgcctgcttg ccgaatatca tggtggaaaa      3120
tggccgcttt tctggattca tcgactgtgg ccggctgggt gtggcggacc gctatcagga      3180
catagcgttg gctacccgtg atattgctga agagcttggc ggcgaatggg ctgaccgctt      3240
cctcgtgctt tacggtatcg ccgctcccga ttcgcagcgc atcgccttct atcgccttct      3300
tgacgagttc ttctgagatg ccgctcgcca gtcgattggc tgagctcatg aagttcctat      3360
tcc                                                                    3363
```

<210> SEQ ID NO 39
<211> LENGTH: 3165
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

| | | | | | |
|---|---|---|---|---|---|
| gaattcccgg | ccggctgcag | gtgtaggctg | gagctgcttg | gaataggaac | ttcatgagct | 60 |
| cagccaatcg | actggcgagc | ggcatcttat | ttgccgacta | ccttggtgat | ctcgcctttc | 120 |
| acgtagtgga | caaattcttc | caactgatct | gcgcgcgagg | ccaagcgatc | ttcttcttgt | 180 |
| ccaagataag | cctgtctagc | ttcaagtatg | acgggctgat | actgggccgg | caggcgctcc | 240 |
| attgcccagt | cggcagcgac | atccttcggc | gcgattttgc | cggttactgc | gctgtaccaa | 300 |
| atgcgggaca | acgtaagcac | tacatttcgc | tcatcgccag | cccagtcggg | cggcgagttc | 360 |
| catagcgtta | aggtttcatt | tagcgcctca | aatagatcct | gttcaggaac | cggatcaaag | 420 |
| agttcctccg | ccgctggacc | taccaaggca | acgctatgtt | ctcttgcttt | tgtcagcaag | 480 |
| atagccagat | caatgtcgat | cgtggctggc | tcgaagatac | ctgcaagaat | gtcattgcgc | 540 |
| tgccattctc | caaattgcag | ttcgcgctta | gctggataac | gccacggaat | gatgtcgtcg | 600 |
| tgcacaacaa | tggtgacttc | tacagcgcgg | agaatctcgc | tctctccagg | ggaagccgaa | 660 |
| gtttccaaaa | ggtcgttgat | caaagctcgc | cgcgttgttt | catcaagcct | tacggtcacc | 720 |
| gtaaccagca | aatcaatatc | actgtgtggc | ttcaggccgc | catccactgc | ggagccgtac | 780 |
| aaatgtacgg | ccagcaacgt | cggttcgaga | tggcgctcga | tgacgccaac | tacctctgat | 840 |
| agttgagtcg | atacttcggc | gatcaccgct | tccctcatga | cattgcactc | caccgctgat | 900 |
| gacatcagtc | gatcatagca | cgatcaacgg | cactgttgca | aatagtcggt | ggtgataaac | 960 |
| ttatcatccc | cttttgctga | tggagctgca | catgaaccca | ttcaaaggcc | ggcattttca | 1020 |
| gcgtgacatc | attctgtggg | ccgtacgctg | gtactgcaaa | tacggcatca | gttaccgtga | 1080 |
| gctgcatttt | ccgctgcata | accctgcttc | ggggtcatta | tagcgatttt | ttcggtatat | 1140 |
| ccatcctttt | tcgcacgata | tacaggattt | tgccaaaggg | ttcgtgtaga | ctttccttgg | 1200 |
| tgtatccaac | ggcgtcagcc | gggcaggata | ggtgaagtag | gcccacccgc | gagcgggtgt | 1260 |
| tccttcttca | ctgtcccctta | ttcgcacctg | gcggtgctca | acgggaatcc | tgctctgcga | 1320 |
| ggctggcggg | aacttcgaac | tccaggtcga | cggatccccg | gatcgcgctc | gatgtggtc | 1380 |
| ctttagatcc | actgacgtgg | gtcagtgtct | ctaaaggact | cgcgagcatc | gttcccctc | 1440 |
| tccctgcact | gaggtgcggt | tttcagaggg | tggcagcagg | cggagaaaca | atcaagcgcg | 1500 |
| cctgcatggt | ttgcgctcca | gcggtcaaga | ccaggggtcg | ggctcccaca | cgggatgaaa | 1560 |
| ctcgaagctg | cgcacgacac | tccactgtgc | gccctgatcg | ctcttacggt | tgtggatgac | 1620 |
| cagacggcgc | agcaggcggc | gcaggatggc | gttcttctcg | gtggtgtgca | ggatgtccca | 1680 |
| ctcctgcaag | agcccgacga | tcaggggcg | gaactcctcc | cgcgtgggcg | cgacttcaac | 1740 |
| ctcgctgagc | gacttcaagt | gcttgatgat | gtcgcccttc | ttaccgagta | gctggtcgcg | 1800 |
| tacgcgcccg | aacgtgtccg | ccgggtactt | gtccgggtcc | agcgcgtaat | ccgtgacgag | 1860 |
| acggtcgagt | gcaccctcga | tcttggccaa | ctcggcttcc | gtgcgggtgc | gctcctcgac | 1920 |
| caggcgggcc | cgcgggtccg | gcgcggtgcc | cggcgcggtg | cgctgagcgg | gaagggccgg | 1980 |
| cgcgttgtcg | atgtcgtcgg | cgaccgtgtc | ggcgagccac | ttcaacacct | cggcctcgac | 2040 |

```
ttcgtcgcgg cgcacgtaga ggccgggctc acaggccgac ttccccttgt tcctgcggtt    2100
gaagcacacg aacacgtggc ccggaacgaa tccgcccttc ccgtcgcggc cggatcgcgc    2160
aacggccgtc ccgcggcagt gtccgtgccg catgatgccg ctggtcgggt atgaggcccg    2220
gcgggcgcgc gggggcgtct tgcgcgtctg ctctctgtgc gccccgtact ccttccactg    2280
ctcgggaacg atgagcgccg gctgtgcccc ggggagccag agccaccggt tttctttgca    2340
cgcagagaag tggtcctgtc ccagcttgca ccggcactcc gggtcgtgga cgcgtagcag    2400
gccggcggcg aatccggagt cgaggtagcg ctgaacggtg ttggtgcccc agcggttgcc    2460
ccgtgtggtg gggatgagta gttcgtcgtt cagccagtag gcgagctggg agaaccctg     2520 tccggcgagc tttcgctcgt agagttcggc cgccacgggg gcgaactctg ggtgccgttc    2580
gtagcgctcc tcttgcaggc ggaacccgcc cggcgcggtg aggtcgggta cgcgcctcgg    2640
gtgccacacg tagccgaacc gctgacgccc ggtggcgggg agtttcaggg cccgacggtg    2700
ggcgtgcgtc tccttccact gttcgccggc ccgatccgac tcgaatacgg cgaggtcgaa    2760
cagaatcgcg cggttgaagc gtccgacggc cgtgcgggcg tcgacttctt ccgtggcgga    2820
cgcgaggtct ccgccggcct gttcgaggcg ggcgaggttg atagcgatgc ccaggtcgtt    2880
ccggccgaag cggctgaact tccatacggc gattccgacg gcctcgcggc cctcgacgcg    2940
ctggatgccg cccatgatct tccgcttgaa gttgcggccc gtagcgtcga ggtcaacgat    3000
ccagtcgacg atccgacgtc ccgttcgggc ggcccatgac tcgatcgcgg attgctgtag    3060
ctccgggctg atcttctcct cgcgccatgt gctgaccctg atgtagccga gccacggctc    3120
gcccggcgtg cgggagccgc ggaacgtgct tggtaggtct cgttt                    3165
```

<210> SEQ ID NO 40
<211> LENGTH: 3517
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
gaattcccgg ccggctgcag gtgtaggctg gagctgcttc ggaataggaa cttcatgagc      60
tcagccaatc gactggcgag cggcatccta ccggtagccg ctgaggccgt cggcgagttc     120
ctcctcgtcg ccgtcgcgct gcgcgtagag ggcctgctgg agtgcgaagg tgcctcggat     180
cgccgagatc cgctcggccg ttccgttgtc ggcccagccg ccgagcgcga gcactcggcc     240
cagcagttcc tcgccgtagc tcgccccgat ggcggccagg tcctcagccg ggtcgccgat     300
gccgacctcg tcccagtcga cgacgccgct catgcgcggc actccgtcca ccgtctccca     360
caggacgttc tcgccgccga ggtcaccgtg gaccaccgcg gaggtgagat ggggcagggc     420
gtcgagcgcg gcgagctcgc gctcggcacg ctcccggccg ccgtcggaca tcagcgggaa     480
cagttcggta cgcaccccg tggcgaactc ctgccactgt tcgcgggag cctccggcag      540 cgcggcgcgc accttctcct cgtcgcccgc cgccgcgagc ccggacagca gggtcgcgta     600
ctgtcgggcg acggcctccg ccacctccgg gctggtgagc acatcgtcct caacggtgc     660 tccgggaatg cggctcagca ccaggtacgg cggctcgtcc gtgccctggg cgccgccctc     720
ggacagcggc tgcggcgtgc gaaacccgag gtcgatcccg gcaagagcgc gcaggacgtc     780
cgccctgccg ggcagacggt cggcggccgc ccgggtgcgg gcgaagcaga ccacccggtg     840
cgatccgatc accacatggt ggaactgccc ctcgtggacg gcgagtccgc ccacggtgtc     900
```

```
cccgggcagg agccggctca gcagatcgcg gtgcgtctca atgattctca tgacattgca    960
ctccaccgct gatgacatca gtcgatcata gcacgatcaa cggcactgtt gcaaatagtc   1020
ggtggtgata aacttatcat cccctttgc tgatggagct gcacatgaac ccattcaaag    1080
gccggcattt tcagcgtgac atcattctgt gggccgtacg ctggtactgc aaatacggca   1140
tcagttaccg tgagctgcat tttccgctgc ataaccctgc ttcggggtca ttatagcgat   1200
tttttcggta tatccatcct ttttcgcacg atatacagga ttttgccaaa gggttcgtgt   1260
agactttcct tggtgtatcc aacggcgtca gccgggcagg ataggtgaag taggcccacc   1320
cgcgagcggg tgttccttct tcactgtccc ttattcgcac ctggcggtgc tcaacgggaa   1380
tcctgctctg cgaggctggc gggaacttcg aactccaggt cgacggatcc ccggaatgta   1440
agcgtcacgg cacgcgccga ctgagagacg tttccgcagg tcaacccgt tccagcccaa    1500
cagtgttagt ctttgctctt acccagttgg gcgggatagc ctgcccggca tgagcgtgaa   1560
ggttgaaggc atggtcattc tggcaggcg ctacgaccga cagtcggcgg aacgggagaa    1620
cagttcgacc gcttcaccgg ccacccagcg cgccgcgaac cggggaagg ctgaggcgct    1680
ggcgaaggag tacgcgcgcg acggcgtcga ggtgaagtgg ctgggtcact tcagcgaagc   1740
gcccggcacg tcggcattca cgggcgtcga ccggccggag ttcaaccgga ttttggacat   1800
gtgccggaac cgggaaatga acatgatcat tgttcattac atttcgcgcc tcagccgcga   1860
agagccgctg acattattc cggtcgtcac ggaattgctc cggctgggcg tgaccattgt    1920
cagcgtgaac gaaggcacat tccgccccgg cgaaatgatg gaccttattc acctgatcat   1980
gcgccttcag gcttcgcatg atgagtcgaa gaacaagagc gtcgccgtgt cgaacgctaa   2040
ggaattggcg aagcggctgg gcggacacac ggggtcgacg ccgtacggat cgacacggt    2100
cgaggaaatg gttccgaacc cggaagacg cggaaagctg gttgccattc gccgactggt    2160
gcccagcgcg cacacctggg aaggcgcaca cggcagcgaa ggggcggtaa tccgctgggc   2220
gtggcaggag atcaagacgc accgcgatac gccattcaag ggtggcggag ccgggtcgtt   2280
tcaccctggg tcgctgaacg ggctttgtga gcggctgtac cgcgacaagg tgcctacgcg   2340
cggcacgctg tcggtaaga agcgcgccgg ttccgattgg gaccccggcg tttttgaagcg   2400
cgtactcagc gacccgcgca ttgccgggta tcaagctgac atcgcataca aggtgcgcgc   2460
cgacggttcg cggggcggct tcagccatta caagatcagg cgcgacccgg tcaccatgga   2520
gccgctgacc ctgcccggct tcgagccgta cattccccg gcggaatggt gggaacttca    2580
ggagtggctt cagggtcgag gacgcgggaa gggtcagtac cgggggcaat cgctcctgtc   2640
ggcaatggac gtcctttact gctacggctc cggccagctc gacccggaga cgggttacag   2700
caacgggtcg accatggcgg gcaacgtccg cgaaggtgat caagctcaca agtcgtcgta   2760
cgcgtgcaag tgcccccgcc gggttcatga cgggtcgtca tgctcgatca cgatgcacaa   2820
ccttgacccg tacatcgtcg gcgcgatctt cgcgcgcatc acggccttcg accctgccga   2880
ccctgacgac ctcgaaggcg acacggcagc gctcatgtac gaagccgcac ggcgctgggg   2940
agcgacgcac gaacgcccgg agttgaaggg tcagcgctcc gaactgatgg cacagcgcgc   3000
ggacgccgtg aagcgctcg aagagcttta cgaagacaag cggaacgcg ctaccggtc     3060
cgccatggga cggcgcgcgt tctcgaagaa ggaagccgcg ctgacgctcc gcatggaagg   3120
ggccgaagaa cggcttcgtc agctcgacgc cgccgactcc ccgtgctgc cgatcggcga    3180
atggctgggc gaccggggca gcgacccgac gggaccgggt tcgtggtggg cgctagcgcc   3240
ccttgaagac cgtcgggcgt tcgtccggct cttcgtggac cggatcgagg tgatcaagct   3300
```

```
tccgaagggc gttcagcggc ccggacgggt tcccccgatc gccgaccgtg tgcgtatcca    3360
ctgggcgaag ccgaaggtcg aggaagagac ggagccggag acgctgaacg ggttcacagc    3420
ggcggcgtga cggcggcacc agcgcaacgg gaaggggctt cggcccttt tctcgtgccc     3480 ggcgtcggtt cgttgcccta agcaactgtt cctagcg                             3517
```

GENETICALLY MODIFIED HOST ORGANISM FOR EXPRESSING AN ANTHRACYCLINONE ANALOGUE, METHOD ASSOCIATED THEREWITH, AND SYNTHETIC NUCLEIC ACIDS

CROSS-REFERENCE TO RELATED APPLICATION

The application claims the benefit of U.S. Provisional Application 62/524,244, filed Jun. 23, 2017, the disclosure of which is hereby incorporated by reference in its entirety.

SEQUENCE LISTING

The subject application contains a Sequence Listing which has been filed electronically in ASCII format and is hereby incorporated by reference in its entirety. Said ASCII copy, created on 31 Aug. 2018, is named 059206 174837-US SL.txt and is 56,980 bytes in size.

FIELD OF THE INVENTION

The present invention generally relates to a genetically modified host organism and, more specifically, to a genetically modified host organism for producing an anthracyclinone analogue, as well as related methods and synthetic nucleic acids associated therewith.

DESCRIPTION OF THE RELATED ART

Actinomycetes are gram positive, soil-dwelling microorganisms that produce a large number of natural product molecules with distinct biological activities. The actinomycetes, in particular the genus *Streptomyces*, are prolific producers of polyketides, which represent some of the most chemically diverse molecules produced in nature. Many polyketides exhibit important anticancer, antibiotic, and/or immunosuppressant activity, and include clinically-relevant examples such as tetracycline, doxorubicin, erythromycin, and rapamycin, etc.

Generation of cancer drug leads is usually accomplished via chemical synthetic methodologies using commercially available starting materials, or high-throughput natural product screening programs. Chemical synthetic methods are often laborious and inefficient, and achieving stereochemical and/or enantiomeric control can be difficult for target molecules with many stereocenters. On the other hand, specialized metabolic pathways feature enzyme catalysts that stringently steer stereochemically and enantiomerically controlled chemical reactions. Furthermore, specialized metabolic pathways include some "substrate flexibility" with respect to the range of chemical substrates that can be turned over by a given enzyme. This feature allows for combinatorial generation of several products. Biosynthesis of natural products affords an efficient, inexpensive means to generate important natural product drug leads. The development of new tools for genetic engineering in actinomycetes, e.g. strong promoters and multiplex integrating vectors, opens the door for robust biosynthetic production of novel drug molecules. Furthermore, biosynthesis is an efficient, inexpensive means to generate important chemical intermediates (e.g. anthracyclinones) that can be synthetically transformed into more useful cancer drug leads.

Anthracyclines are a structurally diverse class of polyketide molecules that exhibit important anticancer and antibacterial activities. Furthermore, anthracyclines in particular have been a mainstay of oncology drugs for several decades. Anthracyclines demonstrate multiple mechanisms of action, including intercalation into DNA, inhibition of topoisomerase II-dependent scission of supercoiled DNA, and the superoxide-mediated formation of free radicals and resultant macromolecule damage. Most of the biologically active anthracyclines feature an oxidatively modified four ring system and deoxysugar modifications that are important for intercalation into DNA. The natural product anthracyclines include daunorubicin, doxorubicin, nogalamycin, and aclacinomycin. Semi-synthetic anthracyclines in clinical use include idarubicin, epirubicin, and valrubicin.

SUMMARY OF THE INVENTION

The present invention provides a genetically modified host organism for expressing an anthracyclinone analogue. The genetically modified host organism comprises (i) synthetic nucleic acids. The genetically modified host organism further comprises (ii) a biosynthetic pathway encoded by the synthetic nucleic acids. The (ii) biosynthetic pathway comprises a ketosynthase alpha, a ketosynthase beta/chain-length factor, an acyl carrier protein, a 3-oxoacyl-ACP synthase, a propionyl-CoA acyltransferase, a 9-ketoreductase, an aromatase/cyclase, and a second/third-ring cyclase. The genetically modified host organism additionally comprises (iii) a promoter positioned upstream of and operatively associated with the (ii) biosynthetic pathway.

The present invention also provides a method for preparing an anthracyclinone analogue with the genetically modified host organism. The method comprises culturing the genetically modified host organism for a period of time sufficient to prepare the anthracyclinone analogue. Optionally, the method comprises isolating the anthracyclinone analogue from the genetically modified host organism.

The synthetic nucleic acids and expression vectors associated with the genetically modified host organism are also provided.

DETAILED DESCRIPTION OF THE INVENTION

The present invention provides a genetically modified host organism for expressing enzymes necessary for the production of an anthracyclinone analogue. The anthracyclinone analogue may be utilized for diverse end use applications, and may be further modified via various synthetic techniques. A method for preparing an anthracyclinone analogue with the genetically modified host organism is also disclosed, along with synthetic nucleic acids associated therewith.

As will be appreciated, the anthracyclinone analogue is a polyketide, and may be further described as an aromatic polyketide. As used herein, the term polyketide refers to specialized metabolites (e.g. secondary metabolites) produced by a polyketide synthase (PKS), a multi-domain enzyme or enzyme complex corresponding to polyketide biosynthetic genes, via decarboxylative condensation of malonyl-CoA extender units via a Claisen condensation. A PKS may be combined with other enzymes or domains to form a polyketide. Such a combination is typically referred to as a biosynthetic pathway. Such other enzymes or domains include, for example, monooxygenases, cyclases, ketoreductases, hydroxylases, cyclasedehydratases (DH), enoylreductases (ER), methyltransferases (MT), sulfhydrolases (SH), and thioesterases (TE). Each enzyme of a biosynthetic pathway is encoded by a biosynthetic gene. For example, aromatic polyketides are typically synthesized via a minimal polyketide synthase (minimal PKS) consisting of a beta-ketoacyl synthase (KSα) and chain length factor (KSβ) heterodimer and an acyl carrier protein (ACP) in combination with additional ketoreductase (KR), aromatase (ARO), and cyclase monofunctional enzymes or domains that dictate stereochemistry and cyclization of the aromatic polyketide.

The genetically modified host organism comprises (i) synthetic nucleic acids. The genetically modified host organism further comprises (ii) a biosynthetic pathway encoded by the (i) synthetic nucleic acids. It is to be appreciated that a particular enzyme of the (ii) biosynthetic pathway may be referred to in terms of the synthetic nucleic acids or gene that encodes the particular enzyme. Thus, while the term biosynthetic pathway is typically used to refer to the enzymes associated with production of the anthracyclinone analogue, the term also encompasses the synthetic nucleic acids or genes that encode such enzymes.

The (ii) biosynthetic pathway of the genetically modified host organism comprises a ketosynthase alpha, a ketosynthase beta/chain-length factor, an acyl carrier protein, a 3-oxoacyl-ACP synthase, a propionyl-CoA acyltransferase, a 9-ketoreductase, an aromatase/cyclase, and a second/third-ring cyclase.

The genetically modified host organism further comprises (iii) a promoter positioned upstream of and operatively associated with the (ii) biosynthetic pathway.

Typically, the genetically modified host organism includes a synthetic nucleic acid, or synthetic nucleic acid sequence, which corresponds to (i.e., encodes) one or each of the enzymes of the (ii) biosynthetic pathway, as described in greater detail below.

The genetically modified host organism is not limited and may be any suitable host organism which may be genetically engineered to express an anthracyclinone analogue as described herein. In specific embodiments, the genetically modified host organism comprises an actinomycete or derivative thereof. Actinomycetes and their derivatives are generally known in the art. Exemplary examples thereof include *Streptomyces lividans, Streptomyces coelicolor* A3(2), *Streptomyces griseus, Streptomyces albus, Streptomyces peucetius, Streptomyces galilaeus, Streptomyces cinnomonensis, Streptomyces nogalater, Streptomyces griseoflavus, Streptomyces albaduncus, Streptomyces venezuelae,* and *Streptomyces olivaceus*. In various embodiments, the genetically modified host organism comprises at least one of these exemplary actinomycetes. The genetically modified host organism may comprise a combination of different host organisms, e.g. different strains of an actinomycete in combination with one another, or a strain or strain(s) of actinomycete in combination with a different type of genetically modified host organism.

In these or other embodiments, the genetically modified host organism is genetically engineered to lack native polyketide biosynthetic genes.

In one specific embodiment, the genetically modified host organism comprises *Streptomyces coelicolor* CH999. In another specific embodiment, the genetically modified host organism comprises *Streptomyces coelicolor* CH999 (pFEN-1), which is obtainable by transforming construct pFEN-1 into the anthracycline non-producing host strain *Streptomyces coelicolor* CH999.

As introduced above, the genetically modified host organism typically includes a synthetic nucleic acid or synthetic nucleic acid sequence corresponding to each enzyme present within the (ii) biosynthetic pathway. Typically, the synthetic nucleic acid sequences corresponding to each enzyme are arranged to form a polygenic operon. The order and arrangement of genes within the polygenic operon is not limiting and the synthetic nucleic acid sequences optionally are configured such that when enzymes are produced (i.e. through translation) from an mRNA produced from the synthetic nucleic acid sequences into mRNA the enzymes are produced in a sequential order corresponding to the temporal arrangement of their respectively catalyzed chemical reactions within the (ii) biosynthetic pathway.

In certain embodiments, the ketosynthase alpha of the (ii) biosynthetic pathway is AknB, and thus the genetically modified host organism comprises a synthetic nucleic acid or synthetic nucleic acid sequence encoding AknB. In a specific embodiment, the synthetic nucleic acid or synthetic nucleic acid sequence encoding the AknB has SEQ ID NO: 1. This and other sequence listings described herein can be found in the SEQUENCE LISTING included herewith and incorporated herein by reference.

It is to be understood in the case of the enzyme (or, alternatively, "protein") name AknB and all enzyme names referenced herein that the enzyme name is intended to designate any protein sequence corresponding to any enzyme that may catalyze a similar chemical reaction, for example, as in the case of AknB, a ketosynthase alpha enzymatic reaction. That is to say, it is understood that mutant protein sequences corresponding to enzymes having altered properties beneficial to the functionality of the (ii) biosynthetic pathway are encompassed by the referenced enzyme families and sequences referenced herein insofar as the enzymes catalyze a common chemical reaction. As non-limiting examples, mutant variants of enzymes that demonstrate improved thermal stabilities or catalytic properties are encompassed by the referenced enzyme families (for example, ketoxynthase alpha enzymes) and sequences referenced herein. Moreover, as described further below, codon-optimized gene sequences or synthetic gene sequences corresponding to various desirable effects (for example, those influencing mRNA translation) that encode the referenced enzyme families and sequences referenced herein are encompassed by the enzyme names referenced herein.

In these or other embodiments, the ketosynthase beta/chain-length factor of the (ii) biosynthetic pathway is AknC, and thus the genetically modified host organism comprises a synthetic nucleic acid or synthetic nucleic acid sequence encoding AknC. In a specific embodiment, the synthetic nucleic acid or synthetic nucleic acid sequence encoding the AknC has SEQ ID NO: 2.

In these or other embodiments, the acyl carrier protein of the (ii) biosynthetic pathway is AknD, and thus the genetically modified host organism comprises a synthetic nucleic acid or synthetic nucleic acid sequence encoding AknD. In a specific embodiment, the synthetic nucleic acid or synthetic nucleic acid sequence encoding the AknD has SEQ ID NO: 3.

In these or other embodiments, the 3-oxoacyl-ACP synthase of the (ii) biosynthetic pathway is AknE2, and thus the genetically modified host organism comprises a synthetic nucleic acid or synthetic nucleic acid sequence encoding AknE2. In a specific embodiment, the synthetic nucleic acid or synthetic nucleic acid sequence encoding the AknE2 has SEQ ID NO: 4.

In these or other embodiments, the propionyl-CoA acyltransferase of the (ii) biosynthetic pathway is AknF, and thus the genetically modified host organism comprises a synthetic nucleic acid or synthetic nucleic acid sequence encoding AknF. In a specific embodiment, the synthetic nucleic acid or synthetic nucleic acid sequence encoding the AknF has SEQ ID NO: 5.

In certain embodiments, SEQ ID NO: 1 to SEQ ID NO: 5 are derived from the aclacinomycin pathway of *Streptomyces galilaeus* 31615.

In certain embodiments, the 9-ketoreductase of the (ii) biosynthetic pathway is DpsE, and thus the genetically modified host organism comprises a synthetic nucleic acid or synthetic nucleic acid sequence encoding DpsE. In a specific embodiment, the synthetic nucleic acid or synthetic nucleic acid sequence encoding the DpsE has SEQ ID NO: 6.

In these or other embodiments, the aromatase/cyclase of the (ii) biosynthetic pathway is DpsF, and thus the genetically modified host organism comprises a synthetic nucleic acid or synthetic nucleic acid sequence encoding DpsF. In a specific embodiment, the synthetic nucleic acid or synthetic nucleic acid sequence encoding the DpsF has SEQ ID NO: 7.

In these or other embodiments, the second/third-ring cyclase of the (ii) biosynthetic pathway is DpsY, and thus the genetically modified host organism comprises a synthetic nucleic acid or synthetic nucleic acid sequence encoding DpsY. In a specific embodiment, the synthetic nucleic acid or synthetic nucleic acid sequence encoding the DpsY has SEQ ID NO: 8.

In certain embodiments, SEQ ID NO: 6 to SEQ ID NO: 8 are derived from the daunorubicin pathway of *Streptomyces peucetius* ATCC 29050.

When the (ii) biosynthetic pathway of the genetically modified host organism has the attributes above, the (ii) biosynthetic pathway of the genetically modified host organism may be referred to as aknBCDE2FdpsEFY. In such embodiments, such enzymes are typically overexpressed by the genetically modified host organism, typically due to the influence of the (iii) promoter on the genes (i.e., the synthetic nucleic acid or synthetic nucleic acid sequence) encoding such enzymes.

In certain embodiments, the (ii) biosynthetic pathway of the genetically modified host organism further comprises at least one of: (i) a C-12 anthrone monooxygenase; (ii) an aklanonic acid methyltransferase; (iii) an aklanonic acid methyl ester cyclase; (iv) an aklaviketone ketoreductase; (v) a C-11 hydroxylase; and (vi) a nogalonic acid methyl ester cyclase. The (ii) biosynthetic pathway of the genetically modified host organism may comprise any one or combination of (i) to (vi) above. In certain embodiments, the (ii) biosynthetic pathway of the genetically modified host organism includes all of (i) to (vi). In other embodiments, the (ii) biosynthetic pathway of the genetically modified host organism includes the (i) C-12 anthrone monooxygenase; the (ii) aklanonic acid methyltransferase; the (iii) aklanonic acid methyl ester cyclase; the (iv) aklaviketone ketoreductase; and the (v) C-11 hydroxylase. In other embodiments, the (ii) biosynthetic pathway of the genetically modified host organism includes the (i) C-12 anthrone monooxygenase; the (ii) aklanonic acid methyltransferase; the (iv) aklaviketone ketoreductase; the (v) C-11 hydroxylase; and the (vi) nogalonic acid methyl ester cyclase.

As introduced above, the genetically modified host organism typically includes a synthetic nucleic acid or synthetic nucleic acid sequence corresponding to each enzyme present within the (ii) biosynthetic pathway.

In certain embodiments, the (ii) biosynthetic pathway includes the (i) C-12 anthrone monooxygenase. In particular embodiments, the (i) C-12 anthrone monooxygenase is DnrG, and thus the genetically modified host organism comprises a synthetic nucleic acid or synthetic nucleic acid sequence encoding the DnrG. In a specific embodiment, the synthetic nucleic acid or synthetic nucleic acid sequence encoding the DnrG has SEQ ID NO: 9.

In these or other embodiments, the (ii) biosynthetic pathway includes the (ii) aklanonic acid methyltransferase. In particular embodiments, the (ii) aklanonic acid methyltransferase is DnrC and thus the genetically modified host organism comprises a synthetic nucleic acid or synthetic nucleic acid sequence encoding the DnrC. In a specific embodiment, the synthetic nucleic acid or synthetic nucleic acid sequence encoding the DnrC has SEQ ID NO: 10.

In these or other embodiments, the (ii) biosynthetic pathway includes the (iii) aklanonic acid methyl ester cyclase. In particular embodiments, the (iii) aklanonic acid methyl ester cyclase is DnrD, and thus the genetically modified host organism comprises a synthetic nucleic acid or synthetic nucleic acid sequence encoding the DnrD. In a specific embodiment, the synthetic nucleic acid or synthetic nucleic acid sequence encoding the DnrD has SEQ ID NO: 11.

In these or other embodiments, the (ii) biosynthetic pathway includes the (iv) aklaviketone ketoreductase. In particular embodiments, the (iv) aklaviketone ketoreductase is DnrE, and thus the genetically modified host organism comprises a synthetic nucleic acid or synthetic nucleic acid sequence encoding the DnrE. In a specific embodiment, the synthetic nucleic acid or synthetic nucleic acid sequence encoding the DnrE has SEQ ID NO: 12.

In these or other embodiments, the (ii) biosynthetic pathway includes the (v) C-11 hydroxylase. In particular embodiments, the (v) C-11 hydroxylase is DnrF, and thus the genetically modified host organism comprises a synthetic nucleic acid or synthetic nucleic acid sequence encoding the DnrF. In a specific embodiment, the synthetic nucleic acid or synthetic nucleic acid sequence encoding the DnrF has SEQ ID NO: 13.

In these or other embodiments, the (ii) biosynthetic pathway includes the (vi) nogalonic acid methyl ester cyclase. In particular embodiments, the (vi) nogalonic acid methyl ester cyclase is SnoaL, and thus the genetically modified host organism comprises a synthetic nucleic acid or synthetic nucleic acid sequence encoding the SnoaL. In a specific embodiment, the synthetic nucleic acid or synthetic nucleic acid sequence encoding the SnoaL has SEQ ID NO: 14.

The synthetic nucleic acids or synthetic nucleic acid sequences corresponding to DnrG, DnrC, DnrD, DnrE, DnrF, and SnoaL may be referred to as post-PKS tailoring genes and, likewise, the enzymes encoded by the DnrG, DnrC, DnrD, DnrE, DnrF, and SnoaL genes may be referred to as post-PKS tailoring enzymes (or, more simply, as tailoring enzymes). In certain embodiments, the (ii) biosynthetic pathway of the genetically modified host organism comprises DnrGCDEF, DnrGCDEFSnoaL, or DnrGCEFSnoal.

Depending on a selection of these post-PKS tailoring genes, the encoded enzymes may be utilized (e.g. in the (ii) biosynthetic pathway) to chemically transform 12-deoxyaklanonic acid into a four-ringed anthracyclinone analogue in the genetically modified host organism. One example of such a four-ringed anthracyclinone analogue is epsilon-rhodomycinone.

In certain embodiments, SEQ ID NO: 9 to SEQ ID NO: 14 are derived from the doxorubicin biosynthetic pathway of *Streptomyces peucetius* ATCC 29050.

A genetically modified host organism comprising any one of SEQ ID NO: 1 to SEQ ID NO: 14 is also provided.

Typically, the genetically modified host organism comprises the synthetic nucleic acids corresponding to the (ii) biosynthetic pathway in a multi-gene operon. For example, in some embodiments the genetically modified host organism comprises a multi-gene operon comprising: (i) DnrGCDEF; (ii) DnrGCDEFSnoaL; (iii) DnrGCEFSnoal; or (iv) aknBCDE2FdpsEFY, each as described above; or (v) a combination of one of (i)-(iii) and (iv).

As introduced above, the genetically modified host organism further comprises (iii) the promoter positioned upstream of and operatively associated with the (ii) biosynthetic pathway. By "operatively associated with," it is meant that the (iii) promoter controls, influences, or increases expression of the relevant gene or enzyme. The (iii) promoter is not limited and may be any suitable promoter known in the art. In certain embodiments, the (iii) promoter comprises at least one of Pgap, Prps, Pxnr, PermE*, PactI-actII-ORF4, ermE*p, GAPDH, rpsLp, Pxnr, and kasOp*. In alternative embodiments, promoters having beneficial regulatory interactions with various proteins or promoters further associated with synthetic nucleic acid sequences having beneficial regulatory interactions with various proteins that function to influence the functioning of the promoter may be positioned upstream of and operatively associated with the (ii) biosynthetic pathway, for example, a lac promoter or a lux promoter region. Functional homologs of the above referenced promoters are encompassed within embodiments of the genetically modified host organism and synthetic nucleic acids.

In certain embodiments, the (iii) promoter comprises ermE*p. The synthetic nucleic acid corresponding to ermE*p has SEQ ID NO: 15.

In these or other embodiments, the (iii) promoter comprises GAPDH. The synthetic nucleic acid corresponding to GAPDH has SEQ ID NO: 16.

In these or other embodiments, the (iii) promoter comprises rpsLp. The synthetic nucleic acid corresponding to rpsLp has SEQ ID NO: 17.

In these or other embodiments, the (iii) promoter comprises Pxnr. The synthetic nucleic acid corresponding to Pxnr has SEQ ID NO: 18.

In these or other embodiments, the (iii) promoter comprises kasOp*. The synthetic nucleic acid corresponding to kasOp* has SEQ ID NO: 19.

In particular embodiments, the genetically modified host organism comprises one of the (iii) promotors listed above positioned upstream of and operatively associated with a multi-gene operon (i.e. a polygenic operon) comprising: (i) DnrGCDEF; (ii) DnrGCDEFSnoaL; (iii) DnrGCEFSnoal; or (iv) aknBCDE2FdpsEFY. In these or other embodiments, the genetically modified host organism comprises one of the (iii) promotors listed above positioned upstream of and operatively associated with a multi-gene operon comprising: (i) DnrGCDEF; (ii) DnrGCDEFSnoaL; or (iii) DnrGCEFSnoal, and another of the (iii) promoters listed above positioned upstream of and operatively associated with a multi-gene operon comprising (iv) aknBCDE2FdpsEFY.

A genetically modified host organism comprising any one of SEQ ID NO: 15 to SEQ ID NO: 19 is also provided.

As introduced above, the genetically modified host organism typically includes a synthetic nucleic acid corresponding to each enzyme present in the (ii) biosynthetic pathway. Each synthetic nucleic acid is also provided independent of inclusion in the genetically modified host organism. The synthetic nucleic acids generally include a sequence of base pairs corresponding to restriction endonuclease sites, and differ from the synthetic nucleic acids upon inclusion in the genetically modified host organism (through loss of the restriction endonuclease sites). These restriction endonuclease sites 5' to each synthetic nucleic acid include EcoRI (GAATTC) and XbaI sites (TCTAGA), and the restriction endonuclease sites sites 3' to each synthetic nucleic acid include SpeI (ACTAGT) and PstI sites (CTGCAG).

The synthetic nucleic acid corresponding to AknB prior to incorporation into the genetically modified host organism has SEQ ID NO: 20.

The synthetic nucleic acid corresponding to AknC prior to incorporation into the genetically modified host organism has SEQ ID NO: 21.

The synthetic nucleic acid corresponding to AknD prior to incorporation into the genetically modified host organism has SEQ ID NO: 22.

The synthetic nucleic acid corresponding to AknE2 prior to incorporation into the genetically modified host organism has SEQ ID NO: 23.

The synthetic nucleic acid corresponding to AknF prior to incorporation into the genetically modified host organism has SEQ ID NO: 24.

The synthetic nucleic acid corresponding to DpsE prior to incorporation into the genetically modified host organism has SEQ ID NO: 25.

The synthetic nucleic acid corresponding to DpsF prior to incorporation into the genetically modified host organism has SEQ ID NO: 26.

The synthetic nucleic acid corresponding to DpsY prior to incorporation into the genetically modified host organism has SEQ ID NO: 27.

The synthetic nucleic acid corresponding to DnrG prior to incorporation into the genetically modified host organism has SEQ ID NO: 28.

The synthetic nucleic acid corresponding to DnrC prior to incorporation into the genetically modified host organism has SEQ ID NO: 29.

The synthetic nucleic acid corresponding to DnrE prior to incorporation into the genetically modified host organism has SEQ ID NO: 30.

The synthetic nucleic acid corresponding to DnrF prior to incorporation into the genetically modified host organism has SEQ ID NO: 31.

The synthetic nucleic acid corresponding to SnoaL prior to incorporation into the genetically modified host organism has SEQ ID NO: 32.

The synthetic nucleic acid corresponding to ermE*p prior to incorporation into the genetically modified host organism has SEQ ID NO: 33.

The synthetic nucleic acid corresponding to GAPDH prior to incorporation into the genetically modified host organism has SEQ ID NO: 34.

The synthetic nucleic acid corresponding to rpsLp prior to incorporation into the genetically modified host organism has SEQ ID NO: 35.

The synthetic nucleic acid corresponding to Pxnr prior to incorporation into the genetically modified host organism has SEQ ID NO: 36.

The synthetic nucleic acid corresponding to kasOp* prior to incorporation into the genetically modified host organism has SEQ ID NO: 37.

In certain embodiments, the genetically modified host organism further comprises a transcription terminator operatively associated with the (ii) biosynthetic pathway. The transcription terminator is not limited and may be any transcription terminator known in the art. In particular embodiments, the transcription terminator is present within one or more of the multi-gene operons described above.

Each of the synthetic nucleic acids above can be introduced into a host organism to prepare the genetically modified host organism by any suitable technique, as understood in the art. In certain embodiments, the introduction of the synthetic nucleic acids into the host organism to prepare the genetically modified host organism is such that the nucleic acids are replicable in the genetically modified host organism in an extrachromosomal plasmid. In other embodiments, the introduction of the synthetic nucleic acids in the host organism to prepare the genetically modified host organism integrates at least one, alternatively all, of the synthetic nucleic acids into chromosome(s) of the genetically modified host organism, e.g. via an integrase or an actinophage integrase. In certain embodiments, the synthetic nucleic acids are introduced into the host organism via protoplast transformation, intergeneric conjugation, heat shock transformation, and/or electroporation to prepare the genetically modified host organism.

In certain embodiments, the synthetic nucleic acids of the (ii) biosynthetic pathway and (iii) promotor, and optionally nucleic acid(s) corresponding to the transcription terminator are integrated into a plasmid or expression vector that is subsequently introduced into the host organism to prepare the genetically modified host organism. The integration of the synthetic nucleic acids of the (ii) biosynthetic pathway and (iii) promotor, and optionally the nucleic acid(s) corresponding to the transcription terminator into the plasmid or expression vector can be carried out by any technique known in the art, for example, various DNA ligation techniques or through custom DNA/gene synthesis. Typically, the synthetic nucleic acids of the (ii) biosynthetic pathway and (iii) promotor, and optionally the nucleic acid(s) corresponding to the transcription terminator are combined with specific nucleic acids composing a plasmid or expression vector to form an integrating plasmid vector, such as a multiplex integrating plasmid vector (e.g. pENBT1, pENSV1, and/or pENTG1). It is to be understood that integrating plasmid vectors, as understood herein, encode an integrase.

Examples of nucleic acids composing a plasmid suitable for such purposes include plasmid pSET152 encoding the phiC31 integrase.

In certain embodiments, an integrating plasmid vector for preparing the genetically engineered host organism comprises a synthetic nucleic acid sequence corresponding to at least a region of pENBT1, pENSV1, and/or pENTG1.

A synthetic nucleic acid corresponding to φBT1 int-attP region-neoR-oriT region of pENBT1 vector is also provided, which has SEQ ID NO: 38.

A synthetic nucleic acid corresponding to SV1-int-attP region-aadR-oriT region of pENSV1 vector is additionally provided, which has SEQ ID NO: 39.

A synthetic nucleic acid corresponding to TG1-int-attP region-aadR-oriT region of pENTG1 vector is further provided, which has SEQ ID NO: 40.

In some embodiments, the synthetic nucleic acids of the (ii) biosynthetic pathway and the (iii) promotor, and optionally the nucleic acid(s) corresponding to the transcription terminator, are assembled into an expression vector. In some such embodiments, the synthetic nucleic acids of the (ii) biosynthetic pathway and the (iii) promotor, and optionally the nucleic acid(s) corresponding to the transcription terminator are assembled via restriction endonuclease digestion and ligation of overlapping SpeI and XbaI digested DNA fragments, which are regenerated after each ligation event, to form (i.e., assemble) an expression construct. Such digestion and ligation is not limited, and may be performed via any techniques and/or procedures known in the art. The expression construct is then digested into an EcoRI and/or PstI site within one of the plasmids or vectors described above, or a synthetic nucleic acid corresponding to one of the plasmids or vectors as described above, to form the integrating plasmid vector. In some embodiments, the synthetic nucleic acids of the (ii) biosynthetic pathway and the (iii) promotor(s), and optionally the nucleic acid(s) corresponding to the transcription terminator as well as one of the plasmids or vectors described above or a synthetic nucleic acid corresponding to one of the plasmids or vectors as described above are assembled together via custom DNA/gene synthesis. As introduced above, the integrating plasmid may then be introduced into the host organism to prepare the genetically modified host organism.

In specific embodiments, depending on a selection of the host organism and other factors, host organisms transformed with the above integrating plasmid vectors undergo site specific recombination in the *Streptomyces* genome, and the resulting genetically modified host organism may stably maintain the inserted synthetic nucleic acid material without antibiotic selection pressure.

The synthetic nucleic acids of this invention are synthetic sequence variants of naturally occurring, wildtype nucleic acids and are generated via gene synthesis. The synthetic nucleic acids are codon-optimized for expression. In certain embodiments, one or more of the synthetic nucleic acids described above is engineered to lack EcoRI, SpeI, XbaI, and/or PstI internal restriction endonuclease sites, such that construction of such restriction endonuclease sites into the multigene operon is greatly facilitated. The synthetic nucleic acids described above can be recombined into multigene operons via restriction endonuclease digestion, ligation, and other techniques understood by one of skill in the art.

A method of preparing the anthracyclinone analogue with the genetically modified host organism is also provided. The method comprises culturing the genetically modified host organism for a period of time sufficient to prepare the anthracyclinone analogue. The method optionally comprises isolating the anthracyclinone analogue from the genetically modified host organism.

In certain embodiments, the term "anthracyclinone analogue" means an aromatic polyketide including three rings or four rings as defined by structural formulae (i) and/or (ii) below:

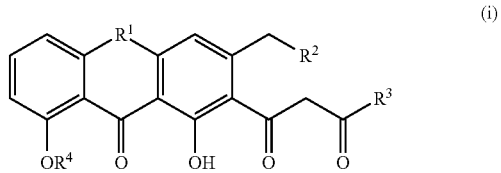

(i)

wherein $R^1$ is $CH_2$, CHOH, or C(O); $R^2$ is hydrogen, methyl, carboxyl (C(O)OH), carboxymethyl (C(O)OCH$_3$), CH$_2$OH, or a protecting group; $R_3$ is hydroxyl, methyl, ethyl, propionyl, butyl, NH$_2$, CH$_2$OH, or a protecting group; and $R^4$ is hydrogen or methyl; or

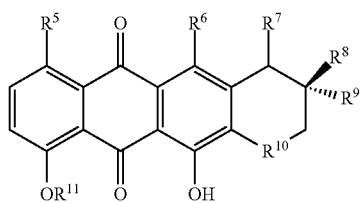

(ii)

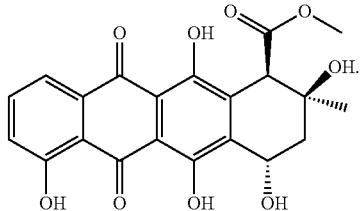

(vii)

wherein $R^5$ is hydrogen, hydroxyl, or a halogen; $R^6$ is hydrogen or hydroxyl; $R^7$ is hydrogen, carboxyl (C(O)OH), carboxymethyl (C(O)OCH$_3$), or hydroxyl; $R^8$ is methyl, ethyl, propionyl, butyl, vinyl, hydroxyl, carboxyl (C(O)OH), or a protecting group; $R^9$ is methyl, ethyl, propionyl, butyl, vinyl, hydroxyl, carboxyl (C(O)OH), or a protecting group; $R^{10}$ is CHOH, or C(O), and $R^{11}$ is H or CH$_3$; wherein the protecting group of $R^2$, $R^3$, $R^8$, and/or $R^9$ independently comprises a substituted or unsubstituted hydrocarbyl group, an ester group, a carbonate group, a carboxy group, an aldehyde group, a ketone group, a urethane group, a silyl group, a sulfoxo group, or a phosphonic acid group.

In specific embodiments, the anthracyclinone analogue has at least one of the following formulas (iii) to (vii):

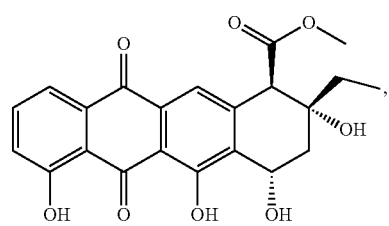

(iii)

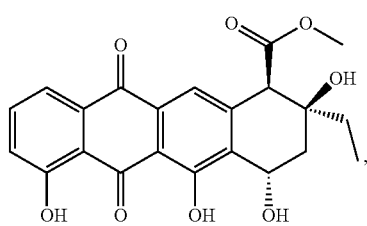

(iv)

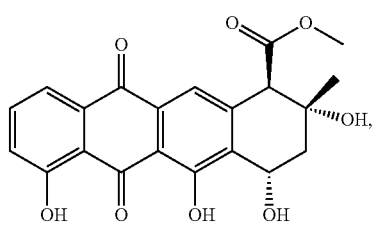

(v)

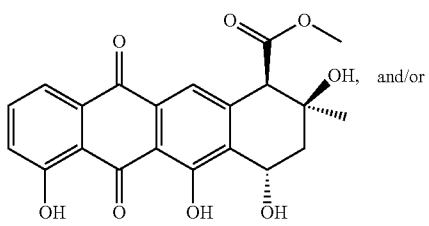

(vi) and/or

The genetically modified host organism can be cultured in any suitable growth medium. In certain embodiments, the genetically modified host organism is cultured in a shake flask or a bioreactor. Typically, after several days of growth, a culture of the genetically modified host organism contains a high amount of cells (mycelium) with a liquid layer (supernatant), which each contain an amount of the anthracyclinone analogue. The culture may be separated into a liquid phase (supernatant) and a solid phase (mycelium) via filtration or related methodologies, and the two phases may be subjected to several processes to extract or otherwise isolate the anthracyclinone analogue, such as with solvent (e.g. aqueous and/or organic solvents), and/or chromatographic separation techniques (e.g. solid phase extraction, high performance liquid chromatography (HPLC) for the purpose of obtaining the anthracyclinone analogue as a purified compound.

The anthracyclinone analogue may be further processed (e.g. chemically transformed via chemical and/or biochemical techniques) to form a derivative of the anthracyclinone analogue. For example, the anthracyclinone analogue is useful for derivatization to form a glycosylated anthracycline molecule. Typically, the anthracyclinone analogue and/or the glycosylated anthracycline molecule exhibits an antibacterial and/or anticancer property. Accordingly, the present invention also provides a pharmaceutical comprising the anthracyclinone analogue or a derivative, salt, or solvate thereof.

It is to be understood that the appended claims are not limited to express any particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

The words "homologous" or "homolog" as employed herein are used according to their commonly understood meanings in the art. Optionally "homologous" sequences share at least 70% sequence identity, optionally at least 80% sequence identity, optionally at least 90% sequence identity, optionally 95% sequence identity, further optionally 99% sequence identity. The phrase "functional homolog" is encompassed by the word "homologous" and includes each member of that subgroup of homologs or homologous sequences that share a common functionality. "Functionality" as used herein refers only to the primary function for which a protein, gene, sequence, and the like is named. For example, the function of a promoter is to facilitate transcription of a gene or nucleotide sequence and the function of an enzyme is to catalyze a particular chemical reaction or family of chemical reactions. As a non-limiting example, the term "functionality" encompasses all reaction rates and all enzymatic efficiencies corresponding to a particular primary function of a protein insofar as the protein can carry out that primary function for which the protein has been named.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The following examples, illustrating the composition and method, are intended to illustrate and not to limit the invention.

EXAMPLES

Example 1: Transformation of *Streptomyces coelicolor* Strains with Module 1 Constructs Strains *Streptomyces coelicolor* M145, *Streptomyces coelicolor* CH999, and *Streptomyces coelicolor* M1146 were independently transformed with constructs expressing Module 1 to prepare genetically modified hosts. Module 1 includes eight synthetic genes aknB, aknC, aknD, aknE2, aknF, dpsE, dpsF, and dpsY spliced into an operon. The biosynthetic enzymes encoded by each of the eight synthetic genes (namely, AknB, AknC, AknD, AknE2, AknF, DpsE, DpsF, and DpsY) together constitute the minimal polyketide synthase of the doxorubicin pathway, which function collectively to produce aklanonic acid. This operon was fused to several different actinomycete promoters to determine the effect of promoter strength on production of aklanonic acid.

The different actinomycete promoters included erythromycin resistance up promoter (ermE*p), the strong glyceraldehyde-3-phosphate dehydrogenase promoter (gapdhp) from *Eggerthella lenta*, the 30S ribosomal protein S12 promoter from *Cellulomonas flavigena* (rpsLp), the XNR_1700 peptide transport system secreted peptide-binding protein promoter (p15) from *Streptomyces albus*, and the strong engineered kasOp* promoter from *S. coelicolor*.

The promoter-aknBCDE2FdpsEFY fusion constructs were spliced into integrative plasmid pSET152, which harbors the φC31 phage integrase for recombination into the φC31 attB site on the *Streptomyces* chromosome.

The prepared Module 1 constructs are described in Table 1.

TABLE 1

Integrative constructs for expressing aknBCDE2FdpsEFY under the control of different promoters.

| Plasmid name | Promoter | Gene cassette | Resistance Marker |
|---|---|---|---|
| pSET152 | — | — | aac(3)IV |
| pSET-EN61 | ermE*p | aknBCDE2FdpsEFY | aac(3)IV |
| pSET-EN62 | gaphdhp | aknBCDE2FdpsEFY | aac(3)IV |
| pSET-EN63 | rpsLp | aknBCDE2FdpsEFY | aac(3)IV |
| pSET-EN64 | p15 | aknBCDE2FdpsEFY | aac(3)IV |
| pSET-EN65 | kasOp* | aknBCDE2FdpsEFY | aac(3)IV |

The constructs were transformed into chemically competent *E. coli* ET12567/(pUZ8002) cells and selected on LB agar supplemented with chloramphenicol/kanamycin/apramycin. The *E. coli* ET12567/(pUZ8002) cells transformed with the above constructs were used to transform *S. coelicolor* spores by intergeneric conjugation.

*Streptomyces coelicolor* conjugation plates were overlaid with apramycin (50 μg/mL) and grown at 30 degrees Celsius for 3-4 days. After the appearance of exconjugants, twelve individual colonies per transformation were plated to DIFCO Nutrient Agar media (DNA agar) supplemented with nalidixic acid (33 μg/mL) and apramycin (50 μg/mL) and were grown for another 3 days at 30 degrees Celsius.

Example 2: Transformation of Module 2 Genetic Constructs into *Streptomyces Coelicolor*

Strain *Streptomyces coelicolor* M1146/(pSET-EN65) was transformed with constructs expressing Module 2 to prepare genetically modified hosts. Module 2 includes a subset of eight synthetic genes dnrG, dnrC, dnrD, dnrE, dnrF, and snoaL spliced into an operon. The encoded biosynthetic enzymes (namely, DnrG, DnrC, DnrD, DnrE, DnrF, and SnoaL) are tailoring enzymes that may catalyze chemical modifications to either aklanonic acid or derivatives thereof. The prepared Module 2 constructs are described in Table 2.

The Module 2 genetic constructs were cloned into a pENSV1 genetic backbone. pENSV1 encodes the SV1 actinophage integrase that allows for recombination of DNA into the SV1 attB site in the *Streptomyces* chromosome.

*E. coli* ET12567/(pUZ8002) was transformed with the Module 2 genetic constructs described in Table 2. *E. coli* ET12567/(pUZ8002) strains individually harboring a single Module 2 genetic construct were used as a conjugation donor for matings with strain *Streptomyces coelicolor* M1146/(pSET-EN65) in intergeneric conjugation.

TABLE 2

Constructs expressing combinations of genetic module 2 (dnrGCDE cistron).

| Plasmid name | Promoter | Gene cassette | Resistance Marker | Integration locus |
|---|---|---|---|---|
| pENSV1 | — | — | vph | φSV1 attB site |
| pSV1-dnrG | gaphdhp | dnrG | vph | φSV1 attB site |
| pSV1-dnrGC | gaphdhp | dnrGC | vph | φSV1 attB site |
| pSV1-dnrGCD | gaphdhp | dnrGCD | vph | φSV1 attB site |
| pSV1-dnrGCDE | gaphdhp | dnrGCDE | vph | φSV1 attB site |

Conjugation plates were overlaid with nalidixic acid (33 μg/mL), apramycin (50 μg/mL), and viomycin (30 μg/mL) and were grown at 30 degrees Celsius for 3 days. Exconjugants were plated to DIFCO nutrient agar (DNA) plates supplemented with nalidixic acid (33 μg/mL), apramycin (50 μg/mL), and viomycin (30 μg/mL). Six exconjugants were picked and grown in 25 mL SG media in 250 mL shake flasks for 5 days. The resulting cultures were extracted via solid phase extraction and filtered for HRMS-QTOF analysis.

Example 3: HRMS-QTOF Analysis and Identification of Anthracyclinones

Samples were analyzed using HRMS-QTOF instrumentation. The samples were analyzed on a WATERS XEVO G2-XS QToF mass spectrometer for untargeted metabolomics analysis. In brief, the samples were diluted 100-fold in 20% methanol, and 5 microliters of the diluted samples was run on a gradient using 10 mM ammonium formate (mobile phase A) and acetonitrile (mobile phase B). The samples were analyzed on a Waters Acquity BEH C18 UPLC column, 2.1×100 mm, 1.7 μm particle size (temperature set to 40 C). The gradient used is provided as Table 3.

TABLE 3

Gradient used in gathering mass spectroscopy measurements

| Time (min) | Flow Rate | % A | % B | Curve |
|---|---|---|---|---|
| 1. Initial | 0.300 | 99.0 | 1.0 | initial |
| 2. 0.50 | 0.300 | 99.0 | 1.0 | 6 |

TABLE 3-continued

Gradient used in gathering mass spectroscopy measurements

| Time (min) | Flow Rate | % A | % B | Curve |
|---|---|---|---|---|
| 3. 7.00 | 0.300 | 1.0 | 99.0 | 6 |
| 4. 8.00 | 0.300 | 1.0 | 99.0 | 6 |
| 5. 8.01 | 0.300 | 99.0 | 1.0 | 6 |
| 6. 10.00 | 0.300 | 99.0 | 1.0 | 6 |

Samples were analyzed in both negative and positive ion mode and data were acquired using a data-independent analysis method method (MSe) with fast switching between a no collision energy function and a function with a collision energy ramp. The raw data was imported into PROGENESIS software for peak alignment and peak picking. Next, elemental composition analysis was performed on the picked ions using the following parameters: C (100), H (150), N (10), O (30), mass error 5 ppm, 95% isotope similarity.

Relative mass defect (RMD) was calculated. Based on this information, the accurate mass for expected metabolites was calculated and compared to the found accurate mass values detected in the samples. This lead to the positive identification of several anthracyclinone metabolites synthesized in the various genetically modified hosts (Table 4 and 5).

TABLE 4

Identification of aklanonic acid from *Streptomyces coelicolor* M1146/(pSET-kasOp*-aknBCDE2F+dpsEFY).

| Chemical Name | Chemical Structure | Structural Formula | Retention Time |
|---|---|---|---|
| aklanonic acid | (structure) | $C_{21}H_{16}O_8$ | 3.21 min. |

| Chemical Name | Calculated Mass | Found Mass | Relative Mass Defect |
|---|---|---|---|
| aklanonic acid | 395.0766 (M − H); 333.0763 (M − COOH) | 395.0757 (M − H); 333.0748 (M − COOH) | 232.12 |

TABLE 5

Identification of anthracyclinones from *Streptomyces coelicolor* M1146/(pSET-kasOp*-aknBCDE2F+dpsEFY) co-expressing a Module 2 construct.

| Module 2 Construct | Chemical Name | Chemical Structure | Structural Formula |
|---|---|---|---|
| pENSV1-gapdhp-dnrGC | aklanonic acid methyl ester (AAME) | (structure) | $C_{22}H_{18}O_8$ |

TABLE 5-continued

Identification of anthracyclinones from *Streptomyces coelicolor* M1146/(pSET-kasOp*-aknBCDE2F+dpsEFY) co-expressing a Module 2 construct.

| | | | |
|---|---|---|---|
| pENSV1-gaphpdp-dnrGCD | aklaviketone | 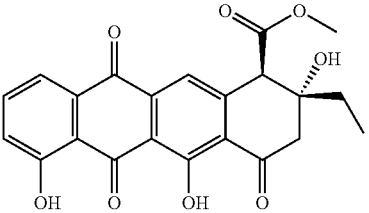 [SMILES: CC[C@@]1(O)CC(=O)c2c(cc3c(c2O)C(=O)c2c(O)cccc2C3=O)[C@H]1C(=O)OC] | $C_{22}H_{18}O_8$ |
| pENSV1-gaphpdp-dnrGCDE | aklavinone | 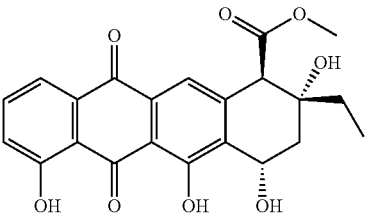 [SMILES: CC[C@@]1(O)C[C@H](O)c2c(cc3c(c2O)C(=O)c2c(O)cccc2C3=O)[C@H]1C(=O)OC] | $C_{22}H_{20}O_8$ |

| Module 2 Construct | Calc. Mass | Found Mass | Relative Mass Defect |
|---|---|---|---|
| pENSV1-gapdhp-dnrGC | 410.1001 (M+); 409.0923 (M − H) | 410.0990 (M+); 409.0922 (M − H) | 225.42 |
| pENSV1-gaphpdp-dnrGCD | 410.1001 (M+); 409.0923 (M − H) | 409.0925 (M − H) | 226.18 |
| pENSV1-gaphpdp-dnrGCDE | 412.1158 (M+); 411.1079 (M − H) | 411.1080 (M − H) | 262.65 |

SEQUENCE LISTING

SEQ ID NO: 1-AknB
GAAAGAGGAGAAATACTAGATGACCGCCCGTCGCGTGGTCATCACCGGCCTGGGCGTC
ATCGCCCCGGGTGGCATCGGCACCAAGGCCTTCTGGGAGCGGATCGTCTCCGGCGTCT
CCGCCACCCGCACCATCACCGCCTTCGACGCCTCCGAGTTCCGCTCCCGGATGGCCGC
CGAGTGCGACTTCGACGGCGTCCGCTCCGGCCTGACCGTCCGGGACACCGCCCGCCT
GGACCGGGCCACCCAGTTCGCCGTGGTGGCCGCCCGCGAGGCCCTGGCCGACTCCGG
CATCGAGATCGACGAGCGCAACGCCCACCGGACCGGCGTCTCCCTGGGCTCCGCCGT
CGGCTGCACCCAGAAGCTGGAGGAAGAGTACGTGGCCCGCTCCGACGGTGGCCAGCG
GTGGCTCGTGGACCACGCCGCCGGCACCCCGTACCTGTACGACTACTTCGTCCCGTCC
TCGATGGCCGCCGAGGTCGCCTGGGAGGCCGGCGCCGAGGGCCCGGCCGCCCTGGT
CTCCGCCGGCTGCACCTCGGGCCTGGACTCCCTGGGCCACGCCCTGGACCTGATCCG
CGAGGGCGCCGTGGACATCATGATCGCCGGCGGCTCCGACGCCCCATCGCCCCCAT
CACCGTGGCCTGCTTCGACGCCATCAAGGCCACCTCGCCGCGCAACGACACCCCGGAG
CACGCCTCCCGGCCGTTCGACCGCACCCGGTCCGGCTTCGTCCTGGGCGAGGGCGCC
GCCGTCCTGGTCCTGGAGGAGCGGGAGTCCGCCCTGCGCCGCGGTGCCCAAATCTAC
GCCGAGATCGCCGGCTACGCCGGCCGCGCCAACGCCCACCACATGACCGGCCTGCGG
CCCGACGGCCTGGAGATGTCCGCCGCCATCACCGGCGCCCTGGACGACGCCCGCATC
GACCGGGAGGCCGTGGGCTACGTCAACGCCCACGGCACCGCGACCCGCCAGAACGAC
ATCCACGAGACCGCCGCCATCAAGCACTCCCTGGGCGAGCACGCCCGCCGGGTCCCG
GTCTCCTCCATCAAGGCCGTCATCGGCCACTCCCTGGGCGCCGTGGGCTCCATCGAGG
CCGTCGCCTCCGCCCTGGTCATCCGCCACGGCGTCGTCCCGCCCACCGCCGGCCTGC
ACGAGCCGGACCCGCAGCTGGACCTGGACTACGTCCCCCTGATCGCCCGGGACCAGG
CCACCGACACCGTCCTGACCGTGGGCTCCGGCTTCGGCGGCTTCCAGTCCGGCGATGGT
CCTGACCTCGGCCGAGGGCGGCCGGTCCTGA

SEQ ID NO: 2-AknC
GAAAGAGGAGAAATACTAGATGTCCGCCGCCACCGTGGTCACCGGCATCGGCGTCCTG
GCCCCGAACGGCATCGGCGCCGAGGAGTTCTGGGCCGCCACCCTGCGGGCCGAGTCC
GGCATCGGCCGGATCACCCACTTCGAGCCCGCCTCCTACCCCTCCCGGCTGGCCGGC
GAGGTCACCGGCTTCTCCGCCCGCGAGCACCTGCCCTCCCGGCTGGTCCCGCAGACC
GACCGGACCACCCAGTTCGCCCTGACCGGCTCCGAGTGGGCCCTGCGGGACTCCGGC
CTGTCCGCCGACACCCTGCCGGCCGGTGAGCGCGGCGTCGTCACCGCCTCCGCCTCC
GGCGGCTTCGAGTTCGGCCAGCGGGAGCTGGGCCACCTGTGGGCAAGGACCCGCGC
CACGTCTCCGCCTACATGTCCTTCGCCTGGTTCTACGCCGTCAACTCCGGCCAGATCAG
CATCCGCCACGACCTGCGGGGCCCGACCGGCGTCCTGGTCACCGACCAGGCCGGCGG
CCTGGACGCCGTGGCCCAGGCCCGCCGGCGCATCCGCAAGGGCACCCCGGTCATGCT
GTCCGGCGGCATGGACGCCTCCCTGTGCCCGTACGGCCTGGTCGCCCAGATCAGCGC
CGGCATGCTGTCCGAGTCCGACGACCCCACCCGCGCCTACCGGCCGTTCGACCCCGC
CGCCGACGGCCACGTCCCGGGCGAGGGCGGCGCCATCCTGACCCTGGAGGACGGCG
ACCGCGCCCGCGCCCGCGGTGCCCGGTCCCACGGCGAGATCAGCGGCTACGCCGCCA

CCTTCGACCCGCGCCCGGGCTCCGGCCGGCCCGCCAACCTGGACCGCGCCATCCGCG
GTGCCCTGGCCGACGCCGGCCTGTCCCCGCGCGACATCGCCTTCGTCCTGGCCGACG
GCGCCGGCGAGCCCGAGCCGGACCGCGCCGAGGCCCGTGCCCTGACCGACGTCTTCG
GCCCGCGCGGCGTCCCCGTCACCGTCCCGAAGTCCATGACCGGCCGGCTGTACGCCG
GCGCCGCCCCGCTGGACCTGGTCACCGCCCTGTTCGCCCTGCGGGACGGCGTCGTCC
CGCCCACCGTCCACGTGGACGAGCCGGACCCCGCCTACGACATCGACCTGGTCACCG
GCTCCGCCCGCCCCGTCCGGGGCGACGCCGCCCTGGTCCTGGCCCGCGGCCGGGGC
GGCTTCAACTCCGCGATGGTCGTCCGTCGCCCGCCGGCCGCCTGA

SEQ ID NO: 3-AknD
GAAAGAGGAGAAATACTAGATGTCCGCCTTCACCGTCGAGGAGCTGTTCCAGATCATGC
GCGAGTGCGCCGGCGAGGAAGAGGCCGTGGACCTGGCCGACGCCGCCGAGCAGGAG
TTCGCCCTGCTGGGCTACGACTCCCTGGCCCTGATGGAGGCCATCTCCCGCGTCGAGC
GGGGCCTGGGCATCGCCCTGCCGGAGGAGACCGTGGGCGAGGTCCTGACCCCGGCC
GCCTTCGTGGACGTGGTCAACGCCGAGCTGGCCCGGTCCGCCCCGGTCGTCGAGGCC
GCCGGTTGA

SEQ ID NO: 4-AknE2
GAAAGAGGAGAAATACTAGATGACCGAGGAGCACCTGGACCCGGCCGGCGGCGCCCC
GCTGGCCCAGGCCCCGGCCCAGGACATCCGCATCGCCGGCTGCGCCGTCTGGCTGCC
GCCCCGGGCCCCCGTCGCCCAGGCCGTCGCCGCCGGTCTGTGCGACGAGGCCCTGGC
CACCGCCACCGCGATGGTCTCCGTCGCCGTCGCCCAGGACGAGCCGGCCCCCGAGAT
GGCCGCCCGTGCCGCCCGCACCGCCCTGGCCCGCGGCGGCTCCGACGACGTCTCCCT
GATCCTGCACGCCTCCTTCTTCTACCAGGGCCACGACCTGTGGGCCCCCGCCTCCTAC
GTCCAGCGCGTGGCCGTGGGCAACCACTGCCCGGCCATCGAGGTGGGCCAGGTCTCC
AACGGTGGCATGGCCGCCCTGGGCCTGGCCGTGGACCACCTGTCCGCCGGCCGCCCG
GCCGGCGCCGCCGGTCGCCGCGTCCTGGTCACCACCGGCGACGCCTTCCGTCCGCCG
GGCTTCGACCGCTGGCGGTCCGACCCCGGCCACCTTCTACGGCGACGGCGGCACCGCC
CTGGTCCTGTCCTCCCAGGAAGGCTTCGCCCGCATCCGGGGCCTGGCCACCGTCTCCG
CCCCCGAGCTGGAGGGCATGCACCGCGGCGACGACCCCTTCGGCTCCGCCCCGTTCT
CCCACCGGCCGGTGGTGGACCTGGAGGCCTGCAAGAAGGACTTCCTGGCCTCCCGCC
GGGTCACCCAGGTCATCGCCGCCTCCGCCGCCGCCCAGGACGCCGCCCTGGGCCAGG
CCCTGGCCGCCGCCGGTGCCGAGCTGGCCGACATCGACCGCTTCGTCCTGCCGCACAT
GGGCCGCAAGCGGCTGCGCGCCGGCTTCCTGAACCGCCTGGGCATCGGCGAGGACCG
CACCACCTGGGAGTGGTCCCGGGGCGTCGGCCACCTGGGCGCCGGCGACCAGATCGC
CGGCTTCGACCACCTGGTGGGCTCCGGCTCCCTGGGCCCCGGCGACCTGGTCCTGTG
GATGTCCGTGGGCGCCGGCTTCACCTACTCCTGCGCCGTCGTCGAGATGCTGGAGCGC
CCCGGCTGGGCCGCCACCGCCGGCACCGCCGGCGCCGCCTGA

SEQ ID NO: 5-AknF
GAAAGAGGAGAAATACTAGATGACCGGCACCGCCGGCGCCCTGCCCGTGGCCCTGCTG
CTGCCCGGCCAGGGCTCCCAGCACCGTCGCATGGCCGCCGGTCTGTACGGCCACGAG
CCCGTCTTCACCGAGGCGATGGACGAGTTCTTCGACGCCGCCGGTCCCGAGGGCGACC
CGCTGCGCGACGACTGGCTGGCCGAGCGGCCCGTCACCGACATCGACCACGTCACCC
GCTCCCAGCCCCTGCTGTTCGCCGTGGACCACGCCCTGGGCCGGCTGGTCCTGGGCC
GCGGCGTCCGGCCGGCCGCACTGCTGGGCCACTCCATCGGCGAGCTGGCCGCCGCAA
CCCTGGCCGGCGTCTTCGCCCCGCGCGACGCCGCCGGCCTGGTCCTGGACCGGATCC
GCCGGCTGTCCGCCGCCCCGCCCGGCGGCATGCTGGCCGTCGCCGCCTCCACCGCCG
AGGTCGCCCCCTACCTGCGCGGCGACGTCGTCGGCGCCGTCAACGCCCCGCGTC
AGACCGTCCTGGCCGGCCCGGACGGCCCCCTGGACGAGGTGGACCGCGCCCTGCGG
GAGGCCGGCTTCGTCTGCCGCCGGGTCCCCTCCCTGTCCGCCTTCCACTCCCCCGTCC
TGGAGCCGGCCTGCCGCGGCGCCGCCCCGCTGTTCGCCGCCGCATGCAAGCACCCGC
CCGCCGTCCCGGTCCACTCCGCCTACACCGCCGCCCCGCTGACCGAGTCCGACATCGA
CGACCCCGGCCTTCTGGGCCCGCCAGCCGGTCGCCCCCGTCCTGTTCTGGCCGGCCCT
GGAGGGCCTGCTGGCCACCGGCGACCACCTGCTGGTCGAGGTCGGCCCCGGCCAGGG
CCTGTCCCAGCTGGTCCGCCGGCACCCGGCCGTCCGCCGGGGCGGCTCCGCCGTCGT
CTCCCTGCTGCCCGCCCGCCCCGGTCCGCCGGAGGCCGACCGGGCCGCCGTCGCCG
CCGCAACCGAGCAGATCACCGCCGCCGGCCGCCAGGCCGCCCCGGCCTCCGCCGACC
ACGGCCGCCCCTCCCGGCAGGCCGCCGCCGGTTGA

SEQ ID NO: 6-DpsE
GAAAGAGGAGAAATACTAGATGTCCGAGGCCGCCGACCGGGTGGCCCTGGTCACCGGC
GGCACCTCGGGCATCGGCCTGGCCGTCGTCCGGAAGCTGGCCCAGGACGGCACCCGC
GTCTTCCTGTGCGCCCGGGACGAGTCCGCCATCACCGGCACCGTCAAGGAGCTCCAGG
CCTCCGGCCTGGAAGTGGACGCCGCCCCTGCGACGTCCGCTCCACCGCCGACGTGG
ACCGGCTGGTCCAGACCGCCCGCAACCGGTTCGGCCCCATCGACATCGTCGTCAACAA
CGCCGGCCGCGGCGGCGGCGGCGTCACCGCCGAGATCACCGACGACCTGTGGCTGGA
CGTCGTGGACACCAACCTGTCCGGCGCCTTCCGGGTCACCCGGGCCGTCCTGACCGG
CGGCGCCATGCAGGAGCACGGCTGGGGCCGGATCATCTCCATCGCCTCCACCGGCGG
CAAGCAGGGCGTCGCCCTGGGCGCCCCGTACTCCGCCTCAAGTCCGGCCTGATCGG
CTTCACCAAGGCCGTGGCCCTGGAGCTGGCCAAGACCGGCATCACCGTCAACGCCGTC
TGCCCCGGCTACGTGGAGACCCCCGATGGCCCAGGGCGTCCGCCAGCGGTACGCCGCC
TTCTGGGGCATCACCGAGGACGACGTCCTGGAGAAGTTCCAGGCCAAGATCCCCCTGG
GCCGCTACTCCATGCCGGAGGAAGTCGCCGGCATGGTCCACTACCTGGCCTCCGACTC
CGCCGACTCCATCACCGCCCAGGCCATCAACGTCTGCGGCGGCCTGGGCTCCTACTGA

SEQUENCE LISTING

SEQ ID NO: 7-DpsF
GAAAGAGGAGAAATACTAGATGTCCGAGCTGCCCCTCCAGCAGACCGAGCACGAGATC
CACACCTCGGCCGCCCCGGACGCCGTCTTCGCCGTCCTGGCCGACGCCGTGCCTGG
CCGGCCGTCTTCCCGCCCTCCGTCCACGTGGAGCAGGTGGAGCACACCGGCTCCTCCG
AGCGCATCCGGATCTGGGCCACCGCCAACGGCTCCCTGCGCACCTGGACCTCGCGCC
GCGAGCTGGACGAGCGGGCCCGCCGGATCCGCTTCCGGCAGGAAGTCTCCGCCCACC
CGGTGGCCGCGATGGGCGGCGAGTGGATCGTGGAGGAAGCCGGCGACGGCGGCACC
CGCGTCCGGCTGACCCACGACTTCCGGGCCGTGGACGACGACCCCGAGACCATCGGC
TGGATCCACCGGGCCGTGGACCGGAACTCCGAGGCCGAGCTGGCCTCCCTGCGCACC
GCCCTGGAGCGGCCCGACGGCACCGCCCCCACCACCTTCGAGGACACCGTGGTGGTC
CGCGGTCGCGCCGAGGACGTCTACGACTTCCTGCACCGGTCCGACCTGTGGAAGAAGC
GCCTGTCCCACGTGGCCCGGATCGCCGTCAAGGAAGAGGAGCCCGGCCTCCAGCACAT
GGAGATGGACACCCTGACCGCCGACGGCTCCGTCCACACCACCGCCTCCGTCCGGGTC
TGCTTCCCCGAGCGTCGCGTCATCGTCTACAAGCAGCTGCGGACCCCGCCCCTGCTGG
CCCTGCACCTGGGCCGCTGGTCCGTCCGGCCCGCCGACGACGGCGACGGCATCGCCG
TCACCTCGGCCCACACCGTCTCCGTCGCCCGCTCCGCCATCCCGGGCGTCCTGGGCGC
CGGCGCCTCCGAGACCGACGCCGTGGACTTCGTCCGTCGCGCCCTGGGCCGCAACTC
CCTGCTGACCCTGGAGGCCGCCCGGCAGTACGCCGAGTCCTCCGCCTGA

SEQ ID NO: 8-DpsY
GAAAGAGGAGAAATACTAGATGCGCATCATCGACATCTCCTCCGCCGTGGACGCCTCCG
GCTGGGAGCCCGACGAGGTGCGGCACGAGGTCCACTCCCCGCGGGAGGGCGCCGTC
CACATGTCCGAGGAGATGCGCCGGCACTTCGGCGTGGCCTTCGACCCCGACGAGCTGC
CGGAGGGCGAGTTCCTGTCCCTGGACCGGCTGACCCTGACCTCGCACACCGGCACCCA
CATCGACGCCCCCTCCCACTACGGCTCCCGGGCCCACTACGGCGACGGTCGCCCGCG
CAACATCGACGAGCTGCCCCTGGACTGGTTCTACGGCCCCGGCCTGCTGCTGGACCTG
ACCGGCTGCGACGGCCCCACCGCCGGCGCCGGCGACCTGGAGAAGGAGCTGGCCCG
CATCGGCCGGGTCCCGGAGCCCGGCACCATCGTCCTGCTGCGCACCGGCGCCTCCGA
GCGGGCCGGCACCGAGCAGTACTTCACCGACTTCACCGGCCTGGACGGCCCGGCCGT
CAACCTGCTGCTGGACCACGGCGTCCGGGTCATCGGCACCGACGCCTTCTCCCTGGAC
GCCCCCTTCGGCGCCGTCATCCGCCGCTACCGCGAGACCGGCGACCGGTCCGTCCTG
TGGCCCGCCCACGTCACCGGCCGCCACCGGGAGTACTGCCAGATCGAGCGGCTGGGC
AACCTGGCCGCCCTGCCCGGCTGCGACGGCTTCCAGGTGGCCTGCTTCCCCGTCAAGA
TCACCGGCGGCGGCGCCGGCTGGACCCGGGCCGTCGCCTTCGTGGACGAGTGA

SEQ ID NO: 9-DnrG
GAAAGAGGAGAAATACTAGATGCCCCAGCCGGAGCCCAACGACGCCGGCTCCGGCTCC
GTCACCTTCGTCAACCGCTTCACCCTGTCCGGCTCCGCCGAGGACTTCGAGGCCGCCT
TCGCCGAGACCGCCGAGTTCCTGTGCCGCCGGCCCGGCTTCCGCTGGCACGCCCTGC
TGGTCCCCGCCGACACCGGCCCCGGCTCCGCCGACGCCCGCCCGCAGTACGTCAACA
TCGCCGTCTGGGACGACGAGGCCTCCTTCCGGGCCGCCGTCGCCCCACCCCGAGTTCC
CCGCCCACGCCGCCGCACTGCGGGCCCTGTCCACCTCGGAGCCGACCCTGTACCGCC
ACCGGCAGATCCGCGTCGCCCCCGACGTCCCGGCCGTCTCCGGCCCGGGTGGCCGCA
CCACCTGA

SEQ ID NO: 10-DnrC
GAAAGAGGAGAAATACTAGATGCAGGACTCCTCCTACAAGGAGCAGGTCACCCAGGCCT
TCGACCAGTCCTCCTCCACCTACGACCGCCTGGGCGTCGAGTTCTTCACCCCGATGGG
CCGCCCGCTGGTCGAGATCAGCGAGCCCGTCACCGGCGAGCGGTCCTGGACATCGG
CTGCGGCCGGGGCGCCTGCCTGTTCCCGGCCGCCGAGAAGGTCGGCCCCCAGGGCC
GCGTCCACGGCATCGACATCGCCCCCGGCATGATCGAGGAAGCCCGCAAGGAAGCCG
CCGAGCGCGCCTGCGGAACATCGCCCTGGACGTCATGGACGCCGAGACCCCGGAGC
TGCCGGCCCGCTCCTTCGACCTGGTCATGGGCTCCTACTCCGTCATCTTCCTGCCCGAC
GCCGTGGGCGCCCTGGCCCGGTACGCCGGCATCCTGGACCACGGCGGCCGGATCGCC
TTCACCTCGCCCGTCTTCCGCGCCGGCACCTTCCCCTTCCTGCCGCCCGAGTTCACCCC
GCTGATCCCGCAGGCCCTGCTGGAGCACCTGCCGGAGCAGTGGCGCCGGAGGCCCT
GGTCCGCCGGTTCAACTCCTGGCTGGAGCGGGCCGAGGACCTGCTGCGGACCCTGGA
GCGCTGCGGCTACACCTCGGTCGCCGTCACCGACGAGCCCGTGCGGATGACCGCCCT
GTCCTCCGAGGCCTGGGTGGACTGGTCCCACACCCAGGGCATGCGGCTGCTGTGGCA
GAACCTGCCCCAGGCCCAGCGGACCGAGCTGCGCGCCCGGCTGGTCGAGGGCCTGGA
CAAGCTGTCCGACGCCACCGGCGCCCTGGCCATCGACGTCCCGGTCCGCTTCGTCACC
GCCCGGGTCGCCCACTGA

SEQ ID NO: 11-DnrD
GAAAGAGGAGAAATACTAGATGTCCACCCAGATCGACCTGGTCCGTCGCATGGTCGAG
GCCTACAACACCGGCAAGACCGACGACGTCGCCGAGTTCATCCACCTGGAGTACCTGA
ACCCCGGCGCCCTGGAGCACAACCCCGAGCTGCGGGCCCCGAGGCCTTCGCCGCCG
CCGTCACCTGGCTGAAGTACGCCTTCTCCGAGGAAGCCCACCTGGAGGAGATCGAGTA
CGAGGAGAACGGCCCCTGGGTCCGGGCCAAGCTGGCCCTGTACGGCCGGCACGTGGG
CAACCTGGTGGGCATGCCCGCCACCGGCCGCCGGTTCTCCGGCGAGCAGATCCACCT
GATCCGGATCGTGGACGGCAAGATCCGGGACCACCGGGACTGGCCGGACTACCTGGG
CACCTACCGCCAGCTGGGCGAGCCGTGGCCCACCCCGGAGGGCTGGCGGCCGTGA

SEQ ID NO: 12-DnrE
GAAAGAGGAGAAATACTAGATGGAGAACACCCAGCGGTCCGTCATCGTCACCGGCGGC
GGCTCCGGCATCGGCCGGGCCGTCGCCCGTGCCTTCGCCGCCCGCGCGACCGGGTC
CTGGTCGTCGGCCGCACCGCCGGCCCCGCTGGCCGAGACCGTGGACGGCCACAAGGAC

```
GCCCACACCCTGGCCGTGGACATCACCGACCCGGCCGCACCGGAGGCCGTGGTCCGC
GAGGTCCGCGAGCGGCTGGGCGGCGTCGTGGACGTCCTGGTCAACAACGCCGCCACC
GCCGCCTTCGGCCACCTGGGCGAGCTGCACCGCACCGCCGTCGAGGCCCAGGTGGCC
ACCAACCTGGTGGCCCCCGTCCTGCTGACCCAGGCCCTGCTGGGCCCCCTGGAGACC
GCCTCCGGCCTGGTCGTCAACATCGGCTCCGCCGGCGCCCTGGGTCGCCGCGCCTGG
CCGGGCAACGCCGTCTACGGCGCCGCCAAGGCCGGCCTGGACCTGCTGACCCGCTCC
TGGGCCGTCGAGCTGGGCCCGCGCGGCATCCGGGTCGTCGGCGTCGCCCCCGGCGTC
ATCGGCACCGGCGCCGGCGTCCGCGCCGGCATGTCCCAGGAAGCCTACGACGGCTTC
CTGGAGGCGATGGGCCAGCGGGTCCCGCTGGGCCGCGTCGGTCGCCCGGAGGACGT
CGCCTGGTGGGTCGTCCGCCTGGCCGACCCCGAGGCCGCCTACGCCTCCGGCGCCGT
CCTGGCCGTGGACGGCGGCCTGTCCGTCACCTGA

SEQ ID NO: 13-DnrF
GAAAGAGGAGAAATACTAGATGGCCCTGACCAAGCCGGACGTCGATGTCCTGGTCGTC
GGCGGCGGCCTGGGCGGCCTGTCCACCGCCCTGTTCCTGGCCGCGGGGCGCCCG
CGTCCTGCTGGTCGAGCGCCACGCCTCCACCTCCGTCCTGCCGAAGGCCGCCGGCCA
GAACCCGCGGACGATGGAGCTGTTCCGCTTCGGCGGCGTCGCCGACGAGATCCTGGC
CACCGACGACATCCGCGGCGCCCAGGGCGACTTCACCATCAAGGTCGTCGAGCGCGTC
GGCGGCCGGGTCCTGCACTCCTTCGCCGAGTCCTTCGAGGAGCTGGTCGGCGCCACC
GAGCAGTGCACCCCGATGCCCTGGGCCCTGGCCCCGCAGGACCGCGTCGAGCCGGTC
CTGGTCGCCCACGCCGCCAAGCACGGCGCCGAGATCCGCTTCGCCACCGAGCTGACCT
CCTTCCAGGCCGGCGACGACGGCGTCACCGCCCGGCTGCGGGACCTGGGCACCGGCG
CCGAGTCCACCGTCTCCGCCCGCTACCTGGTCGCCGCCGACGGCCCGCGGTCCGCCA
TCCGCGAGTCCCTGGGCATCACCCGGCACGGCCACGGCACCCTGGCCCACTTCATGGG
CGTCATCTTCGAGGCCGACCTGACCGCCGTCGTCCCGCCCGGCTCCACCGGCTGGTAC
TACCTGCAACACCCGGACTTCACCGGCACCTTCGGCCCCACCGACCGGCCGAACCGCC
ACACCTTCTACGTCGCCACCACCCCGGAGCGCGGCGAGCGGCCGGAGGACTACACCC
CGCAGCGCTGCACCGAGCTGATCCGCCTGGCCGTCGATGCCCCGGGCCTGGTCCCGG
ACATCCTGGACATCCAGGCCTGGGACATGGCCGCCTACATCGCCGACCGGTGGCGCGA
GGGCCCGGTCCTGCTGGTCGGCGACGCCGCCAAGGTCACCCCGCCCACCGGCGGCAT
GGGCGGCAACACCGCCATCGGCGACGGCTTCGACGTCGCCTGGAAGCTGGCCGCCGT
CCTGCGCGGCGAGGCCGGCGAGCGCCTGCTGGACTCCTACGGCGCCGAGCGGTCCCT
GGTCTCCCGGCTGGTCGTCGATGAGTCCCTGGCCATCTACGCCCAGCGCATGGCCCCA
CACCTGCTGGGCTCCGTCCCGGAGGAGCGCGGCACCGCCCAGGTCGTCCTGGGCTTC
CGCTACCGGTCCACCGCCGTCGCCGCCGAGGACGACGACCCCGAGCCGACCGAGGAC
CCGCGGCGCCCGTCCGGCCGCCCGGGCTTCCGGGCCCCGCACGTCTGGATCGAGCAG
GACGGCACCCGCCGGTCCACCGTCGAGCTGTTCGGCGACTGCTGGGTCCTGCTGGCC
GCCCCGGAGGGCGGCGCCTGGCCGGGCCGCCCGCCCGCCCCGCCCCGCATCTGGGC
CTCCGCCTCCACCTCCATCTCCTCCGCCGCCATGTCCCCGCCGCCCCCAGCCAACTGA

SEQ ID NO: 14-SnoaL
GAAAGAGGAGAAATACTAGATGGTGTCCGCCTTCAACACCGGCCGCACCGACGACGTC
GACGAGTACATCCACCCGGACTACCTGAACCCGGCCACCCTGGAGCACGGCATCCACA
CCCGGCCCCAAGGCCTTCGCCCAGCTGGTCGGCTGGGTCCGGGCCACCTTCTCCGAGG
AAGCCCGCCTGGAGGAAGTCCGGATCGAGGAGCGGGGCCCCTGGGTCAAGGCCTACC
TGGTCCTGTACGGCCGCCACGTGGGCCGGCTGGTCGGCATGCCTCCGACCGACCGCC
GGTTCTCCGGCGAGCAGGTCCACCTGATGCGGATCGTCGACGGCAAGATCCGCGACCA
CCCGGGACTGGCCCCGACTTCCAGGGCACCCTGCGCCAGCTGGGCGACCCGTGGCCCGA
CGACGAGGGCTGGCGGCCCTGA SEQ ID NO: 15-ermE*p
GaattcgcggccgcttctagagGGTACCAGCCCGACCCGAGCACGCGCCGGCACGCCTGGTCGA
TGTCGGACCGGAGTTCGAGGTACGCGGCTTGCAGGTCCAGGAAGGGGACGTCCATGC
GAGTGTCCGTTCGAGTGGCGGCTTGCGCCCGATGCTAGTCGCGGTTGATCGGCGATCG
CAGGTGCACGCGGTCGATCTTGACGGCTGGCGAGAGGTGCGGGGAGGATCTGACCGA
CGCGGTCCACACGTGGCACCGCGATGCTGTTGTGGGCACAATCGTGCCGGTTGGTAGG
ATCCTactagtagcggccgctgcag SEQ ID NO: 16-GAPDH
GaattcgcggccgcttctagagGctgctccttcggtcggacgtgcgtctacgggcaccttaccgcagccgtcggctg
tgcgacacggacggatcgggcgaactggccgatgctgggagaagcgcgctgctgtacggcgcgcaccgggtgcggag
ccctcggcgagcggtgtgaaacttctgtgaatggcctgttcggttgctttttttatacggctgccagataaggctt
gcagcatctgggcggctaccgctatgatcggggcgttcctgcaattcttagtgcgagtatctgaaaggggatacgcTa
ctagtagcggccgctgcag SEQ ID NO: 17-rpsLp
Gaattcgcggccgcttctagagcccgccgcgggcgctggaggctcgggcggggccccgggccggaggcggccgcgaccacg
acgcccgcgggacgtgacgagcggcacgactcgacgactccgggctcctttgacgctgtccgtcgcgccgggtagcgtaggac
accgtgcccgcgccgtcgggccctcgcgcgtgcactcggtcgaccgctccctgccggagtgggtgcgggtgcacggggtggctc
cccacctcctctcggatcggtcctcgcggactgccgccgtgcggaggaccggggcgacacgcccgggcgcggggtcggtgc
gggactccagacctccggggtagtcgtgcgacgggcgacgatccgggccgagccggccgtcctgggtgacgggtgccggtca
gaccagagaacaccgacagacggagacgtaTactagtagcggccgctgcag SEQ ID NO: 18-Pxnr
GaattcgcggccgcttctagagTCCGCGCCGCCGGCCCGACGGTGCCCGGCCCCGTACCCCCC
CGGGTGGTGCGGGGCCGGGCACCGGCCTTTTGGCGCTGCGGAGTTGACGGAAGTTGG
CCGAACCGGATGCGCTCGGCGCCCGGGGGCTGAAAGATGCTCACAGCCCCTTCCACG
```

```
GCGGTCCGGGAGGGGAGGCCGGGCAACCGGTTTTCGGGGCGGAGTGTCCGGTATGC
GGACGGCCGCGCCCGATAGATGTGTAACGAGTCCGTTTCGCAACCATCTATCTCGGATC
GGTTTGTCCGGATTTTGGAAGATGTGAGTGTCAGGTGTGATCGAACCGAGACCAAAAGG
GTGTGGTCGGGCCGAACACCATGGCTAATAGTTGAGCGCGTAGAGCTCGGGTCAATGG
GTCACGCGCTGTGGGGAGCGCCGACTCACGAGCACACTGGGGCACTCGATCTTCGCCG
TCAGGGGTGTCGGCGGATCGTCCTGTGCCCTCTCTTGCAGTGAACAAGTGGACTCATTa
ctagtagcggccgctgcag SEQ ID NO: 19-kasOp*
ATGaattcgcggccgcttctagagTGTTCACATTCGAACGGTCTCTGCTTTGACAACATGCTGTGC
GGTGTTGTAAAGTCGTGGCCAGGAGAATACGACAGCGTGCAGGACTGGGGGAGTGCGC
ATTactagtagcggccgctgcagTA SEQ ID NO: 20-AknB
GAATTCGCGGCCGCTTCTAGAGAAAGAGGAGAAATACTAGATGACCGCCCGTCGCGTG
GTCATCACCGGCCTGGGCGTCATCGCCCGGGTGGCATCGGCACCAAGGCCTTCTGGG
AGCGGATCGTCTCCGGCGTCTCCGCCACCCGCACCATCACCGCCTTCGACGCCTCCGA
GTTCCGCTCCCGGATGGCCGCCGAGTGCGACTTCGACGGCGTCCGCTCCGGCCTGAC
CGTCCGGGACACCGCCCGCCTGGACCGGGCCACCCAGTTCGCCGTGGTGGCCGCCCG
CGAGGCCCTGGCCGACTCCGGCATCGAGATCGACGAGCGCAACGCCCACCGGACCGG
CGTCTCCCTGGGCTCCGCCGTCGGCTGCACCCAGAAGCTGGAGGAAGAGTACGTGGCC
CGCTCCGACGGTGGCCAGCGGTGGCTCGTGGACCACGCCGCCGGCACCCCGTACCTG
TACGACTACTTCGTCCCGTCCTCGATGGCCGCCGAGGTCGCCTGGGAGGCCGGCGCC
GAGGGCCCGGCCGCCCTGGTCTCCGCCGGCTGCACCTCGGGCCTGGACTCCCTGGGC
CACGCCCTGGACCTGATCCGCGAGGGCGCCGTGGACATCATGATCGCCGGCGGCTCC
GACGCCCCCATCGCCCCCATCACCGTGGCCTGCTTCGACGCCATCAAGGCCACCTCGC
CGCGCAACGACACCCCGGAGCACGCCTCCCGGCCGTTCGACCGCACCCGGTCCGGCT
TCGTCCTGGGCGAGGGCGCCGCCGTCCTGGTCCTGGAGGAGCGGGAGTCCGCCCTGC
GCCGCGGTGCCCAAATCTACGCCGAGATCGCCGGCTACGCCGGCCGCGCCAACGCCC
ACCACATGACCGGCCTGCGGCCCGACGGCCTGGAGATGTCCGCCGCCATCACCGGCG
CCCTGGACGACGCCCGCATCGACCGGGAGGCCGTGGGCTACGTCAACGCCCACGGCA
CCGCGACCCGCCAGAACGACATCCACGAGACCGCCGCCATCAAGCACTCCCTGGGCGA
GCACGCCCGCCGGGTCCCGGTCTCCTCCATCAAGGCCGTCATCGGCCACTCCCTGGGC
GCCGTGGGCTCCATCGAGGCCGTCGCCTCCGCCCTGGTCATCCGCCACGGCGTCGTC
CCGCCCACCGCCGGCCTGCACGAGCCGGACCCGCAGCTGGACCTGGACTACGTCCCC
CTGATCGCCCGGGACCAGGCCACCGACACCGTCCTGACCGTGGGCTCCGGCTTCGGC
GGCTTCCAGTCCGCGATGGTCCTGACCTCGGCCGAGGGCGGCCGGTCCTGATACTAGT
AGCGGCCGCTGCAG SEQ ID NO: 21-AknC
GAATTCGCGGCCGCTTCTAGAGAAAGAGGAGAAATACTAGATGTCCGCCGCCACCGTG
GTCACCGGCATCGGCGTCCTGGCCCCGAACGGCATCGGCGCCGAGGAGTTCTGGGCC
GCCACCCTGCGGGCCGAGTCCGGCATCGGCCGGATCACCCACTTCGAGCCCGCCTCCT
ACCCCTCCCGGCTGGCCGGCGAGGTCACCGGCTTCTCCGCCCGCGAGCACCTGCCCT
CCCGGCTGGTCCCGCAGACCGACCGGACCACCCAGTTCGCCCTGACCGGCTCCGAGT
GGGCCCTGCGGGACTCCGGCCTGTCCGCCGACACCCTGCCGGCCGGTGAGCGCGGC
GTCGTCACCGCCTCCGCCTCCGGCGGCTTCGAGTTCGGCCAGCGGGAGCTGGGCCAC
CTGTGGGGCAAGGACCCGCGCCACGTCTCCGCCTACATGTCCTTCGCCTGGTTCTACG
CCGTCAACTCCGGCCAGATCAGCATCCGCCACGACCTGCGGGCCCTGACCGGCGTCCT
GGTCACCGACCAGGCCGGCGGCCTGGACGCCGTGGCCCAGGCCCGCCGGCGCATCC
GCAAGGGCACCCCGGTCATGCTGTCCGGCGGCATGGACGCCTCCCTGTGCCCGTACG
GCCTGGTCGCCCAGATCAGCGCCGGCATGCTGTCCGAGTCCGACGACCCCACCCGCG
CCTACCGGCCGTTCGACCCCGCGCCGACGGCCACGTCCCGGGCGAGGGCGGCGCCA
TCCTGACCCTGGAGGACGGCGACCGCGCCCGCGCCCGCGGTGCCCGGTCCCACGGCG
AGATCAGCGGCTACGCCGCCACCTTCGACCCGCGCCCGGGCTCCGGCCGGCCCGCCA
ACCTGGACCGCGCCATCCGCGGTGCCCTGGCCGACGCCGGCCTGTCCCCGCGCGACA
TCGCCTTCGTCCTGGCCGACGGCGCCGGCGAGCCCGAGCCGGACCCGCCGCGAGGCC
GTGCCCTGACCGACGTCTTCGGCCCGCGCGGCGTCCCCGTCACCGTCCCGAAGTCCAT
GACCGGCCGGCTGTACGCCGGCGCCGCCCCGCTGGACCTGGTCACCGCCCTGTTCGC
CCTGCGGGACGGCTCGTCCCGCCCACCGTCCACGTGGACGAGCCGGACCCCGCCTA
CGACATCGACCTGGTCACCGGCTCCGCCCGCCCCGTCCGGGGCGACGCCGCCCTGGT
CCTGGCCCGCGGCCGGGGCGGCTTCAACTCCGCGATGGTCGTCCGTCGCCCGCCGGC
CGCCTGATACTAGTAGCGGCCGCTGCAG SEQ ID NO: 22-AknD
GAATTCGCGGCCGCTTCTAGAGAAAGAGGAGAAATACTAGATGTCCGCCTTCACCGTCG
AGGAGCTGTTCCAGATCATGCGCGAGTGCGCCGGCGAGGAAGAGGCCGTGGACCTGG
CCGACGCCGCCGAGCAGGAGTTCGCCCTGCTGGGCTACGACTCCCTGGCCCTGATGGA
GGCCATCTCCCGCGTCGAGCGGGCCTGGGCATCGCCCTGCCGGAGGAGACCGTGGG
CGAGGTCCTGACCCCGGCCGCCTTCGTGGACGTGGTCAACGCCGAGCTGGCCCCGGTC
CGCCCCGGTCGTCGAGGCCGCCGGTTGATACTAGTAGCGGCCGCTGCAG SEQ ID NO: 23-AknE2
GAATTCGCGGCCGCTTCTAGAGAAAGAGGAGAAATACTAGATGACCGAGGAGCACCTG
GACCCGGCCGGCGGCGCCCCGCTGGCCCAGGCCCGGCCCAGGACATCCGCATCGC
CGGCTGCGCCGTCTGGCTGCCGCCCCGGGCCCCCGTCGCCCAGGCCGTCGCCGCCG
GTCTGTGCGACGAGGCCCTGGCCACCGCCACCGCGATGGTCTCCGTCGCCGTCGCCC
```

```
AGGACGAGCCGGCCCCCGAGATGGCCGCCCGTGCCGCCCGCACCGCCCTGGCCCGC
GGCGGCTCCGACGACGTCTCCCTGATCCTGCACGCCTCCTTCTTCTACCAGGGCCACG
ACCTGTGGGCCCCCGCCTCCTACGTCAGCGCGTGGCCGTGGCAACCACTGCCCGG
CCATCGAGGTGGGCCAGGTCTCCAACGGTGGCATGGCCGCCCTGGGCCTGGCCGTGG
ACCACCTGTCCGCCGGCCGCCCGGCCGGCGCCGCCGGTCGCCGCGTCCTGGTCACCA
CCGGCGACGCCTTCCGTCCGCCGGGCTTCGACCGCTGGCGGTCCGACCCCGGCACCT
TCTACGCGACGGCGGCACCGCCCTGGTCCTGTCCTCCCAGGAAGGCTTCGCCCGCAT
CCGGGGCCTGGCCACCGTCTCCGCCCCCGAGCTGGAGGGCATGCACCGCGGCGACGA
CCCCTTCGGCTCCGCCCCGTTCTCCCACCGGCCGGTGGTGGACCTGGAGGCCTGCAAG
AAGGACTTCCTGGCCTCCCGCGGGTCACCCAGGTCATCGCCGCCTCCGCCGCCGCCC
AGGACGCCGCCCTGGGCCAGGCCCTGGCCGCCGCCGGTGCCGAGCTGGCCGACATCG
ACCGCTTCGTCCTGCCCGCACATGGGCCGCAAGCGGCTGCGCGCCGGCTTCCTGAACCG
CCTGGGCATCGGCGAGGACCGCACCACCTGGGAGTGGTCCCGGGGCGTCGGCCACCT
GGGCGCCGGCGACCAGATCGCCGGCTTCGACCACCTGGTGGGCTCCGGCTCCCTGGG
CCCCGGCGACCTGGTCCTGTGGATGTCCGTGGGCGCCGGCTTCACCTACTCCTGCGCC
GTCGTCGAGATGCTGGAGCGCCCCGGCTGGGCCGCCACCGCCGGCACCGCCGGCGC
CGCCTGATACTAGTAGCGGCCGCTGCAG

SEQ ID NO: 24-AknF
GAATTCGCGGCCGCTTCTAGAGAAAGAGGAGAAATACTAGATGACCGGCACCGCCGGC
GCCCTGCCCGTGGCCCTGCTGCTGCCCGGCCAGGGCTCCCAGCACCGTCGCATGGCC
GCCGGTCTGTACGGCCACGAGCCCGTCTTCACCGAGGCGATGGACGAGTTCTTCGACG
CCGCCGGTCCCGAGGGCGACCCGCTGCGCGACGACTGGCTGGCCGAGCGGCCCGTCA
CCGACATCGACCACGTCACCCGCTCCCAGCCCTGCTGTTCGCCGTGGACCACGCCCT
GGGCCGGCTGGTCCTGGGCCGCGGCGTCCGGCCGGCCGCACTGCTGGGCCACTCCAT
CGGCGAGCTGGCCGCCGCAACCCTGGCCGGCGTCTTCGCCCCGCGCGACGCCGCCG
GCCTGGTCCTGGACCGGATCCGCCGGCTGTCCGCCGCCCCGCCCGGCGGCATGCTGG
CCGTCGCCGCCTCCACCGCCGAGGTCGCCCCCTACCTGCGCGGCGACGTCGTCGTCG
GCGCCGTCAACGCCCCGCGTCAGACCGTCCTGGCCGGCCCGGACGGCCCCCTGGACG
AGGTGGACCGCGCCCTGCGGGAGGCCGGCTTCGTCTGCCGCCGGGTCCCCTCCCTGT
CCGCCTTCCACTCCCCCGTCCTGGAGCCGGCCTGCCGCGGCGCCGCCCCGCTGTTCG
CCGCCGCATGCAAGCACCCGCCCGCCGTCCGGTCCACTCCGCCTACACCGCCGCCC
CGCTGACCGAGTCCGACATCGACGACCCGGCCTTCTGGGCCCGCCAGCCGGTCGCCC
CCGTCCTGTTCTGGCCGGCCCTGGAGGGCTGCTGGCCACCGGCGACCACCTGCTGG
TCGAGGTCGGCCCCGGCCAGGGCCTGTCCCAGCTGGTCCGCCGGCACCCGGCCGTCC
GCCGGGGCGGCTCCGCCGTCGTCTCCCTGCTGCCCGCCGCCCCGGTCCGCCGGAGG
CCGACCGGGCCGCCGTCGCCGCCGCAACCGAGCAGATCACCGCCGCCGGCCGCCAG
GCCGCCCCGGCCTCCGCCGACCACGGCCGCCCCTCCCGGCAGGCCGCCGCCGGTTGA
TACTAGTAGCGGCCGCTGCAG

SEQ ID NO: 25-DpsE
GAATTCGCGGCCGCTTCTAGAGAAAGAGGAGAAATACTAGATGTCCGAGGCCGCCGAC
CGGGTGGCCCTGGTCACCGGCGGCACCTCGGGCATCGGCCTGGCCGTCGTCGGAAG
CTGGCCCAGGACGGCACCCGCGTCTTCCTGTGCGCCCGGGACGAGTCCGCCATCACC
GGCACCGTCAAGGAGCTCCAGGCCTCCGGCCTGGAAGTGGACGGCGCCCCCTGCGAC
GTCCGCTCCACCGCCGACGTGGACCGGCTGGTCCAGACCGCCCGCAACCGGTTCGGC
CCCATCGACATCGTCGTCAACAACGCCGGCCGCGGCGGCGGCGGCGTCACCGCCGAG
ATCACCGACGACCTGTGGCTGGACGTCGTGGACACCAACCTGTCCGGCGCCTTCCGGG
TCACCCGGGCCGTCCTGACCGGCGGCGCCATGCAGGAGCACGGCTGGGGCCGGATCA
TCTCCATCGCCTCCACCGGCGGCAAGCAGGGCGTCGCCCTGGGCGCCCCGTACTCCG
CCTCCAAGTCCGGCCTGATCGGCTTCACCAAGGCCGTGGCCCTGGAGCTGGCCAAGAC
CGGCATCACCGTCAACGCCGTCTGCCCCGGCTACGTGGAGACCCGATGGCCCAGGG
CGTCCGCCAGCGGTACGCCGCCTTCTGGGGCATCACCGAGGACGACGTCCTGGAGAA
GTTCCAGGCCAAGATCCCCCTGGGCCGCTACTCCATGCCGGAGGAAGTCGCCGGCATG
GTCCACTACCTGGCCTCCGACTCCGCCGACTCCATCACCGCCCAGGCCATCAACGTCT
GCGGCGGCCTGGGCTCCTACTGATACTAGTAGCGGCCGCTGCAG

SEQ ID NO: 26-DpsF
GAATTCGCGGCCGCTTCTAGAGAAAGAGGAGAAATACTAGATGTCCGAGCTGCCCCTCC
AGCAGACCGAGCACGAGATCCACACCTCGGCCGCCCCGGACGCCGTCTTCGCCGTCCT
GGCCGACGCCCGTGCCTGGCCGGCCGTCTTCCCGCCCTCCGTCCACGTGGAGCAGGT
GGAGCACACCGGCTCCTCCGAGCGCATCCGGATCTGGGCCACCGCCAACGGCTCCCT
GCGCACCTGGACCTCGCCGCGAGCTGGACGAGCGGGCCGCCGGATCCGCTTCCG
GCAGGAAGTCTCCGCCCACCCGGTGGCCGCGATGGGCGGCGAGTGGATCGTGGAGGA
AGCCGGCGACGCGGCACCCGCGTCCGGCTGACCCACGACTTCCGGGCCGTGGACGA
CGACCCCGAGACCGGCTGGATCCACCGGGCCGTGGACCGGAACTCCGAGGCCGA
GCTGGCCTCCCTGCGCACCGCCCTGGAGCGGCCCGACGGCACCGCCCCACCACCTT
CGAGGACACCGTGGTGGTCCGCGGTCGCGCCGAGGACGTCTACGACTTCCTGCACCG
GTCCGACCTGTGGAAGAAGCGCCTGTCCCACGTGGCCCGGATCGCCGTCAAGGAAGAG
GAGCCCGGCCTCCAGCACATGGAGATGGACACCCTGACCGCCGACGGCTCCGTCCACA
CCACCGCCTCCGTCCGGGTCTGCTTCCCCGAGCGTCGCGTCATCGTCTACAAGCAGCT
GCGGGACCCCGCCCCTGCTGGCCCTGCACCTGGGCGCTGGTCCGTCCGGCCCGCGA
CGACGGCGACGGCATCGCCGTCACCTCGGCCCACACCGTCTCCGTGCCGCTCCGC
CATCCCGGGCGTCCTGGGCGCCGGCGCCTCCGAGACCGACGCCGTGGACTTCGTCCG
TCGCGCCCTGGGCCGCAACTCCCTGCTGACCCTGGAGGCCGCCCGGCAGTACGCCGA
GTCCTCCGCCTGATACTAGTAGCGGCCGCTGCAG
```

SEQUENCE LISTING

SEQ ID NO: 27-DpsY
GAATTCGCGGCCGCTTCTAGAGAAAGAGGAGAAATACTAGATGCGCATCATCGACATCT
CCTCCGCCGTGGACGCCTCCGGCTGGGAGCCCGACGAGGTGCGGCACGAGGTCCACT
CCCCGCGGGAGGGCGCCGTCCACATGTCCGAGGAGATGCGCCGGCACTTCGGCGTGG
CCTTCGACCCCGACGAGCTGCCGGAGGGCGAGTTCCTGTCCCTGGACCGGCTGACCCT
GACCTCGCACACCGGCACCCACATCGACGCCCCTCCCACTACGGCTCCCGGGCCCAC
TACGGCGACGGTCGCCCGCGCAACATCGACGAGCTGCCCCTGGACTGGTTCTACGGCC
CCGGCCTGCTGCTGGACCTGACCGGCTGCGACGGCCCCACCGCCGGCGCCGGCGACC
TGGAGAAGGAGCTGGCCCGCATCGGCCGGGTCCCGGAGCCCGGCACCATCGTCCTGC
TGCGCACCGGCGCCTCCGAGCGGGCCGGCACCGAGCAGTACTTCACCGACTTCACCG
GCCTGGACGGCCCGGCCGTCAACCTGCTGCTGGACCACGGCGTCCGGGTCATCGGCA
CCGACGCCTTCTCCCTGGACGCCCCCTTCGGCGCCGTCATCCGCCGCTACCGCGAGAC
CGGCGACCGGTCCGTCCTGTGGCCCGCCCACGTCACCGGCCGCCACCGGGAGTACTG
CCAGATCGAGCGGCTGGGCAACCTGGCCGCCCTGCCCGGCTGCGACGGCTTCCAGGT
GGCCTGCTTCCCCGTCAAGATCACCGGCGGCGGCGCCGGCTGGACCCGGGCCGTCGC
CTTCGTGGACGAGTGATACTAGTAGCGGCCGCTGCAG

SEQ ID NO: 28-DnrG
GAATTCGCGGCCGCTTCTAGAGAAAGAGGAGAAATACTAGATGCCCCAGCCGGAGCCC
AACGACGCCGGCTCCGGCTCCGTCACCTTCGTCAACCGCTTCACCCGTGTCCGGCTCCG
CCGAGGACTTCGAGGCGCGCCTTCGCCGAGACCGCCGAGTTCCTGTGCCGCCGGCCCG
GCTTCCGCTGGCACGCCCTGCTGGTCCCCGCCGACACCGGCCCCGGCTCCGCCGACG
CCCGCCCGCAGTACGTCAACATCGCCGTCTGGGACGACGAGGCCTCCTTCCGGGCCGC
CGTCGCCCACCCCGAGTTCCCCGCCCACGCCGCCGCACTGCGGCCCTGTCCACCTC
GGAGCCGACCCTGTACCGCCACCGGCAGATCCGCGTCGCCCCCGACGTCCCGGCCGT
CTCCGGCCCGGGTGGCCGCACCACCTGATACTAGTAGCGGCCGCTGCAG

SEQ ID NO: 29-DnrC
GAATTCGCGGCCGCTTCTAGAGAAAGAGGAGAAATACTAGATGCAGGACTCCTCCTACA
AGGAGCAGGTCACCCAGGCCTTCGACCAGTCCTCCTCCACCTACGACCGCCTGGGCGT
CGAGTTCTTCACCCCGATGGGCCGCCCGCTGGTCGAGATCAGCGAGCCCGTCACCGGC
GAGCGGGTCCTGGACATCGGCTGCGGCCGGGGCGCCTGCCTGTTCCCGGCCGCCGAG
AAGGTCGGCCCCCAGGGCCGCGTCCACGGCATCGACATCGCCCCGGCATGATCGAG
GAAGCCCGCAAGGAAGCCGCCGAGCGCGGCCTGCGGAACATCGCCCTGGACGTCATG
GACGCCGAGACCCCGGAGCTGCCGGCCCGCTCCTTCGACCTGGTCATGGGCTCCTACT
CCGTCATCTTCCTGCCCGACGCCGTGGGCGCCCTGGCCCGGTACGCCGGCATCCTGGA
CCACGGCGGCCGGATCGCCTTCACCTCGCCCGTCTTCCGCGCCGGCACCTTCCCCTTC
CTGCCGCCCGAGTTCACCCCGCTGATCCCGCAGGCCCTGCTGGAGCACCTGCCGGAG
CAGTGGCGCCCGGAGGCCCTGGTCCGCCGGTTCAACTCCTGGCTGGAGCGGGCCGAG
GACCTGCTGCGGACCCTGGAGCGCTGCGGCTACACCTCGGTCGCCGTCACCGACGAG
CCCGTGCGGATGACCGCCCTGTCCTCCGAGGCCTGGGTGGACTGGTCCCACACCCAG
GGCATGCGGCTGCTGTGGCAGAACCTGCCCCAGGCCCAGCGGACCGAGCTGCGCGCC
CGGCTGGTCGAGGGCCTGGACAAGCTGTCCGACGCCACCGGCGCCCTGGCCATCGAC
GTCCCGGTCCGCTTCGTCACCGCCCGGGTCGCCCACTGATACTAGTAGCGGCCGCTGC
AG

SEQ ID NO: 30-DnrE
GAATTCGCGGCCGCTTCTAGAGAAAGAGGAGAAATACTAGATGTCCACCCAGATCGACC
TGGTCCGTCGCATGGTCGAGGCCTACAACACCGGCAAGACCGACGACGTCGCCGAGTT
CATCCACCTGGAGTACCTGAACCCCGGCGCCCTGGAGCACAACCCCGAGCTGCGGGG
CCCCGAGGCCTTCGCCGCCGCCGTCACCTGGCTGAAGTACGCCTTCTCCGAGGAAGCC
CACCTGGAGGAGATCGAGTACGAGGAGAACGGCCCCTGGGTCCGGGCCAAGCTGGCC
CTGTACGGCCGGCACGTGGGCAACCTGGTGGGCATGCCCGCCACCGGCCGCCGGTTC
TCCGGCGAGCAGATCCACCTGATCCGGATCGTGGACGGCAAGATCCGGGACCACCGG
GACTGGCCGGACTACCTGGGCACCTACCGCCAGCTGGGCGAGCCGTGGCCCACCCCG
GAGGGCTGGCGGCCGTGATACTAGTAGCGGCCGCTGCAG

SEQ ID NO: 31-DnrF
GAATTCGCGGCCGCTTCTAGAGAAAGAGGAGAAATACTAGATGGCCCTGACCAAGCCG
GACGTCGATGTCCTGGTCGTCGGCGGCGGCCTGGGCGGCCTGTCCACCGCCCTGTTC
CTGGCCCGCCGGGGCGCCCGCGTCCTGCTGGTCGAGCGCCACGCCTCCACCTCCGTC
CTGCCGAAGGCCGCCGGCCAGAACCCGCGGACGATGGAGCTGTTCCGCTTCGGCGGC
GTCGCCGACGAGATCCTGGCCACCGACGACATCCGCGGCGCCCAGGGCGACTTCACC
ATCAAGGTCGTCGAGCGCGTCGGCGGCCGGGTCCTGCACTCCTTCGCCGAGTCCTTCG
AGGAGCTGGTCGGCGCCACCGAGCAGTGCACCCCGATGCCCTGGGCCCTGGCCCCGC
AGGACCGCGTCGAGCCGGTCCTGGTCGCCCACGCCGCCAAGCACGGCGCCGAGATCC
GCTTCGCCACCGAGCTGACCTCCTTCCAGGCCGGCGACGACGCGTCACCGCCCGGC
TGCGGGACCTGGGCACCGGCGCCGAGTCCACCGTCTCCGCCCGCTACCTGGTCGCCG
CCGACGCCCGCGGTCCGCCATCCGCGAGTCCCTGGGCATCACCCGGCACGGCCACG
GCACCCTGGCCCACTTCATGGGCGTCATCTTCGAGGCCGACCTGACCGCCGTCGTCCC
GCCCGGCTCCACCGGCTGGTACTACCTGCAACACCCCGGACTTCACCGGCACCTTCGGC
CCCACCGACCGGCCGAACCGCCACACCTTCTACGTCGCCACCCACCCCGGAGCGCGGC
GAGCGGCCGGAGGACTACACCCCGCAGCGCTGCACCGAGCTGATCCGCCTGGCCGTC
GATGCCCCGGGCCTGGTCCCGGACATCCTGGACATCCAGGCCTGGGACATGGCCGCCT
ACATCGCCGACCGGTGGCGCGAGGGCCCGGTCCTGCTGGTCGGCGACGCCGCCAAGG
TCACCCCGCCCACCGGCGGCATGGGCGGCAACACCGCCATCGGCGACGGCTTCGACG
TCGCCTGGAAGCTGGCCGCCGTCCTGCGCGGCGAGGCCGGCGAGCGCCTGCTGGACT

```
CCTACGGCGCCGAGCGGTCCCTGGTCTCCCGGCTGGTCGTCGATGAGTCCCTGGCCAT
CTACGCCCAGCGCATGGCCCCACACCTGCTGGGCTCCGTCCCGGAGGAGCGCGGCAC
CGCCCAGGTCGTCCTGGGCTTCCGCTACCGGTCCACCGCCGTCGCCGCCGAGGACGA
CGACCCCGAGCCGACCGAGGACCCGCGGCGCCCGTCCGGCCGCCCGGGCTTCCGGG
CCCCGCACGTCTGGATCGAGCAGGACGGCACCCGCCGGTCCACCGTCGAGCTGTTCG
GCGACTGCTGGGTCCTGCTGGCCGCCCCGGAGGGCGGCGCCTGGCCGGGCCGCCCG
CCCCGCCCCGCCCCGCATCTGGGCCTCCGCCTCCACCTCCATCTCCTCCGCCGCCATGT
CCCCGCCGCCCCCAGCCAACTGATACTAGTAGCGGCCGCTGCAG

SEQ ID NO: 32-SnoaL
GAATTCGCGGCCGCTTCTAGAGAAAGAGGAGAAATACTAGATGGTGTCCGCCTTCAACA
CCGGCCGCACCGACGACGTCGACGAGTACATCCACCCGGACTACCTGAACCCGGCCAC
CCTGGAGCACGGCATCCACACCGGCCCCAAGGCCTTCGCCCAGCTGGTCGGCTGGGT
CCGGGCCACCTTCTCCGAGGAAGCCCGCCTGGAGGAAGTCCGGATCGAGGAGCGGGG
CCCCTGGGTCAAGGCCTACCTGGTCCTGTACGGCCGCCACGTGGGCCGGCTGGTCGG
CATGCCTCCGACCGACCGCCGGTTCTCCGGCGAGCAGGTCCACCTGATGCGGATCGTC
GACGGCAAGATCCGCGACCACCGGGACTGGCCCGACTTCCAGGGCACCCTGCGCCAG
CTGGGCGACCCGTGGCCCGACGACGAGGGCTGGCGGCCCTGATACTAGTAGCGGCCG
CTGCAG SEQ ID NO: 33-ErmE*p
GaattcgcggccgcttctagagGGTACCAGCCCGACCCGAGCACGCGCCGGCACGCCTGGTCGA
TGTCGGACCGGAGTTCGAGGTACGCGGCTTGCAGGTCCAGGAAGGGGACGTCCATGC
GAGTGTCCGTTCGAGTGGCGGCTTGCGCCCGATGCTAGTCGCGTTGATCGGCGATCG
CAGGTGCACGCGGTCGATCTTGACGGCTGGCGAGAGGTGCGGGGAGGATCTGACCGA
CGCGGTCCACACGTGGCACCGCGATGCTGTTGTGGGCACAATCGTGCCGGTTGGTAGG
ATCCTactagtagcggccgctgcag SEQ ID NO: 34-GAPDH
GaattcgcggccgcttctagagGctgctccttcggtcggacgtgcgtctacgggcaccttaccgcagccgtcggctgtgcgacac
ggacggatcgggcgaactggccgatgctgggagaagcgcgctgctgtacggcgcgcaccgggtgcggagcccctcggcgag
cggtgtgaaacttctgtgaatggcctgttcggttgctttttttatacggctgccagataaggcttgcagcatctgggcggctaccg
ctatgatcggggcgttcctgcaattcttagtgcgagtatctgaaaggggatacgcTactagtagcggccgctgcag SEQ ID NO: 35-rpsLp
Gaattcgcggccgcttctagagcccgccgcgggcgctggaggctcgggcgggccccgggccggaggcggccgcgaccacg
acgcccgcgggacgtgacgagcggcacgactcgacgactccgggctccttttgacgctgtccgtcgcgccgggtagcgtaggac
accgtgcccgcgccgtcgggccctcgcgcgtgcactcggtcgaccgctccctgccggagtgggtgcgggtgcacggggtggctc
cccacctcctctcggatcggtcctcgcggactgccgccgtgcggaggaccggggcgacacgcccgggcgcggggtcggtgc
gggactccagacctccggggtagtcgtgcgacgggcgacgatccgggccgagccggccgtcctgggtgacgggtgccggtca
gaccagagaacaccgacagacggagacgtaTactagtagcggccgctgcag SEQ ID NO: 36-Pxnr
GaattcgcggccgcttctagagTCCGCGCCGCCGGCCCGACGGTGCCCGGCCCCGTACCCCCC
CGGGTGGTGCGGGGCCGGGCACCGGCCTTTTGGCGCTGCGGAGTTGACGGAAGTTGG
CCGAACCGGATGCGCTCGGCGCCCGGGGGCTGAAAGATGCTCACAGCCCCTTTCCACG
GCGGTCCGGAGGGGAGGCCGGGCAACCGGTTTTCGGGGCGGAGTGTCCGGTATGC
GGACGGCCGCGCCCGATAGATGTGTAACGAGTCCGTTTCGCAACCATCTATCTCGGATC
GGTTTGTCCGGATTTTGGAAGATGTGAGTGTCAGGTGTGATCGAACCGAGACCAAAGG
GTGTGGTCGGGCCGAACACCATGGCTAATAGTTGAGCGCGTAGAGCTCGGGTCAATGG
GTCACGCGCTGTGGGGAGCGCCGACTCACGAGCACACTGGGGCACTCGATCTTCGCCG
TCAGGGGTGTCGGCGGATCGTCCTGTGCCCTCTCTTGCAGTGAACAAGTGGACTCATTa
ctagtagcggccgctgcag SEQ ID NO: 37-KasOP*
ATGaattcgcggccgcttctagagTGTTCACATTCGAACGGTCTCTGCTTTGACAACATGCTGTGC
GGTGTTGTAAAGTCGTGGCCAGGAGAATACGACAGCGTGCAGGACTGGGGGAGTGCGC
ATTactagtagcggccgctgcagTA SEQ ID NO: 38-φBT1 int-attP region-neoR-oriT region of pENBT1 vector
GAATTCCCGGCGGGCTGCAGTGGCGCCGGACGGGGCTTCAGACGTTTCGGGTGCTGG
GTTGTTGTCTCTGGACAGTGATCCATGGGAAACTACTCAGCACCACCAATGTTCCCAAAA
GAAAGCGCAGGTCAGCGCCCATGAGCCAAGATCTAGGCATGTCGCCCTTCATCGCTCC
CGACGTCCCTGAGCACCTGCTGGACACTGTTCGCGTCTTCCTGTACGCGCGTCAGTCTA
AGGGCCGGTCCGACGGCTCAGACGTGTCGACCGAAGCACAGCTAGCGGCCGGTCGTG
CGTTGGTCGCGTCTCGCAACGCCCAGGGGGGTGCGCGCTGGTCGTGGCAGGTGAGT
TCGTGGACGTCGGGCGCTCCGGCTGGGACCCGAACGTGACCCGTGCCGACTTCGAGC
GCATGATGGGCGAAGTCCGCGCCGGCGAAGGTGACGTTGTCGTTGTGAATGAGCTTTC
CCGGCTCACTCGCAAGGGCGCCCATGACGCGCTCGAAATCGACAACGAATTGAAGAAG
CACGGCGTGCGCTTCATGTCGGTTCTTGAGCCGTTCCTTGACACGTCTACCCCTATCGG
CGTCGCCATTTTCGCGCTGATCGCTGCCCTTGCGAAACAGGACAGTGACCTGAAGGCG
GAGCGCCTGAAGGGTGCGAAAGACGAGATTGCCGCGCTGGGTGGCGTTCACTCGTCTT
CCGCCCCGTTCGGAATGCGCGCCGTGCGCAAGAAGGTCGATAATCTCGTGATCTCCGT
TCTTGAGCCGGACGAAGACAACCCGGATCACGTCGAGCTAGTTGAGCGCATGGCGAAA
ATGTCGTTCGAAGGCGTGTCCGACAACGCCATTGCAACGACCTTCGAGAAGGAAAGAT
CCCGTCGCCCGGAATGCTGAGAGACGCGCCACGGAAAAGCGTCTTGCGTCCGTCAAG
GCACGTCGCCTGAACGGCGCTGAAAAGCCGATCATGTGGCGCGCTCAAACGGTCCGAT
```

```
GGATTCTCAACCATCCCGCAATCGGCGGTTTCGCATTCGAGCGTGTGAAGCACGGTAAG
GCGCACATCAACGTCATACGGCGCGACCCCGGCGGCAAGCCGCTAACGCCCCACACG
GGCATTCTCAGCGGCTCGAAGTGGCTTGAGCTTCAAGAGAAGCGTTCCGGGAAGAATCT
CAGCGACCGGAAGCCTGGGGCCGAAGTCGAACCGACGCTTCTGAGCGGGTGGCGTTT
CCTGGGGTGCCGAATCTGCGGCGGCTCAATGGGTCAGTCCCAGGGTGGCCGTAAGCG
CAACGGCGACCTTGCCGAAGGCAATTACATGTGCGCCAACCCGAAGGGGCACGGCGGC
TTGTCGGTCAAGCGCAGCGAACTGGACGAGTTCGTTGCTTCGAAGGTGTGGGCACGGC
TCCGCACAGCCGACATGGAAGATGAACACGATCAGGCATGGATTGCCGCCGCTGCGGA
GCGCTTCGCCCTTCAGCACGACCTAGCGGGGGTGGCCGATGAGCGGCGCGAACAACA
GGCGCACCTAGACAACGTGCGGCGCTCCATCAAGGACCTTCAGGCGGACCGTAAGCCC
GGTCTGTACGTCGGGCGTGAAGAGCTGGAAACGTGGCGCTCAACGGTGCTGCAATACC
GGTCCTACGAAGCGGAGTGCACGACCCGACTCGCTGAGCTTGACGAGAAGATGAACGG
CAGCACCCGCGTTCCGTCTGAGTGGTTCAGCGGCGAAGACCCGACGGCCGAAGGGGG
CATCTGGGCAAGCTGGGACGTGTACGAGCGTCGGGAGTTCCTGAGCTTCTTCCTTGACT
CCGTCATGGTCGACCGGGGGCGCCACCCTGAGACGAAGAAATACATCCCCCTGAAGGA
CCGTGTGACGCTCAAGTGGGCGGAGCTGCTGAAGGAGGAAGACAGTGAAGAAGGAACACCC
CACTGAGCGGGAGCTTGCGGCGCTGTAGCGCACAGCGGGAGGGGTCGAGCCGGCGGA
CGGTTCGGCCCCTTTTTTGGCCTTGAAATCGTTAGTTAGGCTAACAAGTAGTTCCTTCGT
CACCCACAGCGGGCAGGGAGCAGTATAGGAACTTCGAAGTTCCCGCCAGCCTCGCAGAG
CAGGATTCCCGTTGAGCACCGCCAGGTGCGAATAAGGGACAGTGAAGAAGGAACACCC
GCTCGCGGGTGGGCCTACTTCACCTATCCTGCCCGGCTGACGCCGTTGGATACACCAA
GGAAAGTCTACACGAACCCTTTGGCAAAATCCTGTATATCGTGCG

```
GGCGACCGTGTCGGCGAGCCACTTCAACACCTCGGCCTCGACTTCGTCGCGGCGCACG
TAGAGGCCGGGCTCACAGGCCGACTTCCCCTTGTTCCTGCGGTTGAAGCACACGAACA
CGTGGCCCGGAACGAATCCGCCCTTCCCGTCGCGGCCGGATCGCGCAACGGCCGTCC
CGCGGCAGTGTCCGTGCCGCATGATGCCGCTGGTCGGGTATGAGGCCCGGCGGGCGC
GCGGGGGCGTCTTGCGCGTCTGCTCTCTGTGCGCCCCGTACTCCTTCCACTGCTCGGG
AACGATGAGCGCCGGCTGTGCCCCGGGGAGCCAGAGCCACCGGTTTTCTTTGCACGCA
GAGAAGTGGTCCTGTCCCAGCTTGCACCGGCACTCCGGGTCGTGGACGCGTAGCAGGC
CGGCGGCGAATCCGGAGTCGAGGTAGCGCTGAACGGTGTTGGTGCCCCAGCGGTTGC
CCCGTGTGGTGGGGATGAGTAGTTCGTCGTTCAGCCAGTAGGCGAGCTGGGAGAACCC
CTGTCCGGCGAGCTTTCGCTCGTAGAGTTCGGCCGCCACGGGGGCGAACTCTGGGTGC
CGTTCGTAGCGCTCCTCTTGCAGGCGGAACCCGCCCGGCGCGGTGAGGTCGGGTACG
CGCCTCGGGTGCCACACGTAGCCGAACCGCTGACGCCCGGTGGCGGGGAGTTTCAGG
GCCCGACGGTGGGCGTGCGTCTCCTTCCACTGTTCGCCGGCCCGATCCGACTCGAATA
CGGCGAGGTCGAACAGAATCGCGCGGTTGAAGCGTCCGACGGCCGTGCGGGCGTCGA
CTTCTTCCGTGGCGGACGCGAGGTCTCCGCCGGCCTGTTCGAGGCGGGCGAGGTTGAT
AGCGATGCCCAGGTCGTTCCGGCCGAAGCGGCTGAACTTCCATACGGCGATTCCGACG
GCCTCGCGGCCCTCGACGCGCTGGATGCCGCCCATGATCTTCCGCTTGAAGTTGCGGC
CCGTAGCGTCGAGGTCAACGATCCAGTCGACGATCCGACGTCCCGTTCGGGCGGCCCA
TGACTCGATCGCGGATTGCTGTAGCTCCGGGCTGATCTTCTCCTCGCGCCATGTGCTGA
CCCTGATGTAGCCGAGCCACGGCTCGCCCGGCGTGCGGGAGCCGCGGAACGTGCTTG
GTAGGTCTCGTTT

SEQ ID NO: 40-TG1-int-attP region-aadR-oriT region of pENTG1
GAATTCCCGGCGGCTGCAGGTGTAGGCTGGAGCTGCTTCGGAATAGGAACTTCATGA
GCTCAGCCAATCGACTGGCGAGCGGCATCCTACCGGTAGCCGCTGAGGCCGTCGGCG
AGTTCCTCCTCGTCGCCGTCGCGCTGCGCGTAGAGGGCCTGCTGGAGTGCGAAGGTGC
CTCGGATCGCCGAGATCCGCTCGGCCGTTCCGTTGTCGGCCCAGCCGCCGAGCGCGA
GCACTCGGCCCAGCAGTTCCTCGCCGTAGCTCGCCCCGATGGCGGCCAGGTCCTCAGC
CGGGTCGCCGATGCCGACCTCGTCCCAGTCGACGACGCCGCTCATGCGCGGCACTCC
GTCCACCGTCTCCCACAGGACGTTCTCGCCGCCGAGGTCACCGTGGACCACCGCGGAG
GTGAGATGGGGCAGGGCGTCGAGCGCGGCGAGCTCGCGCTCGGCACGCTCCCGGCC
GCCGTCGGACATCAGCGGGAACAGTTCGGTACGCACCCCGTGGCGAACTCCTGCCAT
CGTTCGCGGGAGCCTCCGGCAGCGCGGCGCGCACCTTCTCCTCGTCGCCCGCCGCC
GCGAGCCCGGACAGCAGGGTCGCGTACTGTCGGGCGACGGCCTCCGCCACCTCCGGG
CTGGTGAGCACATCGTCCTCCAACGGTGCTCCGGGAATGCGGCTCAGCACCAGGTACG
GCGGCTCGTCCGTGCCCTGGGCGCCGCCCTCGGACAGCGGCTGCGGCGTGCGAAACC
CGAGGTCGATCCCGGCAAGAGCGCGCAGGACGTCCGCCCTGCCGGGCAGACGGTCGG
CGGCCGCCCGGGTGCGGGCGAAGCAGACCACCCGGTGCGATCCGATCACCACATGGT
GGAACTGCCCCTCGTGGACGGCGAGTCCGCCCACGGTGTCCCCGGGCAGGAGCCGGC
TCAGCAGATCGCGGTCGTCTCAATGATTCTCATGACATTGCACTCCACCGCTGATGAC
ATCAGTCGATCATAGCACGATCAACGGCACTGTTGCAAATAGTCGGTGGTGATAAACTTA
TCATCCCCTTTTGCTGATGGAGCTGCACATGAACCCATTCAAAGGCCGGCATTTTCAGC
GTGACATCATTCTGTGGGCCGTACGCTGGTACTGCAAATACGGCATCAGTTACCGTGAG
CTGCATTTTCCGCTGCATAACCCTGCTTCGGGGTCATTATAGCGATTTTTTCGGTATATC
CATCCTTTTTCGCACGATATACAGGATTTTGCCAAAGGGTTCGTGTAGACTTTCCTTGGT
GTATCCAACGGCGTCAGCCGGGCAGGATAGGTGAAGTAGGCCCCACCCGCGAGCGGGT
GTTCCTTCTTCACTGTCCCTTATTCGCACCTGGCGGTGCTCAACGGGAATCCTGCTCTG
CGAGGCTGGCGGGAACTTCGAACTCCAGGTCGACGGATCCCCGGAATGTAAGCGTCAC
GGCACGCGCCGACTGAGAGACGTTTCCGCAGGTCAACCCCGTTCCAGCCCAACAGTGT
TAGTCTTTGCTCTTACCCAGTTGGGCGGGATAGCCTGCCCGGCATGAGCGTGAAGGTTG
AAGGCATGGTCATTCTGGCAGGCGGCTACGACCGACAGTCGGCGGAACGGGAGAACAG
TTCGACCGCTTCACCGGCCACCCAGCGCGCCGCGAACCGGGGGAAGGCTGAGGCGCT
GGCGAAGGAGTACGCGCGACGGCGTCGAGGTGAAGTGGCTGGGTCACTTCAGCGA
AGCGCCCGGCACGTCGGCATTCACGGGCGTCGACCGGCCGGAGTTCAACCGGATTTTG
GACATGTGCCGGAACCGGGAAATGAACATGATCATTGTTCATTACATTTCGCGCCTCAG
CCGCGAAGAGCCGCTGGACATTATTCCGGTCGTCACGGAATTGCTCCGGCTGGGCGTG
ACCATTGTCAGCGTGAACGAAGGCACATTCCGCCCCGGCGAAATGATGGACCTTATTCA
CCTGATCATGCGCCTTCAGGCTTCGCATGATGAGTCGAAGAACAAGAGCGTCGCCGTGT
CGAACGCTAAGGAATTGCGAAGCGGCTGGGCGGACACACGGGTCGACGCCGTACG
GATTCGACACGGTCGAGGAAATGGTTCCGAACCCGGAAGACGGCGGAAAGCTGGTTGC
CATTCGCCGACTGGTGCCCAGCGCGCACACCTGGGAAGGCGCACACGGCAGCGAAGG
GGCGGTAATCCGCTGGGCGTGGCAGGAGATCAAGACGCACCGCGATACGCCATTCAAG
GGTGGCGGAGCCGGGTCGTTTCACCCTGGGTCGCTGAACGGGCTTTGTGAGCGGCTGT
ACCGCGACAAGGTGCCTACGCGCGGCACGCTGGTCGGTAAGAAGCGCGCCGGTTCCG
ATTGGGACCCCGGCGTTTTGAAGCGCGTACTCAGCGACCCGCGCATTGCCGGGTATCA
AGCTGACATCGCATACAAGGTGCGCGCCGACGGTTCGCGGGGCGGCTTCAGCCATTAC
AAGATCAGGCGCGACCCGGTCACCATGGAGCGCTGACCCTGCCCGGCTTCGAGCCGT
ACATTCCCCCGGCGGAATGGTGGGAACTTCAGGAGTGGCTTCAGGGTCGAGGACGCGG
GAAGGGTCAGTACCGGGGGCAATCGCTCCTGTCGGCAATGGACGTCCTTTACTGCTAC
GGCTCCGGCCAGCTCGACCCGGAGACGGGTTACAGCAACGGGTCGACCATGGCGGGC
AACGTCCGCGAAGGTGATCAAGCTCACAAGTCGTCGTACGCGTGCAAGTGCCCCCGCC
GGGTTCATGACGGGTCGTCATGCTCGATCACGATGCACAACCTTGACCCGTACATCGTC
GGCGCGATCTTCGCGCGCATCACGGCCTTCGACCCTGCCGACCCTGACGACCTCGAAG
GCGACACGGCAGCGCTCATGTACGAAGCCGCACGGCGCTGGGGAGCGACGCACGAAC
GCCCGGAGTTGAAGGGTCAGCGCTCCGAACTGATGGCACAGCGCGCGGACGCCGTGA
AGGCGCTCGAAGAGCTTTACGAAGACAAGCGGAACGGCGGCTACCGGTCCGCCATGGG
ACGGCGCGCGTTTCTCGAAGAGGAAGCCGCGCTGACGCTCCGCATGGAAGGGGCCGA
```

-continued

SEQUENCE LISTING

```
AGAACGGCTTCGTCAGCTCGACGCCGCCGACTCCCCGTGCTGCCGATCGGCGAATGG
CTGGGCGACCGGGGCAGCGACCCGACGGGACCGGGTTCGTGGTGGGCGCTAGCGCC
CCTTGAAGACCGTCGGGCGTTCGTCCGGCTCTTCGTGGACCGGATCGAGGTGATCAAG
CTTCCGAAGGGCGTTCAGCGGCCCGGACGGGTTCCCCGATCGCCGACCGTGTGCGTA
TCCACTGGGCGAAGCCGAAGGTCGAGGAAGAGACGGAGCCGGAGACGCTGAACGGGT
TCACAGCGGCGGCGTGACGGCGGCACCAGCGCAACGGGAAGGGGCTTCGGCCCCTTT
TCTCGTGCCCGGCGTCGGTTCGTTGCCCTAAGCAACTGTTCCTAGCG

What is claimed is:

1. A genetically modified host organism comprising an actinomycete for producing an anthracyclinone analogue, said genetically modified host organism comprising:
   i) synthetic nucleic acids derived from at least one of *Streptomyces galilaeus* (ATCC 31615) and *Streptomyces peucetius* (ATCC 29050);
   ii) a biosynthetic pathway for producing said anthracyclinone analogue encoded by said synthetic nucleic acids, said biosynthetic pathway comprising a ketosynthase alpha, a ketosynthase beta/chain-length factor, an acyl carrier protein, a 3-oxoacyl-ACP synthase, a propionyl-CoA acyltransferase, a 9-ketoreductase, an aromatase/cyclase; and
   iii) a promoter positioned upstream of and operatively associated with said biosynthetic pathway;
   wherein the actinomycete comprises at least one of *Streptomyces lividans, Streptomyces coelicolor* A3 (2), *Streptomyces sriseus, Streptomyces albus, Streptomyces peucetius, Streptomyces galilaeus, Streptomyces cinnomonensis, Streptomyces nosalater, Streptomyces sriseoflavus, Streptomyces albaduncus, Streptomyces venezuelae,* and *Streptomyces olivaceus.*

2. The genetically modified host organism of claim 1, further comprising a transcriptional terminator operatively associated with said biosynthetic pathway.

3. The genetically modified host organism of claim 1, wherein the biosynthetic pathway further comprises: (i) a C-12 anthrone monooxygenase; (ii) an aklanonic acid methyltransferase; (iii) an aklanonic acid methyl ester cyclase; (iv) an aklaviketone ketoreductase; (v) a C-11 hydroxylase; or (vi) a nogalonic acid methyl ester cyclase; or (vii) any combination of (i)-(vi).

4. The genetically modified host organism of claim 1 wherein the actinomycete comprises at least one of *Streptomyces lividans, Streptomyces coelicolor* A3 (2), *Streptomyces albus,* and *Streptomyces venezuelae.*

5. The genetically modified host organism of claim 1 genetically engineered to lack a native polyketide biosynthetic gene.

6. The genetically modified host organism of claim 1, wherein the biosynthetic pathway comprises at least one enzyme selected from the group consisting of an aclacinomycin polyketide synthase ketosynthase (AknB), an aclacinomycin polyketide synthase chain length factor (AknC), an aclacinomycin acyl-carrier protein (AknD), an aclacinomycin polyketide synthase starting unit specificity factor AknE2 (AknE2), an aclacinomycin polyketide synthase starting unit specificity factor AknF (AknF), a daunorubicin polyketide ketoreductase (DpsE), a daunorubicin aromatase/cyclase (DpsF), and a daunorubicin second/third ring cyclase (DpsY).

7. The genetically modified host organism of claim 6, wherein the biosynthetic pathway further comprises at least one enzyme selected from the group consisting of a daunorubicin second/third ring cyclase (DpsY), an aklanoate anthrone oxygenase (DnrG), an aklanonic acid methyltransferase (DnrC), an aklanonic acid methyl ester fourth ring cyclase (DnrD), an aklaviketone 7-ketoreductase (DnrE), an aklavinone 11-hydroxylase (DnrF), and a nogalonic acid methyl ester fourth ring cyclase (SnoaL).

8. An expression vector for preparing the genetically modified host organism of claim 1, said expression vector comprising a nucleic acid sequence coding an integrase.

9. The expression vector of claim 8, wherein said integrase is TG1 integrase, BT1 integrase, SV1 integrase, or a combination thereof.

10. The expression vector of claim 9, wherein said expression vector is pENBT1 corresponding to a first synthetic nucleic acid sequence of SEQ ID NO: 38 or a second synthetic nucleic acid sequence homologous to the first synthetic nucleic acid sequence and having the same functionality as the first synthetic nucleic acid sequence.

11. The expression vector of claim 9, wherein said expression vector is pENSV1 corresponding to a first synthetic nucleic acid sequence of SEQ ID NO: 39 or a second synthetic nucleic acid sequence homologous to the first synthetic nucleic acid sequence and having the same functionality as the first synthetic nucleic acid sequence.

12. The expression vector of claim 9, wherein said expression vector is pENTG1 corresponding to a first synthetic nucleic acid sequence corresponding to SEQ ID NO: 40 or a second synthetic nucleic acid sequence homologous to the first synthetic nucleic acid sequence and having the same functionality as the first synthetic nucleic acid sequence.

13. The genetically modified host organism of claim 1, wherein the promoter comprises at least one of a glyceraldehyde 3-phosphate dehydrogenase operon promoter from *Eggerthella lenta* (Pgap), a promoter of the 30S ribosomal protein S12 from *Cellulomonas flavigena* (Prps), a peptide transport system secreted peptide-binding protein from *Streptomyces albus* (Pxnr), an erythromycin resistance gene ermE up-promoter from *Saccharopolyspora erythraea* (PermE*), an actinorhodin actII-ORF4 actI/actIIIp promoter system from *Streptomyces coelicolor* (M145PactI-actII-ORF4), an erythromycin resistance gene ermE up-promoter from *Saccharopolyspora erythraea* (ermE*p), a glyceraldehyde 3-phosphate dehydrogenase operon promoter from *Eggerthella lenta* (GAPDH), a promoter of the 30S ribosomal protein S12 from *Cellulomonas flavigena* (rpsLp), a peptide transport system secreted peptide-binding protein from *Streptomyces albus* (Pxnr), and an engineered kasO strong promoter from *Streptomyces coelicolor* M145 (kasOp*).

14. The genetically modified host organism of claim 13, wherein ermE*p has the nucleotide sequence of SEQ ID NO: 32 or a functional homolog thereof;
   GAPDH has the nucleotide sequence of SEQ ID NO: 34 or a functional homolog thereof;
   rpsLp has the nucleotide sequence of SEQ ID NO: 35 or a functional homolog thereof;
   Pxnr has the nucleotide sequence of SEQ ID NO: 36 or a functional homolog thereof; and
   kasOp* has the nucleotide sequence of SEQ ID NO: 37 or a functional homolog thereof.

15. The genetically modified host organism of claim 1, wherein at least one of the synthetic nucleic acid sequences comprises EcoRl and Xbal restriction enzyme sites at a 5' region and Spel and Pstl restriction enzyme sites at a 3' region.

16. A method for preparing an anthracyclinone analogue with a genetically modified host organism, said method comprising:
   culturing the genetically modified host organism for a period of time sufficient to prepare the anthracyclinone analogue; and
   optionally, isolating the anthracyclinone analogue from the genetically modified host organism;
   wherein the genetically modified host organism is the genetically modified host organism of claim 1.

17. The method of claim 16, wherein the anthracyclinone analogue has formula (i) or (ii):

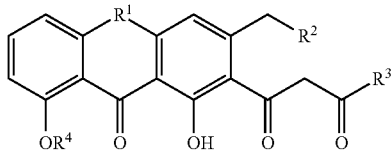
(i)

wherein $R^1$ is $CH_2$, CHOH, or C(O); $R^2$ is hydrogen, methyl, carboxyl (C(O)OH), carboxymethyl (C(O)OCH$_3$), CH$_2$OH, or a protecting group; $R_3$ is hydroxyl, methyl, ethyl, propionyl, butyl, NH$_2$, CH$_2$OH, or a protecting group; and $R^4$ is hydrogen or methyl; or

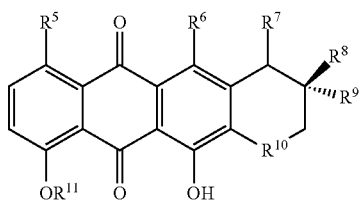
(ii)

wherein $R^5$ is hydrogen, hydroxyl, or a halogen; $R^6$ is hydrogen or hydroxyl; $R^7$ is hydrogen, carboxyl (C(O)OH), carboxymethyl (C(O)OCH$_3$), or hydroxyl; $R^8$ is methyl, ethyl, propionyl, butyl, vinyl, hydroxyl, carboxyl (C(O)OH), or a protecting group; $R^9$ is methyl, ethyl, propionyl, butyl, vinyl, hydroxyl, carboxyl (C(O)OH), or a protecting group; $R^{10}$ is CHOH, or C(O), and $R^{11}$ is H or CH$_3$;
wherein the protecting group of $R^2$, $R^3$, $R^8$, and/or $R^9$ independently comprises a substituted or unsubstituted hydrocarbyl group, an ester group, a carbonate group, a carboxy group, an aldehyde group, a ketone group, a urethane group, a silyl group, a sulfoxo group, or a phosphonic acid group.

* * * * *